(12) United States Patent
Zacouto et al.

(10) Patent No.: US 6,835,207 B2
(45) Date of Patent: Dec. 28, 2004

(54) SKELETAL IMPLANT

(75) Inventors: Fred Zacouto, 16, rue de la Convention, 75015 Paris (FR); Efren Vigil Caballero, Gijon (ES); Jose Angel Alvarez Canal, La Feiguera (ES)

(73) Assignee: Fred Zacouto, Paris (FR)

( * ) Notice: Subject to any disclaimer, the term of this patent is extended or adjusted under 35 U.S.C. 154(b) by 0 days.

(21) Appl. No.: 10/040,429

(22) Filed: Jan. 9, 2002

(65) Prior Publication Data

US 2002/0151978 A1 Oct. 17, 2002

Related U.S. Application Data

(63) Continuation of application No. 09/200,855, filed on Nov. 30, 1998, now abandoned, which is a continuation-in-part of application No. 08/897,673, filed on Jul. 21, 1997, now abandoned.

(30) Foreign Application Priority Data

Jul. 22, 1996 (FR) .............................. 96 09157
Apr. 30, 1998 (FR) .............................. 98 05549

(51) Int. Cl.[7] ................................................. A61F 2/44
(52) U.S. Cl. ............................... 623/17.12; 623/22.14; 623/23.17
(58) Field of Search ...................... 606/72, 61; 623/45, 623/17.12, 17.13, 22.14, 23.17, 23.32, 17.15

(56) References Cited

U.S. PATENT DOCUMENTS

| | | |
|---|---|---|
| 3,648,294 A | 3/1972 | Sharestani |
| 4,206,517 A | 6/1980 | Pappas et al. |
| 4,921,499 A | 5/1990 | Hoffman et al. |
| 4,932,969 A | 6/1990 | Frey et al. |
| 4,932,975 A | 6/1990 | Main et al. |
| 5,002,576 A | 3/1991 | Fuhrmann et al. |
| 5,071,435 A | 12/1991 | Fuchs et al. |
| 5,207,676 A | 5/1993 | Canadell et al. |
| 5,360,016 A | 11/1994 | Kovacevic |
| 5,375,823 A | 12/1994 | Navas |

(List continued on next page.)

FOREIGN PATENT DOCUMENTS

| | | |
|---|---|---|
| DE | G9 209584.4 | 1/1993 |
| EP | 0385929 | 9/1990 |
| EP | 0677277 | 10/1995 |
| FR | 2681525 | 3/1993 |
| FR | 2693650 | 1/1994 |
| FR | 2723841 | 3/1996 |
| WO | 94/06364 | 3/1994 |

OTHER PUBLICATIONS

"An Active Orthopaedic Implant with Variable Visco–Elastic Behavin and Adjustable Alignment," Zeller, Zacouto, Canal, and Viguier, 51st International Meeting on Advanced Spine Techniques, IMAST May 1–3, 1998.

*Reanimation and Artificial Organs, Scientific Journal of Medicine, Surgery, Cellular Biology and Related Physics,* vol. 11, No. 1, Oct. 3, 1996, Paris, France, pp. 1–15.

"Des amortisseurs et une suspension pour des prothèses osseuses intelligentes", Dr. Mara Nguyen, an article from a french language medical newspaper entitled *Le Quotidien Du Médecin*, No. 5931, Oct. 17, 1996.

*Reanimation and Artificial Organs, Scientific Journal of Medicine, Surgery, Cellular Biology and Related Physics,* vol. 12, No. 1, Dec. 1997, Paris, France, pp. 1–12.

*Primary Examiner*—Bruce Snow
(74) *Attorney, Agent, or Firm*—Greenblum & Bernstein, P.L.C.

(57) ABSTRACT

Skeletal implant of the type to be used for connecting at least two elements of the skeleton. The implant has two parts. Each of the parts is capable of being connected to one of the elements. The implant also uses at least one shock-absorbing device located between the at least two parts. The shock-absorbing device has an adjustable coefficient of resistance.

26 Claims, 26 Drawing Sheets

U.S. PATENT DOCUMENTS

| | | |
|---|---|---|
| 5,376,138 A | 12/1994 | Bouchard et al. |
| 5,389,107 A | 2/1995 | Nassar et al. |
| 5,423,816 A | 6/1995 | Lin |
| 5,466,261 A | 11/1995 | Richelsoph |
| 5,626,579 A | 5/1997 | Muschler et al. |
| 5,720,746 A | 2/1998 | Soubeiran |

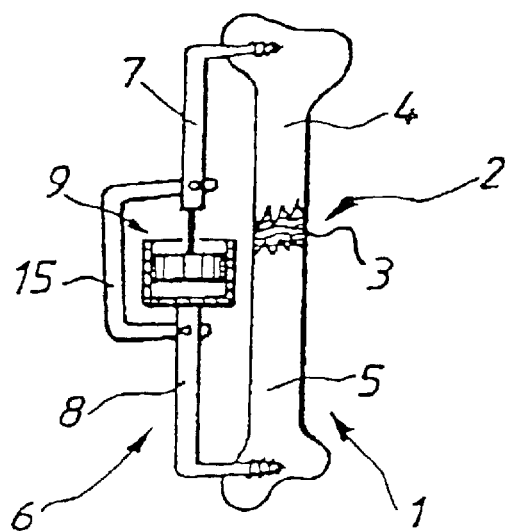
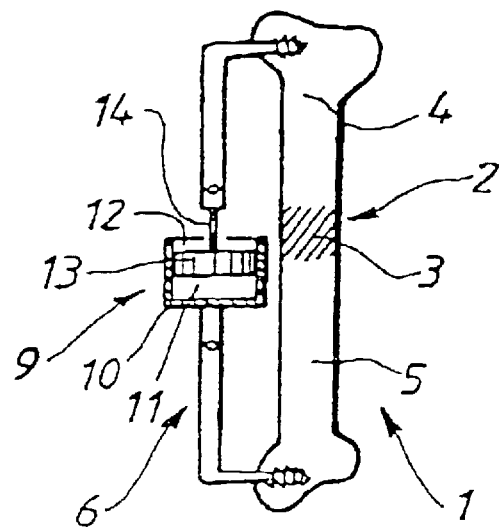
FIG.1a  FIG.1b
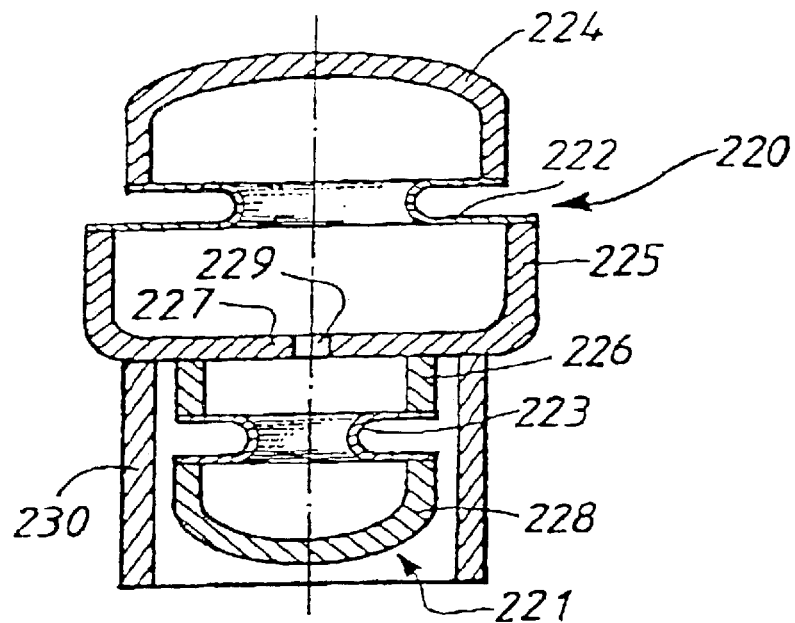
FIG.7

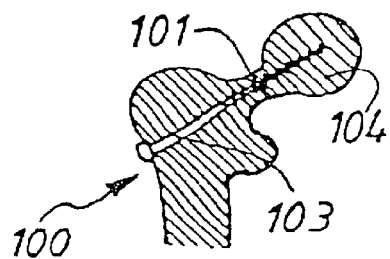
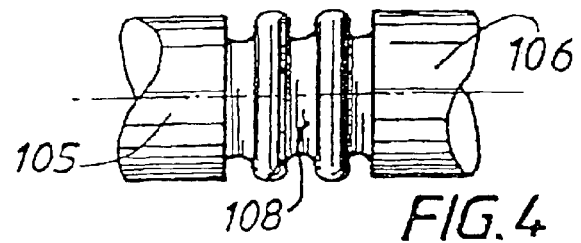
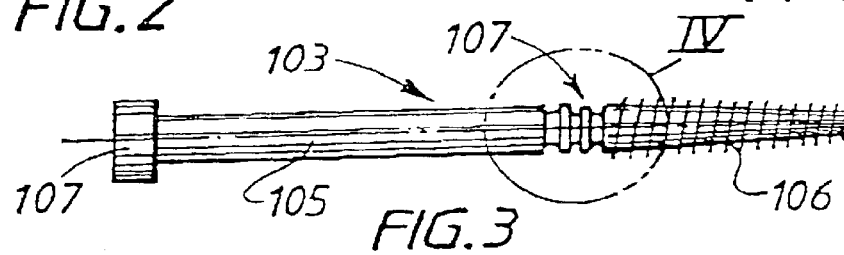
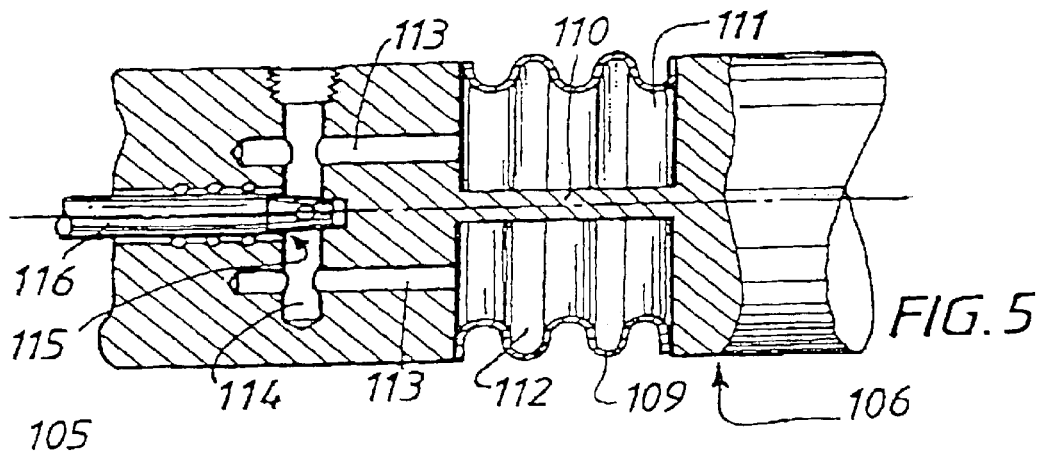
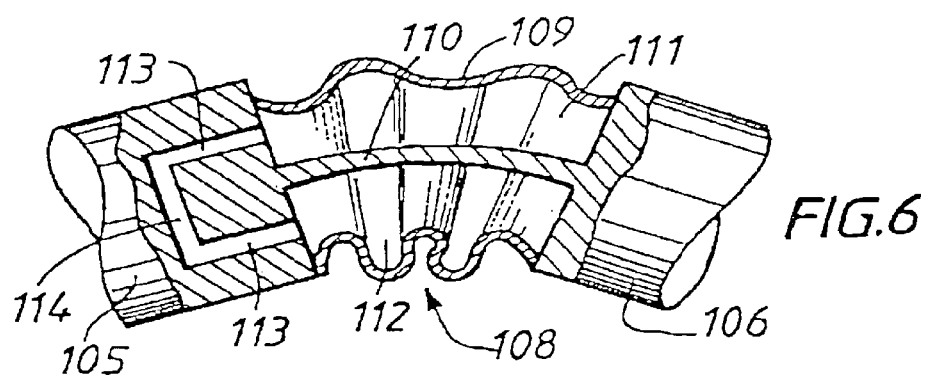

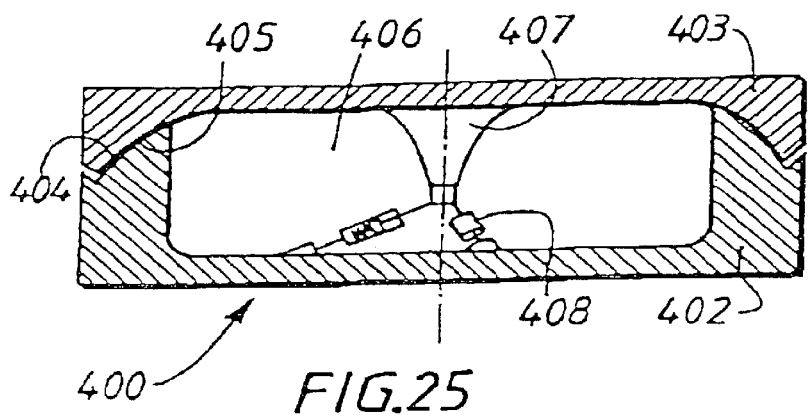
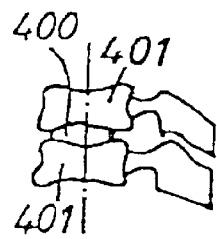
FIG.25    FIG.26
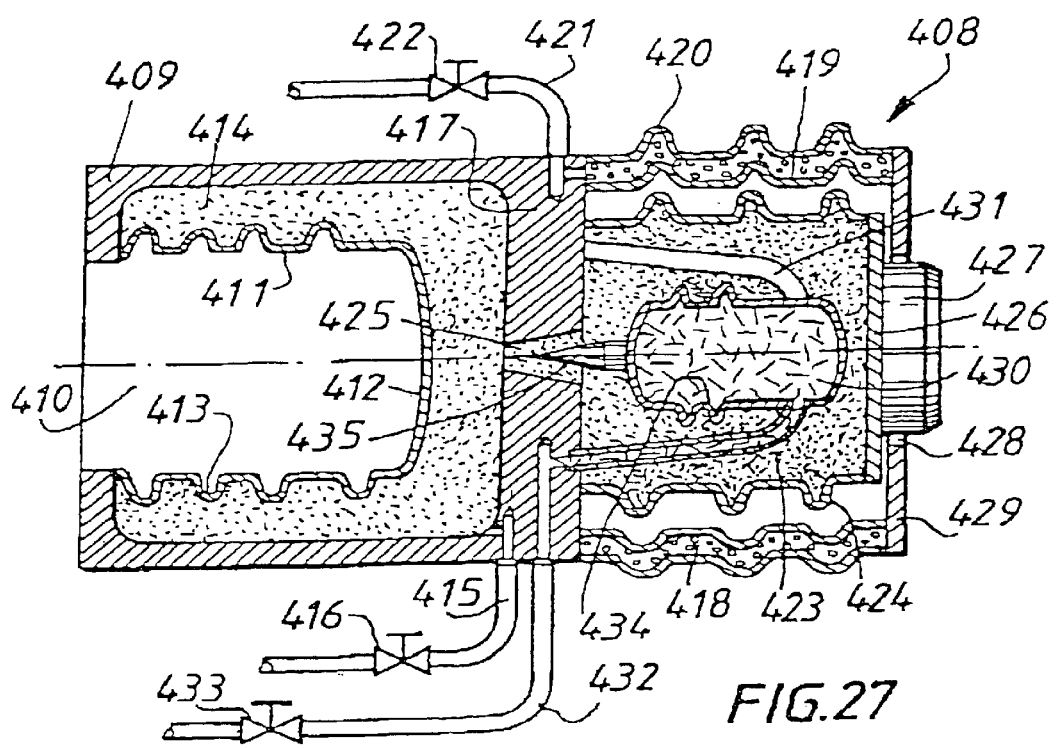
FIG.27

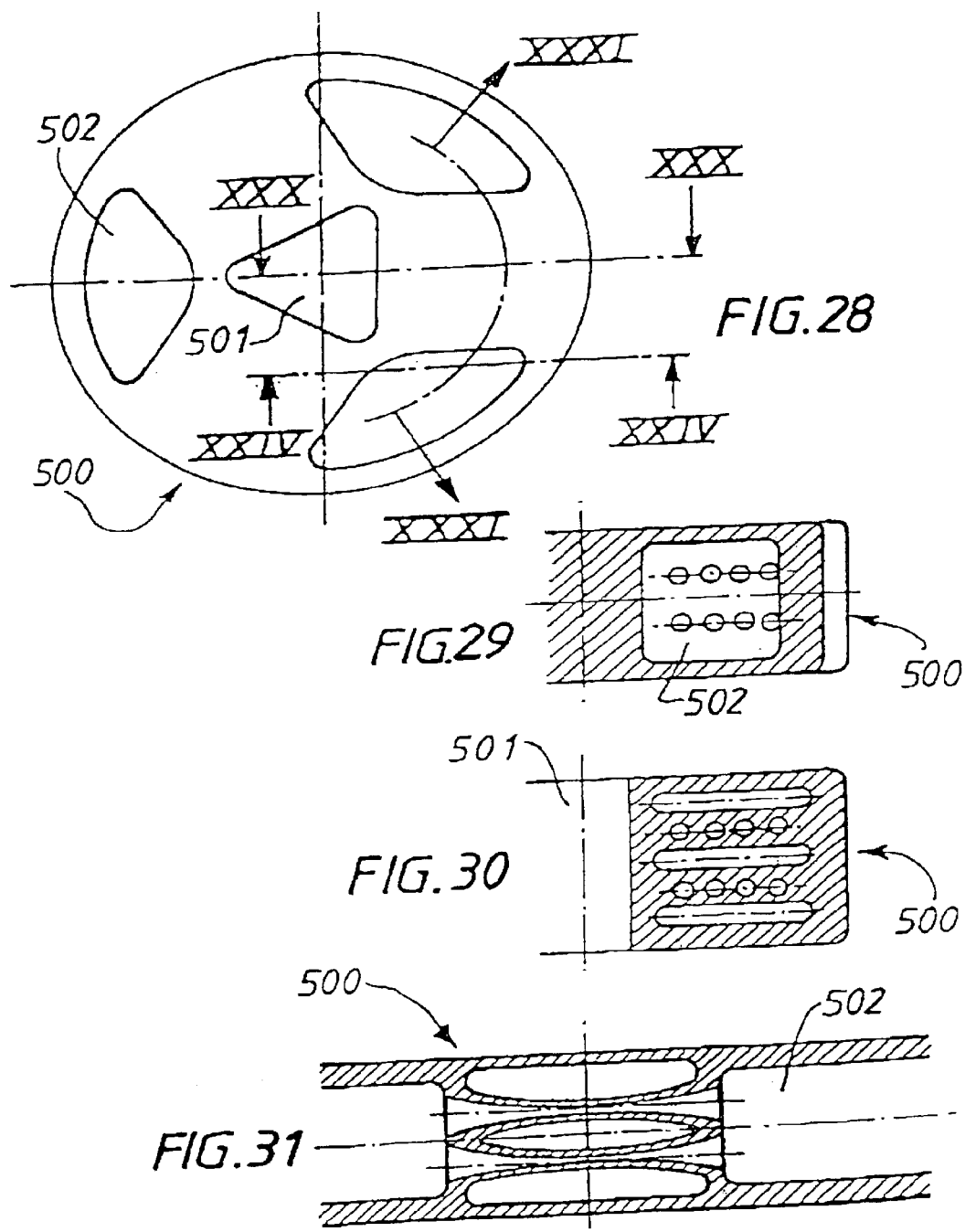

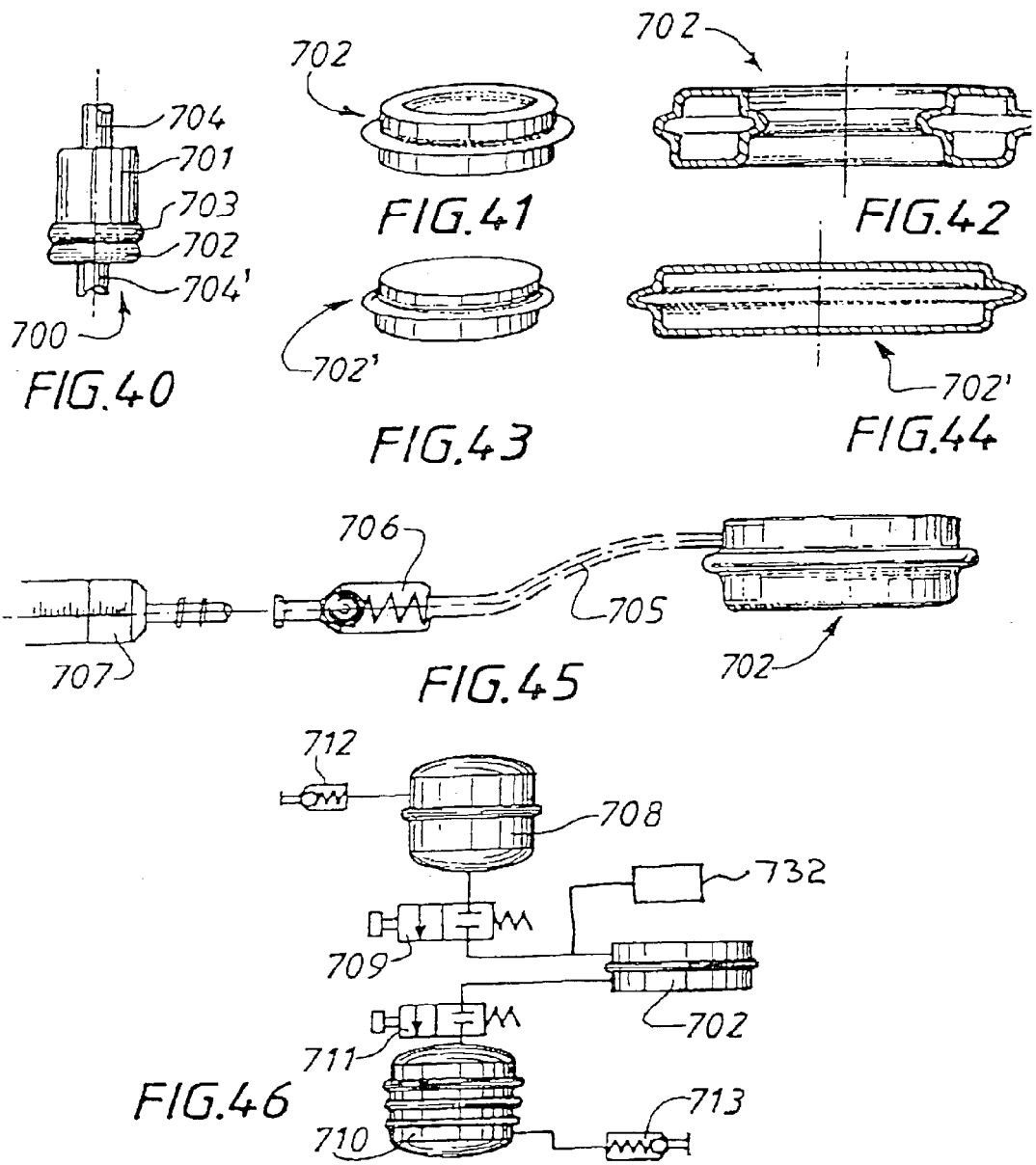

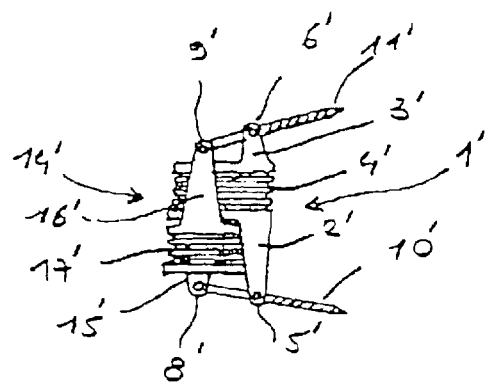
Fig 53
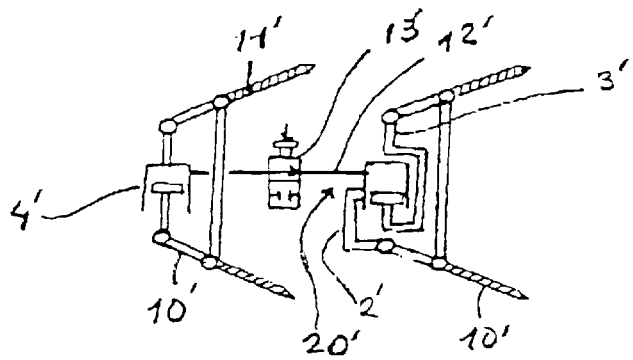
Fig 54
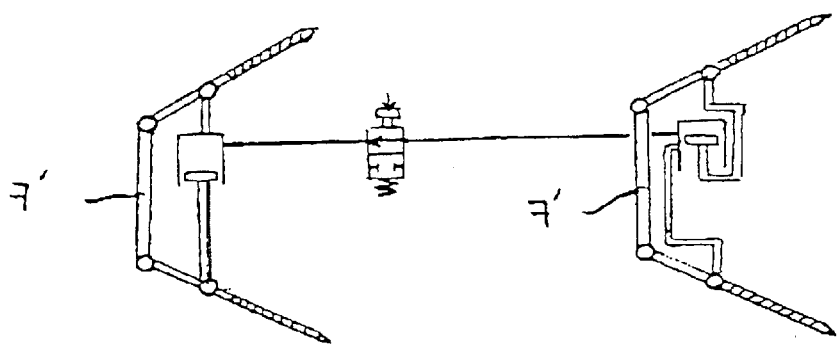
Fig 55
Fig 56
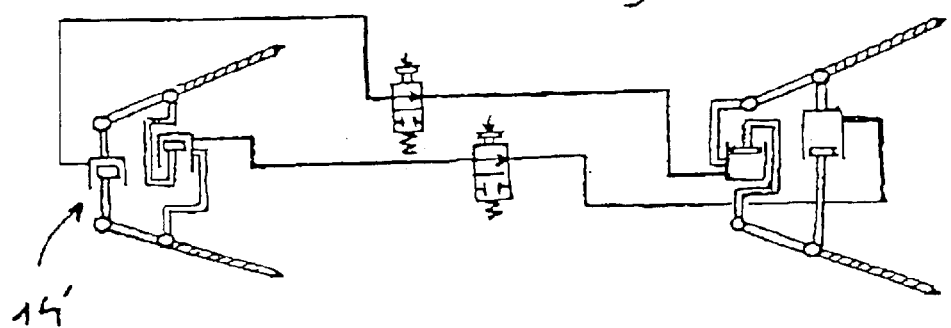

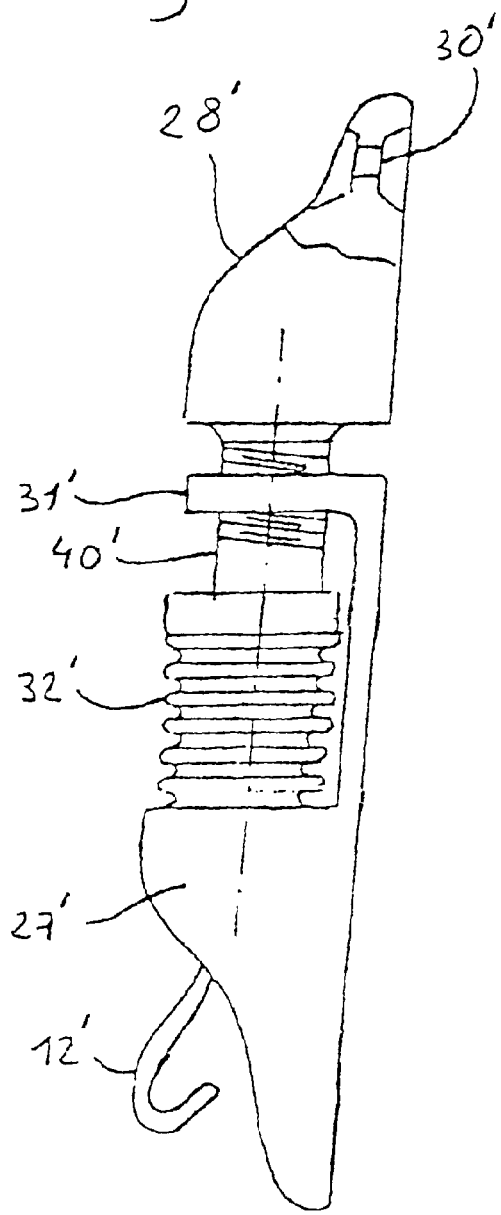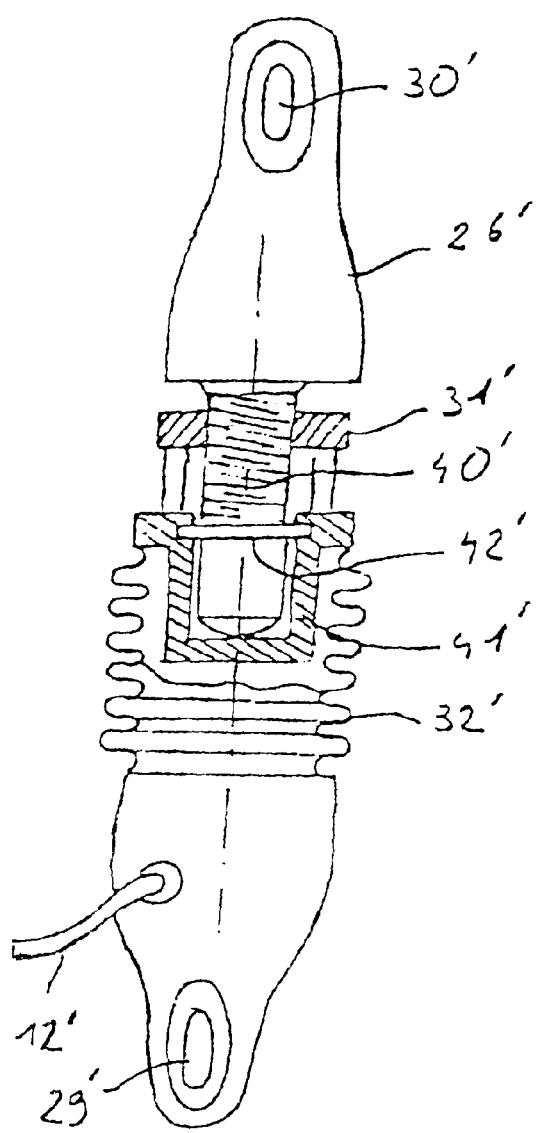

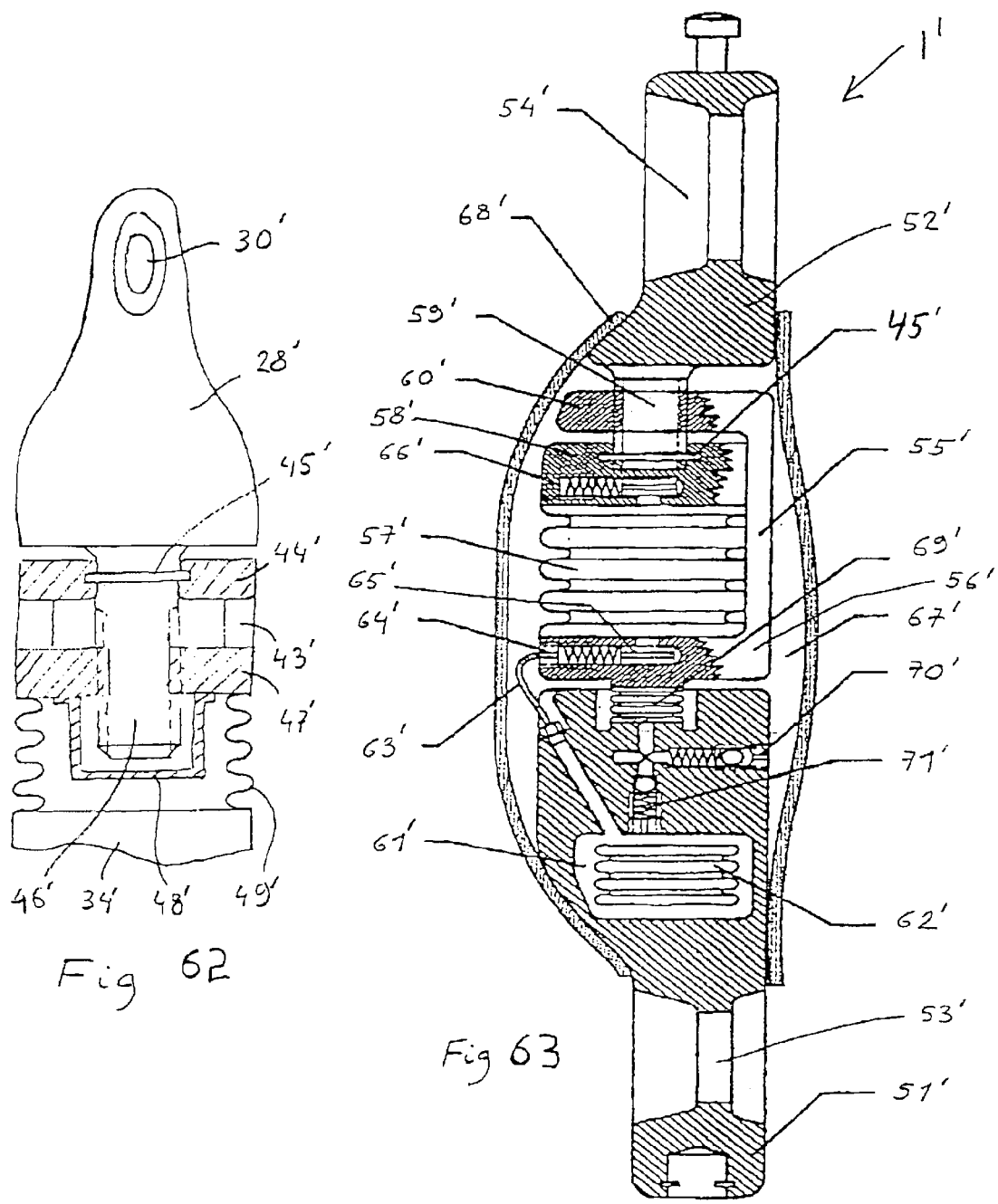

SKELETAL IMPLANT

RELATED APPLICATION

The present application is a continuation of U.S. application Ser. No. 09/200,855, filed Nov. 30, 1998, now abandoned, the disclosure of which is expressly incorporated by reference herein in its entirety. Application Ser. No. 09/200,855 is a continuation-in-part of application Ser. No. 08/897,673, filed on Jul. 21, 1997, now abondoned, the priority of which is claimed under 35 USC 120 and the disclosure of which is incorporated by reference thereto in its entirety. Further, application Ser. No. 08/897,673, claims priority 35 U.S.C. § 119 of French Patent Application No. 9609157 filed on Jul. 22, 1996 and French Patent Application No. 9805549 filed on Apr. 30, 1998, the disclosures of which are hereby incorporated by reference thereto in their entireties.

BACKGROUND OF THE INVENTION

1. Field of the Invention

The present invention relates to a skeletal implant, and more particularly to an implant of this type to be used for connecting at least two elements of the skeleton, which implant is embodied in at least two parts, each of which is capable of being connected to one of these elements.

According to a first aspect of the invention, it relates to a consolidating and/or connecting implant, and more particularly to an implant of this type to be used to consolidate a connection between two bone elements, of the type comprising a first part designed to be attached to one of the elements and a second part designed to be attached to the other element.

2. Background and Material Information

There are known implants of this type that are capable of being used, for example, in the case of a performance of a bone graft or during the formation of a callus following a fracture. The two ends of the implant, which are rigidly connected to one another, for example because they are embodied in one piece, are each attached, for example screwed, to a bone element located on either side of the graft. When the graft has consolidated, the implant can be removed.

However, there are numerous cases where the implant is left in place. This is particularly the case when the implant is used to replace a bone structure which is impossible to restore or to construct.

In such cases, the rigidity of the implant, which is often indispensable at the beginning of the implantation, during the formation of the callus, later constitutes a drawback. In effect, the bone structures no longer sustain sufficient mechanical stress. Therefore, they do not reconstitute themselves in an optimal way, this reconstitution being tied to a satisfactory stressing of the bone, the disturbance of which has consequences which can result in post-surgical pain that is very difficult to treat.

Moreover, when the implant is to be used to connect two bone elements which are normally capable of moving relative to one another, as in the case of a rachidian implant, this rigidity results in a functional handicap in the patient in whom it is implanted, and excessive stress on the neighboring joints.

SUMMARY OF THE INVENTION

The object of the invention is, among other things, to eliminate these drawbacks.

According to a second aspect of the invention, it relates to an articulated implant, and more particularly to an implant of this type intended either to be intercalated between two bone elements in relative motion, such as an artificial intervertebral disk, or to replace a joint or an element of a joint, such as an artificial head of the femur.

As regards the intercalated implant, it can be beneficial to assist the adjacent bone structures and the ligaments during rapid, or even violent movements. On the other hand, it may be preferable to allow these structures and ligaments to work during slow movements or simple static loads in order to prevent atrophy or weakening.

As regards the articulated implant itself, a completely rigid structure fully transmits the shocks and vibrations to the other element of the joint, resulting in a risk of dystrophy or rupture of this other element.

Also, once a surgical skeleton implant is implanted no modification can be made to adapt the implant to the changing needs of the patients.

Another object of the present invention is to eliminate these drawbacks.

To this end, the subject of the invention is a skeletal implant of the type to be used for connecting at least two elements of the skeleton, which implant is embodied in at least two parts, each of which is capable of being connected to one of these elements, there parts being movable with respect to each other, characterized in that it comprises between these two parts at least one adjustable device responsive to non invasive control means, said control means being preferably located on said implant, to exert an adjustable force, for example a distraction or compression force, between said parts, and/or to authorise an adjustable displacement between said parts between a starting position and a displaced position in which said parts should, at least temporarily, be maintained, and/or to secure a damping effect with an adjustable coefficient of resistance.

It is noted, first of all, that the adjustment can be discrete as well as continuous, and for example, can include only two positions of adjustment.

It is known that a shock-absorbing device is a device generally comprising two chambers of variable volume filled with a hydraulic fluid and connected by a calibrated opening. A device of this type is intended to <<cushion>> the movements between two elements, one of which is connected to a structure of one of the chambers, the other being connected to an element in which the calibrated opening is formed.

When the two elements move relative to one another, the volumes of the two chambers vary in inverse proportion to one another, the hydraulic fluid being laminated at the level of the calibrated opening. The result is a force which opposes the relative movement between the two elements which, as will be shown, is proportional to the speed of this movement.

Used within the scope of the invention, a device of this type applied to an implant of the consolidating and/or connecting type has the advantage of allowing the bone structures to function, and thus to develop, in a practically normal way at moderate relative speeds between the bone elements connected by the implant, particularly in the case of static stresses. On the other hand, the greater the relative speeds, particularly in the case of voluntary rapid movement or shock, that is, dynamic stresses, the greater the portion of the stress absorbed by the implant.

The result is that the osteo-ligamentous structure, weakened by the situation which justified the insertion of the implant, can nevertheless function and thus reconstitute normally as long as the stresses remain moderate. But the greater these stresses, the more the natural structure is assisted by the implant.

Moreover, the coefficient of resistance being adjustable, it is possible to reduce it progressively as the bone structure reconstitutes. The latter can also sustain more and more dynamic stresses until, eventually, it returns to normal functioning.

It is noted that it has already been suggested in the prior art to endow prostheses with viscous and/or elastic means intended to absorb shocks. Likewise, it is well known to provide, in certain prostheses, regulating or adjusting means. However, no prosthesis with a functional characteristic of viscous resistance has yet been proposed wherein the coefficient of resistance would be adjustable. This combination is essential in the primary function of the invention, which is to allow a progressive reconstitution of the bone structure and an optimal continuous adaptation to the state of this structure.

When applied to an articulated implant, the invention also makes it possible to give the articulation greater flexibility, which, as in the prior art, allows it to absorb shocks, but in this case also allows the neighboring bone structures and ligaments to work.

Finally, the consequence of this shock-absorbing characteristic is to protect the implant itself, as well as joints located above and below the implant, from shocks.

In one particular embodiment, the implant comprises removable means for locking the shock-absorbing device at a predetermined length.

The implant according to the invention, in this embodiment, can function during a first period in the traditional way, like a rigid implant. This phase of functioning is for example that of the formation of the callus in the case of a graft. During a second period, the locking means are removed and the implant functions according to the invention, exerting between the elements to which it is connected a force which is proportional to their relative speed and is therefore a function of the stresses exerted in the graft.

In another particular embodiment, the implant comprises means for limiting the travel of the shock-absorbing device.

This has the advantage of rendering the implant rigid in the case where the stresses reach a certain limit. Thus, there is no risk of reaching the rupture stress point.

Advantageously, these means for limiting the travel are adjustable.

The travel of the shock-absorbing device can therefore be adapted to the patient and possibly increased progressively as the graft strengthens.

An implant according to the invention can be embodied in the form of an elongated element such as a screw, or a pin such as a coxofemoral prosthesis pin, or even the neck, the body or the head of a femoral prosthesis, comprising two end parts connected by a flexible middle part, the middle part comprising two chambers filled with hydraulic fluid, disposed on either side of a neutral axis and designed such that one of them increases in volume while the other decreases in volume when the implant flexes, these chambers being linked by at least one calibrated conduit.

This embodiment can be used to connect the two parts of a fractured bone to one another, for example the femur at the level of the neck or the diaphysis. The screw is positioned so that its middle part is located at the point of the fracture, with its neutral axis disposed as near as possible to the plane of maximum flexion under stress. Thus, after the formation of the callus, the implant will continue to assist it during sudden efforts, the hydraulic fluid being forced from the chamber whose volume decreases to the chamber whose volume increases, through the calibrated opening. On the other hand, the callus will sustain the static stresses on its own.

More particularly, these end parts can be connected by an elastic wall delimiting these chambers with a peripheral bellows.

As will be seen below, it is often advantageous to add an elastic component to the viscous component of the implant's behavior.

The calibrated conduit can be embodied in the form of borings in at least one of the end parts.

This produces a very compact embodiment that is well suited to the embodiments of the implant in the form of a screw.

Advantageously, a valve is provided on the calibrated conduit.

This valve can initially be closed during the formation of the callus. Thus the implant is perfectly rigid and behaves like a classic screw. The valve is then opened so that the implant functions according to the invention, with its shock-absorbing function. A valve with a progressive opening also makes it possible to provide the function for adjusting the coefficient of resistance.

The control of the valve is preferably housed at the end of the implant, nearest the skin.

Thus, a completely non-invasive intervention allows the valve to be opened and possibly adjusted.

In a particular embodiment which is especially well suited to the performance of a bone graft for the purpose of replacing an injured vertebra, the shock-absorbing device comprises at least one chamber formed of two semi-chambers joined by a bellows, each of the semi-chambers being connected to one of the parts of the implant, this chamber being filled with a hydraulic fluid, and at least one calibrated opening being provided in a wall of this chamber for connecting this chamber with another chamber.

This disposition has the advantage of being very compact and preventing the relative slippage of the mechanical parts, with the resulting risk of hydraulic fluid leakage. However, in certain cases a traditional cylinder-and-piston shock-absorber may be preferred.

More particularly, these semi-chambers can be in the form of cupels whose openings face one another.

The above-mentioned locking means can in this case comprise a removable elongated locking element, inserted into a fold of the bellows so as to prevent it from collapsing.

The elongated locking element can be embodied in any appropriate way, for example in the form of a metal beaded chain.

The above-mentioned means for limiting the travel can comprise a stop ring screwed onto one of the semi-chambers and designed to cooperate with a shoulder of the other semi-chamber to prevent the two semi-chambers from moving toward one another beyond a certain limit.

The other chamber can be housed in a supporting skirt mounted on one of the semi-chambers around the calibrated opening, opposite the other semi chamber.

This other chamber can also be formed of two semi-chambers joined by a bellows.

In a preferred embodiment, the implant according to the invention also includes elastic means between these two parts.

In effect, it is often beneficial for the resistance to the relative displacement of the two parts of the implant to be proportional not only to the speed of this displacement, but also to the value of this displacement itself relative to a nominal position. Thus, the implant's assistance to the surrounding bone structures is even more efficient when they are farther apart than in their normal configuration.

Advantageously, the coefficient of elasticity is adjustable.

Thus, it is possible to adjust the elasticity of the implant and, for example, to render it increasingly flexible as the surrounding structure re-establish themselves.

This type of elasticity can be obtained in an implant comprising two chambers filled with hydraulic fluid and joined by a calibrated opening, at least one of which chambers contains a compression ampulla at ambient pressure with elastic walls.

When a movement between the two parts of the implant begins, it produces a pressure variation in the chambers, and thus an elastic reaction of the compressible ampulla.

The wall of this ampulla can have progressive elasticity, one of the chambers being capable of being joined to a source of fluid under pressure.

Thus, in this case, it is possible to regulate the elasticity of the implant by adjusting the pressure in the cambers.

Means can be provided for adjusting the cross section of the calibrated opening.

In particular, these means for adjusting the cross section of the calibrated opening can comprise a hydraulically controlled needle valve.

Another subject of the present invention is an implant of the type described above wherein the shock-absorbing device comprises at least two chambers, specifically two low-pressure chambers whose wails are made of elastic material, these chambers being jointed by at least one calibrated conduit and filled with hydraulic fluid, and designed to sustain a differential pressure variation during a relative movement of the elements.

This type of design makes it possible to easily obtain implants which, as above, not only have a viscous resistance which is a function of the speed, but also an elastic resistance which is a function of the displacement.

In this case, the cross-section of the conduit can advantageously be determined by the prevailing pressure in a high-pressure chamber which is capable of compressing this conduit.

As a result of this design, the coefficient of resistance of the implant can be regulated very easily by adjusting the pressure in the high-pressure chamber.

In particular, one of the low-pressure chambers can have a wall of relatively low rigidity relative to the rigidity of the walls of the other chamber.

This design allows the implant to function even when the two chambers are not stressed differently. During a movement which creates excessive pressure, the pressure increases more in the rigid-walled chamber, resulting in a flow of the hydraulic fluid from this chamber to the chamber with the less rigid wall, and thus a shock-absorbing effect.

In one particular embodiment, a high-pressure chamber and a low-pressure chamber can be connected, in the low-pressure to high-pressure direction, by a non-return valve.

As will be seen, this disposition makes it possible to increase the pressure difference between the high-pressure and low-pressure chambers. It also makes it possible to maintain this difference despite possible leaks in the high-pressure to low-pressure direction.

The anti-return valve can comprise a flexible tube connected to the low-pressure chamber, one free end of which is inserted into a free end of a tube connected to the high-pressure chamber.

This type of valve is very small and also has the advantage of being even more tightly closed when the pressure difference is greater.

Preferably, it is also arranged for these chambers to be connected by a pressure regulation valve in parallel with the anti-return valve.

It will be seen that the anti-return valve is preferably disposed between the high-rigidity, low-pressure chamber and the high-pressure chamber.

In one particular embodiment, the implant according to the invention comprises a first annular low-pressure chamber, and a second rotating chamber in the center of the first chamber, the calibrated conduits being formed radially in the wall separating the two chambers.

Advantageously, the outer wall of the first low-pressure chamber is relatively thin, and the wall separating the two low-pressure chambers if relatively thick.

This implant can comprise at least one annular high-pressure chamber formed within the thickness of the wall separating the two low-pressure chambers, and designed to compress the calibrated conduits.

In another embodiment, this conduit is at least partially embodied in the form of a tube of elastic material surrounded by a tube that is substantially more rigid, these tubes being joined into rings at their ends, the compressed volume between the two tubes forming a high-pressure chamber.

In another particular embodiment, the implant is substantially disk-shaped, comprising a plurality of low-pressure chambers in sectors, joined by the calibrated conduits, which alternate inside the thickness of the disk with the high-pressure chambers.

Advantageously, the implant according to the invention comprises means for adjusting the distance between the elements it connects.

This type of design makes it possible, in particular, to alleviate possible post-operative pain by adjusting this distance appropriately. It is also particularly advantageous in the case of prostheses intended for children who are still growing.

These adjusting means can comprise a bellows designed to receive a hydraulic fluid, and means for connecting this bellows to a source of fluid under pressure.

Another subject of the invention is a pair of implants as described above, the low-pressure chamber of each of the implants being connected by the anti-return valve to the high-pressure chamber of the other implant.

A pair of implants of this type can particularly be provided, in the case of a graft of the vertebral column, to assist the graft in case of lateral flexion.

More generally, a pair of implants according to the invention can include means for automatically adapting to the movements of the wearer of the implants.

Up to this point, bone consolidation implants embodied according to the invention have been described. It will now be shown that the invention is also well suited to the embodiment of articulated implants.

In this case, each part of an implant as described above is articulated to the other.

More particularly, these parts can have complementary surfaces which rest against one anther, forming a ball-and-socket joint.

An articulated implant of this type can include, in particular, a pivot integral with one of the parts and housed in a space formed between a plurality of low-pressure chambers in the form of sections, which are integral with the other part of the implant and joined by the calibrated conduits, which themselves alternate with high-pressure chambers.

These embodiments are suitable as intervertebral disks.

In a particular application to a coxofemoral joint, the implant according to the invention comprises an articulating hollow sphere whose wall is open so as to allow the insertion of the end of a connecting pin, the shock-absorbing device being disposed inside this sphere between the wall of the latter and the end of the connecting pin.

More particularly, this shock-absorbing device can comprise an end element of the connecting pin designed to slide through a slot of a partition inside the sphere, which partition delimits two chambers in the sphere, and at least one calibrated opening is formed inside this end element between the two chambers.

In another embodiment, this shock-absorbing device can include an end element of the connecting pin disposed between two shock-absorbing elements, each of which includes at least two low-pressure chambers whose walls are made of elastic material, these chambers being connected by at least one calibrated conduit and filled with hydraulic fluid, and designed to sustain a differential pressure variation during a relative movement of the sphere and the connecting pin.

Another subject of the invention is a pair of implants as described above, used particularly within the scope of an arthrodesis of the vertebral column, each of the implants being mechanically connected in series to a connecting pin of a known type.

More particularly, each of the implants can include means for adjusting the distance between the two elements it connects.

It is thus possible, using a pair of implants of this type, not only to perform the arthrodesis, but also to adjust the angle and the distance between the two parts of the vertebral column connected by the prosthesis.

In one particular mode of embodiment, these adjusting means include, for each implant, an expandable element such as a bellows, designed to receive a hydraulic fluid, and means for connecting this bellows to a source of fluid under pressure.

This source of fluid under pressure can comprise a high-pressure fluid reservoir.

Advantageously, this high-pressure reservoir is common to both implants, each expandable element is also connected to a low-pressure reservoir, and an expandable refill cell is mechanically connected in series to each pin, each refill cell being connected to the high-pressure and low-pressure reservoirs by two anti-return valves, one of which allows a flow of fluid from the low-pressure reservoir to the refill cell, the other allowing a flow of fluid from the refill cell to the high-pressure reservoir.

It will be seen that this type of design makes it possible to produce a pump activated by the movements of the wearer of the implants.

In another particular embodiment, the above-mentioned pair of implants if formed of implants in which the shock-absorbing device comprises at least two chambers, these chambers being connected by at least one calibrated conduit and filled with hydraulic fluid, and designed to sustain a differential pressure variation during a relative movement of these elements, the cross-section of this calibrated conduit being determined by the prevailing pressure in a high-pressure chamber, and the high-pressure chambers of the implants are connected to the high-pressure reservoir by a controllable valve.

Another subject of the invention is a skeletal implant as described above, specifically belonging to a pair of implants, which includes sensors of physical quantities, including pressure, supplied with electric power and controlled from outside the body in a non-invasive way, and designed to transmit their information to display means.

More particularly, this implant can also include adjusting actuators which are also supplied with electric power and controlled from outside the body in a non-invasive way.

In facts the implants which were described have a variable length or dimension, the two parts or ends of the implant being able to move apart from one another or approach one another actively and/or passively, for example along the longitudinal axis of the implant, by virtue of the interposition of a deformable element, for example a hydraulic element, control means and/or regulating means being provided so as to make it possible to obtain a change in dimension of the implant in order to modify the distance between the two bone elements and/or to ensure an adjustable viscous or viscoelastic damping permitting a slow movement between the two bone elements and also counteracting a more abrupt displacement.

If necessary, a sufficiently high hydraulic pressure can be maintained by using the effect of a mechanical pump, actuated by the movements of the body, with a pressure-limiting valve flap, cooperating with a low-pressure reservoir.

For example, double implants consisting of two individual implants can be disposed respectively on either side of the spine in order to connect two vertebrae, each of the two elements thus being fixed to a lower vertebra via an anchoring means, such as a pedicle screw, and to an upper vertebra, either adjacent or more distant, likewise each time by an anchoring means, such as a pedicle screw.

In the case of a double implant consisting of two individual implants acting on the same skeletal structures, the two individual implants hydraulically can be interconnected in such a way as to permit pivoting movements of the bone elements relative to one another, namely a lateral pivoting in the frontal plane of the spine, by increasing the length of one of the individual implants and concomitantly reducing the length of the other implant, for a correction of deformation and/or a damping of lateral flexion.

By virtue of control means, for example noninvasive means of the magnetic type, it is possible to effect the desired modifications to the dimension of the individual implants and/or the modifications to the damping coefficient of the element acting as a damper. Moreover, means can be provided for automatically modifying the damping coefficient or the viscosity as a function of the movements of the body.

In brief, the present invention proposes realizing and perfecting an implantable device comprising at least one implant equipped with two end parts which can be fixed, by anchoring means, on at least two elements or parts of the skeleton, and comprising means of displacement, preferably at least partially reversible, between the said two ends, these means being arranged to provoke and/or maintain a displacement between the said elements of the skeleton.

This displacement can be a rectilinear and/or curved displacement, for example it can be a displacement of elongation, also called distraction, or a displacement of shortening, called compression, or a displacement in rotation, it being possible for this rotation to be isolated or, on the contrary, to be combined with a distraction or a compression.

In the simplest embodiment, in which the said displacement means are capable of maintaining but not provoking the displacement, these displacement means are controlled by control means, preferably noninvasive ones, which make it possible to release them so as to allow the patient, or another party, to modify the relative position of the two portions or elements of the skeleton, after which the said control means are actuated in order to block the implant in this new position, an inverse or reversible displacement still remaining possible if one acts once more on the control means, for example in the case where the displacements would have been too great.

In another preferred embodiment of the invention, the said displacement means include a motor means with which it is possible to impose a displacement between the said ends by exerting a force between them.

In a particular embodiment, this force can be exerted temporarily, that is to say for quite a brief instant, far the purpose of provoking a therapeutically desirable displacement between the two portions or elements of the skeleton, such a displacement often being intended for a small amplitude, since it is rapidly impeded by the anatomical structures which must not be traumatized. At the end of this instant, the control means make it possible to block the two ends relative to one another and to maintain the implant in its new position.

In another embodiment, by contrast, the said displacement means are capable of exerting an anatomically active permanent force between the said two ends, it being possible for this force to be constant or variable in such a way as to exert on the anatomical environment a stress which will gradually permit an anatomically desired displacement between the said two portions or elements of the skeleton, these motor means being controllable by control means with which it is possible to permit or interrupt their functioning and/or to adjust the intensity of the force.

If appropriate, the implant can also include viscous or viscoelastic damping means which can be used when the implant is blocked in its dimension or when the implant is freed or when it exerts its permanent active force. Such means have been described in the abovementioned European and American applications.

The said means of displacement and, if necessary, the said motor means can be of the hydraulic and/or mechanical and/or electrical type, a hydraulic type being preferred.

In one embodiment using hydraulic means, the implant preferably includes: two parts or end elements, for example rods, each receiving at least one means for anchoring in a skeletal part; at least one deformable element, preferably hydraulic, interposed between the said two elements, and permitting a variation in dimension and/or the creation of an active force between them; preferably at least one high-pressure reservoir, called a reserve, with which it is possible to address the high pressure, on demand, to a functional user circuit; preferably at least one low-pressure collection reservoir connected to the high-pressure reservoir via a pressure control valve; preferably at least one circuit for recharging the high-pressure reservoir, comprising at least one deformable element, preferably sensitive to physical positions or movements of the body receiving the implant; to generate a high pressure which, if so required, feeds the high-pressure reservoir; at least one functional circuit, namely: a circuit for modifying the dimension, for example the length, of the implant, comprising the said deformable element with which it is possible to modify a dimension between the two end elements and/or to establish, between the two end elements, an active force capable of provoking a progressive modification of the dimension between the said end elements, the said deformable element being connected on the one hand to the high-pressure reserve reservoir by way of a first valve and, on the other hand, to the low-pressure collection reservoir by way of a second valve in order to make it possible, as a function of the control of the said valves, to increase and/or reduce the dimension of the said deformable element in order to permit or provoke a lasting modification to the said dimension of the said individual implant, and/or a viscous or viscoelastic damping circuit comprising: if appropriate, an elastic element surgically interposed between the said two end elements of the implant, and a hydraulic damping element comprising at least one deformable element sensitive to the speed of a dimensional variation of the implant and communicating with a discharge reservoir by way of a throttle means, and control means which can preferably be actuated from outside the body of the patient, in order to modify the dimension of the implant and/or the force exerted by the implant and/or the damping properties.

Of course, one and the same piece, for example a deformable element, can form a constituent part of several of the constituents defined hereinabove.

The circuit for recharging the high-pressure reservoir is in fact intended to act as a very high-pressure pump, making it possible to establish and to maintain a high pressure in a high-pressure reservoir Preferably, especially in the preferred case where the deformable element of the high-pressure recharging circuit is sensitive to physical positions or movements of the patient receiving the implant, this deformable element has a small surface compared with the active surface of the element which transmits to it the force originating from the body, in such a way as to ensure a pressure-multiplying differential effect, it being understood that upon each stress only a small quantity of very high-pressure fluid is sent towards the high-pressure chamber.

The deformable element of the circuit for recharging the high-pressure reservoir can also be actuated by external means while remaining implanted. Thus, for example, this deformable element can be in the form of a pump, preferably formed by a metal bellows, implanted on a part of the body at a point where an external pressure can be applied to it, for example implanted on the posterior face of the sacrum, allowing this pump or bellows to be actuated by hand via the external anatomical planes.

Alternatively, this pump could be of the magnetic or electromagnetic type, having, for example, a movable core actuating a small piston or bellows under the influence of an electromagnetic force of external origin.

It will also be appreciated that the present application incorporates the alternatives and equivalents using non-hydraulic motor and/or damping means, ensuring the same functions of lasting and adjustable modification of dimension and/or force and/or adjustable modification or variation of the damping coefficient.

Solely by way of example, an implant of the uniquely mechanical type can comprise a first end, movable in translation relative to the second end, and secured to a rod which is immobilized by a catch which is sensitive to an external magnetic control means for blocking or releasing the said rod, a motor means being interposed between the said rod and the said second end, it being possible for this motor means to be in the form of a spring or another precharged elastic element tending to displace one of the ends relative to the other when the catch is released, it being possible for the movement to be reversible, at least once, for example by inserting, between the spring and the said second end, a spring support piece which can be displaced, by virtue of other magnetic control means, in such away as to at least partially relax the spring. Alternatively, the implant can include several springs arranged in parallel and capable of being used separately by release means which are sensitive to control means.

In another embodiment, an implant can include displacement means of the electromagnetic type, for example a solenoid with a plunger core, the solenoid being secured to one of the ends of an implant and the plunger core being secured to the other end, blocking means preferably being provided for immobilizing the core relative to the solenoid in at least two different positions, the solenoid being capable of being powered, via a control means, from an electrical energy source, for example an implanted battery and/or an accumulator which can be recharged by antenna transmission with transcutaneous coupling.

Such embodiments are reversible within the meaning of the invention because, if so desired, they permit a modification in the opposite direction, at least partially, of the dimensional modification which has been established.

The present invention also makes it possible to perfect the movements or forces of rotation permitted or imposed by an implant or a set of at least two individual implants in the frontal and/or sagittal and/or horizontal plane.

For example, the invention can provide implants of this type with which it is possible to impose symmetrical movements of rotation, that is to say in the same direction and of the same value of rotation, of the pedicle screws or similar anchoring means of the two individual implant parts, or, by contrast, antisymmetrical movements, that is to say in opposite directions, or else independent of one another.

Generally speaking, the movement or force of rotation controlled between the two anchoring means of an implant according to the invention and, where appropriate, the coordination of the movements or forces of rotation of the anchoring means of several implants, for example the individual implants of a double implant, will make it possible, depending on requirements, to approximate much more closely the theoretically possible or desirable natural movement between the two bone parts to which the anchoring means are fixed, so as to impose progressive displacements, for example for corrections, and/or progressively modifiable damping, ranging, for example, from rigidity during a phase of bone consolidation or healing to progressive mobility, making it possible, for example, to safeguard a joint.

The skeletal implant has a first and a second part or end element, means for anchoring in bone parts, which means are connected respectively to the said first and second end elements, at least one deformable element connected respectively to the said first and second anchoring means, and means permitting a nonrectilinear movement, particularly a rotation, between the said anchoring means.

The implant can include means permitting a rotation between the said end elements.

The said deformable element can be deformable in rotation.

The implant can include means permitting a rotation of at least one of the said anchoring means relative to the end piece to which it is connected.

The abovementioned movement of rotation can also be combined with movements of translation, in such a way that the resulting movement can be a complex nonrectilinear displacement.

According to one refinement, the skeletal implant, having a first and a second end element, means for anchoring in bone parts, for example by way of screws, such as, for example, pedicle screws situated at the said ends, at least one deformable element, for example a hydraulic element, containing an incompressible hydraulic fluid and interposed between the two end elements, and means for actuating the deformable element, for example, if necessary, hydraulic circuit means connected to the said at least one deformable element interposed between the said ends, and capable of permitting a lasting modification, preferably obtained progressively, of the distance or the force between the said two ends and/or a viscoelastic damping of the movements between the said two ends, the said actuating means, for example the said hydraulic circuit means, being sensitive to control means which can preferably be actuated from outside the body of the patient, is characterized in that the said fixing or anchoring means are fixed to the said two ends by articulated attachment means, and in that the said fixing or anchoring means are additionally connected to one another via a rigid joining element which is relatively parallel to the geometric axis connecting the said two ends of the implant and is situated at a certain distance from the said axis, by attachment means which are likewise articulated, for example in such a way as to form between the said four attachment points a deformable quadrilateral, permitting an angular movement of rotation of the said fixing or anchoring means relative to one another.

These articulated attachment means can consist of actual mechanical articulations or of suitably deformable joining means.

For example, the articulations can be articulations using a ball which is received rotatably in a seat of the end piece, this ball having a passage through which it can receive and hold a part of an anchoring means, such as a pedicle screw. Of course, all other articulation principles such as a pivot articulation can be used.

In one embodiment, the said joining element is situated between the axis of the implant and the bone elements to which the implant is fixed, but in another embodiment the said joining element is arranged on the other side of the axis of the implant in relation to the bone elements which are joined by the implant.

The said joining elements can be simple rigid links such as rods or bars of invariable length.

However, in another embodiment, these joining elements themselves can include, between their ends, at least one deformable zone, which then makes it possible to effect displacements, such as, for example, an elongation of the implant without relative rotation of the fixing means, by simultaneous modification of the length of the actual element and of the joining element, and/or to effect a viscoelastic damping between the bone elements without any movement of rotation of the said fixing means.

A complex implant in accordance with the invention can be formed by using two individual implants arranged, for example, side by side, for example on either side of the spinous processes of the vertebral column, with a hydraulic interconnection making it possible to effect at least one of the following functions: antisymmetrical rotation movement of the means of one individual implant relative to the movement of the anchoring means of the other implant, symmetrical movements of the said anchoring means, independent movements.

Of course, for the sake of simplicity, the two individual elements of a complex implant can use common hydraulic elements, such as, for example, high-pressure reservoir, low-pressure collector, means for creating the high pressure, and means for controlling the hydraulic circuit.

In another embodiment, intended to permit a rotation in a transverse plane, or, if appropriate, an oblique plane, relative to the general direction of the implant, that is to say the direction connecting the two anchoring means or screws, the skeletal implant, having a first and a second end element, means for fixing or anchoring in bone parts, for example by way of screws, for example pedicle screws situated at the ends, at least one deformable element interposed between the two end elements, and its actuating means, to permit a lasting modification, preferably obtained progressively, of the distance between one end and an element movable relative to the said one end, and control means, which can preferably be actuated from outside the body of the patient, is characterized in that the said movable element is arranged to provoke or permit a rotation of the other of the two ends about an axis substantially parallel to the said implant.

The means by which the displacement of the said movable element by the movement of the deformable element transforms this movement into a movement of rotation of the said other end, and of the fixing or anchoring means which it supports, can be a means combining a screw and a nut in such a way that the movement of translation of the one provokes a movement of rotation of the other.

In a particular embodiment, the deformable element is interposed between the two end pieces, one of which is capable of turning, in such a way that the deformation of the deformable element entrains at one and the same time a rotation and a translation of one of the end elements, and thus of the anchoring means which it bears, relative to the other end piece, translating into a helical movement of one of the end pieces relative to the other.

In another embodiment, the two end pieces can be secured to one another in such a way as to remain spaced apart by an invariable distance, the movable element then being interposed between this assembly of end elements and the means for transforming the deformation of the movable element into a rotation of one of the end elements relative to the other.

In another embodiment, it is the deformable element itself which is constructed to deform in rotation, for example by using a deformable chamber with rotary piston, according to the well-known principles of hydraulic rotation.

Devices capable of rotation, such as have just been described, can be particularly useful in cases of severe scoliosis or serious degenerative destabilization of the spine. In these cases, it will for example be possible to fix two devices according to the invention on either side of the posterior process of the vertebra, between two vertebral levels, and to provoke rotation between the two anchoring points of one of the two devices, or a rotation combined with a longitudinal displacement, the other device then being capable of a complementary movement of geometric adaptation of the displacements imposed by the first one.

All kinds of complex nonrectilinear displacements can be obtained by means of the intervention, for example by subjecting the displacement of an anchoring means, or of an end piece, to a cam or slide or other curved guide.

The implant consisting of a device according to the invention will preferably have an external shape suitably adapted to the physical environment in which it is located. For example, in particular for vertebral implants, it will be advantageous to give each of the two ends a streamlined shape so as not to disturb the adjacent tissues, especially since, by virtue of the implants according to the invention, it is possible to achieve a functional improvement which should involve the muscles and ligaments, in contrast to arthrodeses which cause their atrophy.

This streamlined shape can comprise an envelope, which is preferably deformable and is applied around the implant, and of which the two ends which having the fixing means for the anchoring means emerge from the envelope, the latter containing the various other components of the implant. The free internal volume in this envelope can preferably serve as a low-pressure liquid reservoir. The implant preferably includes, inside this envelope, the movable element which can be a mechanical motor or preferably a hydraulic motor, for example a hydraulic bellows, the interior of which is connected via a low-pressure valve to the low-pressure volume formed in the envelope.

Preferably, the interior of the envelope also includes a high-pressure reservoir, preferably a bellows, and, again preferably, a differential deformable element for sending liquid at very high pressure into the high-pressure reservoir, the high-pressure reservoir being connected to the moveable element likewise via a high-pressure valve, the high-pressure valve and the low-pressure valve preferably being relatively spaced apart from one another in order to easily permit a selective control by external control means, such as, for example, magnets.

However, in another embodiment, particularly when a succession of individual implants is provided at various levels of the spine, it is also possible to provide a single high-pressure reservoir and/or a single recharging means for recharging the high-pressure reservoirs, which is situated away from the various individual implants and is connected to these by inextensible conduits.

The high-pressure reservoir can advantageously be designed to maintain the liquid which it contains at high pressure, even when significant quantities of this liquid are sent to the motor means of the implant, provoking a substantial reduction in the volume of liquid. This can be effected, for example, by designing the high-pressure reservoir in the form of an elastically deformable reservoir of great stiffness, for example a metal bellows of great stiffness, which is expanded when it contains the liquid at high pressure, this bellows tending to retract in order to maintain the high pressure during a substantial part of its retraction travel. Alternatively, or in combination with such a bellows, it is also possible, in order to maintain the high value of pressure in the reservoir, to provide an energy accumulator in the form of a cell with an elastically deformable wall which is compressed, thus reduced in volume, when the high-pressure liquid is introduced into the high-pressure reservoir, and which relaxes elastically while at the same time maintaining a high pressure when liquid is withdrawn from the high-pressure reservoir. This energy accumulator is preferably in the form of a deformable capsule which can, for example, comprise in its interior an easily deformable substance or a gas, but which particularly preferably has a substantial vacuum so as to eliminate any risk of escape of gas.

The invention also provides for a skeletal implant of the type to be used to connect at least two elements of a skeleton, wherein the skeletal implant comprises a first part adapted to be connected to at least one of the at least two elements of the skeleton, a second part adapted to be connected to another of the at least two elements of the skeleton, a variable volume element adapted to move the first and second parts with respect to each other, a high-pressure chamber supplying fluid to the variable volume element a low-pressure chamber receiving fluid from the variable volume element and a recharging variable volume element is adapted to communicate with the high-pressure chamber and the low-pressure chamber.

The implant may further comprise another variable volume element disposed in the high-pressure chamber.

The implant may further comprise a high-pressure valve allowing fluid to enter the variable volume element from the high-pressure chamber.

The low-pressure chamber may comprise a deformable impermeable sleeve.

The implant may further comprise a low-pressure valve allowing fluid to exit the variable volume element and enter the low-pressure chamber.

The implant may further comprise a third part having one end coupled to the first part and another end disposed between the variable volume element and the second part.

The variable volume element may comprise one end coupled to the first part and another end coupled to a third part.

The implant may further comprise a third part having a threaded opening which engages a threaded portion of the second part.

The recharging variable volume element may comprise one end that is coupled to a third part and another end that is coupled to the first part. The second part may be rotatably coupled to at least one of the variable volume element and the third part.

The implant may further comprise a sealed bellows disposed in the high-pressure chamber.

The recharging variable volume element may be a metal bellows having one end coupled to the first part and another end coupled to a third part.

The implant may further comprise a sleeve defining a variable volume of the low-pressure chamber.

The implant may further comprise a high-pressure conduit connecting the variable volume element to the high-pressure chamber.

The variable volume element may comprise a metal bellows. At least one of the first part and the second part may comprise an opening which is adapted to receive a connecting member, whereby the connecting member connects the first or second part to one of the at least two elements of the skeleton.

The invention also provides for a skeletal implant of the type to be used to connect at least two elements of a skeleton, wherein the skeletal implant comprises a first part adapted to be connected to at least one of the at least two elements of the skeleton, a second part adapted to be connected to another of the at least two elements of the skeleton, a variable volume element having a first end coupled to the first part and a second end, the variable volume element being adapted to move the first and second parts away from each other, a third part having a first end coupled to the first part and a second end coupled to the second end of the variable volume element, a high-pressure chamber supplying fluid to the variable volume element, and a low-pressure chamber receiving fluid from the variable volume element.

The implant may further comprise a recharging variable volume element which includes a first end coupled to the first end of the third part and a second end coupled to the first part.

The recharging variable volume element may be adapted to communicate with at least one of the high-pressure chamber and the low-pressure chamber. The second part may be rotatably coupled to at least one of the variable volume element and the third part.

The implant may further comprise a high-pressure valve allowing fluid to enter the variable volume element from the high-pressure chamber.

The implant may further comprise a low-pressure valve allowing fluid to exit the variable volume element and enter the low-pressure chamber. At least one of the first part and the second part may comprise an opening which is adapted to receive a connecting member, whereby the connecting member connects the first or second part to one of the at least two elements of the skeleton.

The invention also provides for a skeletal implant of the type to be used to connect at least two elements of a skeleton, said implant comprising at least two parts, each of which is capable of being connected to one of said at least two elements, said at least two parts being movable with respect to each other, wherein there is provided, between said at least two parts at least one of a means authorizing a displacement between said at least to parts, from a starting position to a displaced position and a means exerting a force between said at least two elements of the skeleton. Said means is responsive to control means and comprises at least one variable volume element containing a fluid. Said control means comprises a high-pressure reservoir and a very high-pressure differential variable volume recharging element for sending fluid at high-pressure into said high-pressure reservoir. Said high-pressure reservoir is connected to said at least one variable volume element via a high-pressure valve. Said at least one variable volume element is connected to a low-pressure reservoir via a low-pressure valve. Said very high-pressure differential variable volume recharging element is connected to said low-pressure reservoir via another low-pressure valve. Said very high-pressure differential variable volume recharging element is responsive to displacements of corporal parts for recharging of said high-pressure reservoir with said fluid.

Said high-pressure reservoir may be designed to maintain said fluid contained therein at high pressure, even when significant quantities of said fluid are sent to said variable volume element, provoking a substantial reduction in a volume of said fluid, in order to maintain a high value of pressure in said high-pressure reservoir, and wherein said high-pressure reservoir contains an energy accumulator in the form of a cell having an elastically deformable wall, said energy accumulator being configured to assume a compressed and reduced volume state when fluid is introduced into said high-pressure reservoir, and being configured to assume an expanded state to maintain a high pressure when fluid is withdrawn from said high-pressure reservoir.

The invention also provides for a skeletal implant of the type to be used to connect at least two elements of a skeleton, said implant comprising at least two parts, each of which is capable of being connected to one of said at least two elements, said at least two parts being movable with respect to each other, wherein there is provided, between said at least two parts at least one of a means authorizing a displacement between said at least to parts from a starting position to a displaced position wherein the means comprises at least one variable volume element containing a fluid and a means exerting a force between said at least two elements of the skeleton. Said means is responsive to control means. Said control means comprises a high-pressure reservoir and a very high-pressure differential variable volume recharging element for sending fluid into said high-pressure reservoir. Said high-pressure reservoir is connected to said variable volume element via a high-pressure valve. Said variable volume element is connected to a low-pressure reservoir via a low-pressure valve. Said high-pressure valve and said low-pressure valve are relatively spaced apart from one another.

BRIEF DESCRIPTION OF DRAWINGS

Particular embodiments of the invention will now be described, by way of a non-limiting example, in reference to the appended schematic drawings, in which:

FIGS. 1a and 1b schematically illustrate the principal of the invention applied to the formation of a callus after the fracture of a long bone;

FIG. 2 schematically illustrates a femoral reconstruction process after a fracture of the neck;

FIG. 3 shows a screw according to the invention which can be used to implement the process of FIG. 2;

FIG. 4 is a larger-scale view of the detail IV of FIG. 3;

FIG. 5 is an even larger-scale axial section of the detail IV;

FIG. 6 is a schematic axial section illustrating the functioning of this screw;

FIG. 7 is a schematic axial section of a shock-absorbing device which can be used in an implant according to the invention;

FIG. 25 is a schematic axial section of an application of the invention to an intervertebral prosthesis;

FIG. 26 shows the implantation of the prosthesis of FIG. 25;

FIG. 27 is an axial sectional view of a "ligament" of FIG. 26;

FIG. 28 shows a schematic top view of an embodiment of an intervertebral prosthesis according to the invention;

FIG. 29 is a sectional view along the line XXIX—XXIX of FIG. 28;

FIG. 30 is a sectional view along the line XXX—XXX of FIG. 28;

FIG. 31 is a sectional view along the line XXXI—XXXI of FIG. 28;

FIG. 40 shows another implant which can be used in place of those in FIG. 13;

FIG. 41 is a view in perspective of an element of the implant of FIG. 40;

FIG. 42 is an axial sectional view;

FIG. 43 is a view similar to FIG. 41 of another embodiment;

FIG. 44 is an axial sectional view of this embodiment;

FIG. 45 illustrates the functioning of the elements of FIGS. 41 through 44;

FIG. 46 illustrates another mode of functioning of this embodiment;

FIG. 53 shows one particular embodiment of an implant from FIG. 52;

FIG. 54 shows a view of a pair of implants according to the invention for symmetrical rotation movements according to a first embodiment;

FIG. 55 shows a second embodiment of such a pair of implants;

FIG. 56 shows a third embodiment of a pair of implants for symmetrical rotations;

FIG. 60 shows a side view of an embodiment of an implant according to FIG. 58:

FIG. 61 shows a front view with partial sectioning of this implant;

FIG. 62 shows a front view, with partial sectioning, of an implant according to an embodiment from FIG. 59; and FIG. 63 shows a cross section of a detailed embodiment of the invention.

DETAILED DESCRIPTION OF THE PREFERRED EMBODIMENT

Figure 8:
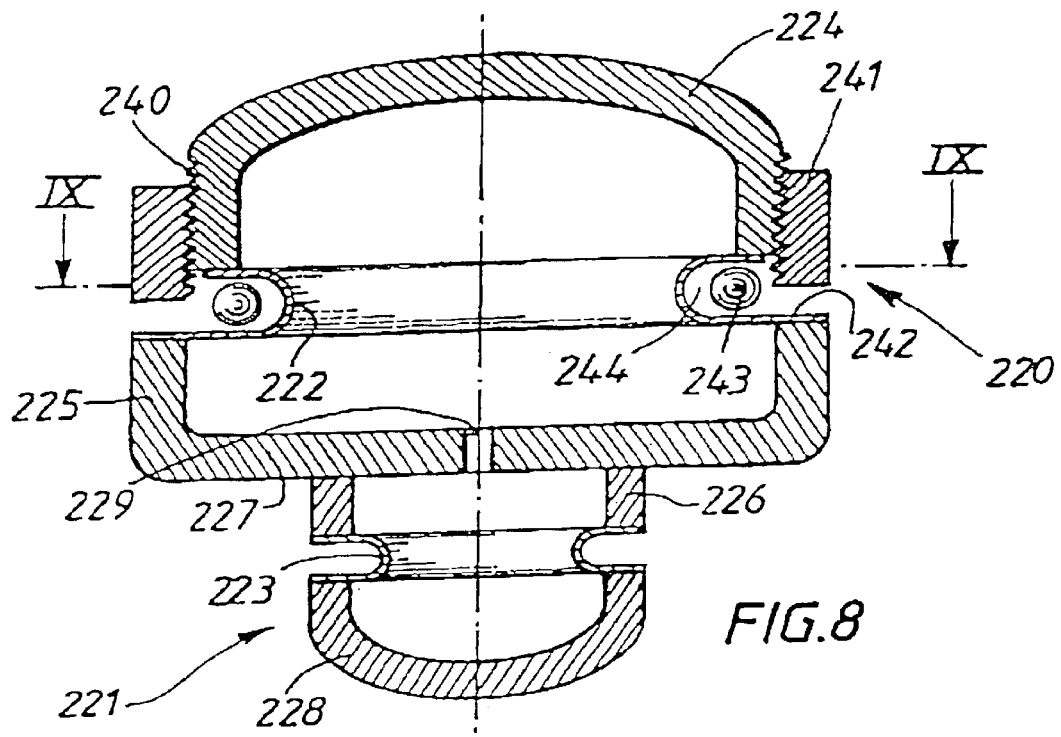
FIG. 8 is a partial view of the device of FIG. 7 showing a certain number of improvements.

FIGS. 1a and 1b represent a long bone 1 in whose middle part 2 a graft 3 has been formed, between two end elements 4 and 5.

An implant, generally designated by the reference number 6, is provided in order to consolidate the graft 3. For this purpose, the implant 6 comprises two parts 7 and 8, each of which is screwed into one of the bone elements 4 and 5, respectively. According to the invention, the opposite ends of the parts 7 and 8 are connected by a shock-absorbing device.

The shock absorber 9 is composed in a known way of a cylinder 10 which forms two closed chambers 11 and 12 respectively, separated by a piston head 13, mounted such that it slides in the cylinder. For this purpose, the cylinder 10 is filled with a hydraulic fluid, which can be laminated at the level of a calibrated opening (not represented) formed in the piston head 13.

Means of any known type, also not represented, are provided for adjusting the coefficient of resistance, for example means for adjusting the cross-section of the calibrated opening. Adjusting means of this type are present in all the embodiments described below, even in the cases where they are not mentioned.

The end of the part 7 of the implant is connected to a piston rod 14 attached to the head 13 and passing through one of the end plates of the cylinder. The end of the part 8 of the implant is connected to the cylinder 10.

Moreover, a removable rigid connecting piece 15 initially connects the end parts 7 and 8 of the implant, thus making the shock absorber 9 inactive.

The implant 6 is put in place with its connecting piece 15 (FIG. 1a), which is retained as long as no callus has formed at the level of the graft. Due to this connecting piece, the implant behaves like a standard implant, sustaining both the static and dynamic stresses. When the callus has formed (FIG. 1b), the connecting piece 15 is removed or inhibited.

Since the shock absorber exerts between the parts 7 and 8 of the implant 9 a force proportional to the relative speed of these two parts, the partially reconstituted bone will sustain all of the static stresses. On the other hand, it will be increasingly assisted by the shock absorber as the dynamic stresses it sustains become more substantial, thus causing high rates of strain, in this case tensile strain or compressive strain.

FIGS. 2 through 6 show an application of the principle explained in reference to FIGS. 1a and 1b.

These figures show the top part of a femur 100 which has sustained a fracture at the level of the neck 101. In a known way, a screw 103 is inserted into the body of the femur and into its head 104, in order to hold the latter in place until the formation of a callus and the suture of the two parts separated by the fracture.

The screw 103 is embodied in two rigid substantially cylindrical parts, namely a body 105, the part of the screw nearest the skin, and a threaded point 106, the part farthest from the skin, respectively. The part nearest the skin comprises, at its external end, a head 107 for turning the screw 103. The two end parts are connected by a flexible middle part 108.

The middle part 108 is formed by an annular bellows 109 which connects the peripheries of the inner ends of the body 105 and the point 106. A flat elastic blade 110 also connects these two ends, which blade contains their axis, thus allowing a relative pivoting movement between the two parts 105 and 106 in a plane perpendicular to the blade, while preventing such a movement in the plane of the blade. The blade 110 thus forms a neutral axis in a rotation between the parts 105 and 106 around an axis perpendicular to the axis of these parts and contained in the plane of the blade 110.

Thus, the bellows 109 and the blade 110 delimit two chambers 111 and 112 disposed on either side of the neutral axis. During a bending of the screw, which causes a relative rotation of its parts 105 and 106 around the above-mentioned axis, the volume of one of the chambers (111 in FIG. 6) increases while the volume of the other (112) decreases.

The chambers 111 and 112, as well as their connecting conduits as described above, are filled with a hydraulic fluid.

Borings 113 parallel to the axis of the screw each connect to one of the chambers 111 and 112 and connect to one another through a transverse boring 114. A valve 115 (not represented in FIG. 6) mounted in the boring 114 makes it possible to open or close the connection between the chambers 111 and 112, as well as to regulate the cross-section of the passage between these chambers.

The control rod 116 of the valve 115 is coaxial with the body 105 of the screw, and its control head, which for example is itself a screw, is included in the head 107 of the screw. Thus it is disposed near the outside of the body of the patient where the screw is inserted.

The screw 103 is position in a known way, but such that its middle part 108 is disposed at the level of the fracture. Moreover, the screw is immobilized in axial rotation in such a way that the plane of the blade 110 is perpendicular to the plane of FIG. 2, in a way that can produce a relative rotation of the parts 105 and 106 of the screw around an axis perpendicular to this plane and passing through the level of the part 108.

During the implantation, the valve 115 is closed. Thus, no connection is permitted between the chambers 111 and 112, so that the screw is perfectly rigid throughout the time it takes for the callus to form. Once the callus has formed, a minor intervention allows access to the control head of the valve 115, making it possible to open this valve, and to adjust its opening and consequently the coefficient of resistance of the implant.

FIGS. 1a and 1b illustrate the utilization of a standard shock-absorbing device. Generally, however, the shock-absorbing devices used will be better adapted to the particular use to be made of them.

Thus, FIG. 7 shows a shock-absorbing device in which each of the two chambers 220 and 221 has a variable volume due to the presence of a bellows 222 and 223, respectively.

The chamber 220 is formed of two semi-chambers in the shape of cupels 224 and 225 whose openings face one another. These cupels are connected by the bellows 222.

Likewise, the chamber 221 is formed of two semi-chambers, one of which is constituted by a cylinder 226 welded to the outside of the bottom 227 of the cupel 225, and the other of which is a cupel 228 whose opening faces the cylinder 226. The cylinder 226 and the cupel 228 are connected by the bellows 223.

Each of the bellows in this case is embodied in the form of a toric sector made of sheet metal welded along each of its edges and the edges of the cupels 224 and 225, in the case of the bellows 222, and along the free edge of the cylinder 226 and the edge of the cupel 228 in the case of the bellows 223.

The chambers 220 and 221 are filled with a hydraulic fluid and connect through a calibrated opening 229 cut into the bottom 227 of the cupel 225 and opening into the cylinder 226. Thus, when a compressive stress is exerted on the cupels 224 and 225 of the chamber 220, tending to push them toward one another, the volume of this chamber decreases while the fluid passes through the opening 229 and is forced into the chamber 221, whose volume increases. The force which opposes the approach of the cupels 224 and 225 is proportional to the approach speed, assuming that the bellows do not exert any force, particularly of an elastic nature.

When the compression stress stops, the bellows return the chambers 220 and 221 to their original configuration.

In the embodiment represented, the chamber 221 is housed in a cylindrical stress-transmitting support skirt 230, welded to the bottom 227 of the cupel 225 around the cylinder 226. In this case, the stresses are transmitted to the shock-absorbing device by the cupel 224 and the skirt 230, which two elements connect the two parts of the implant.

Figure 9:
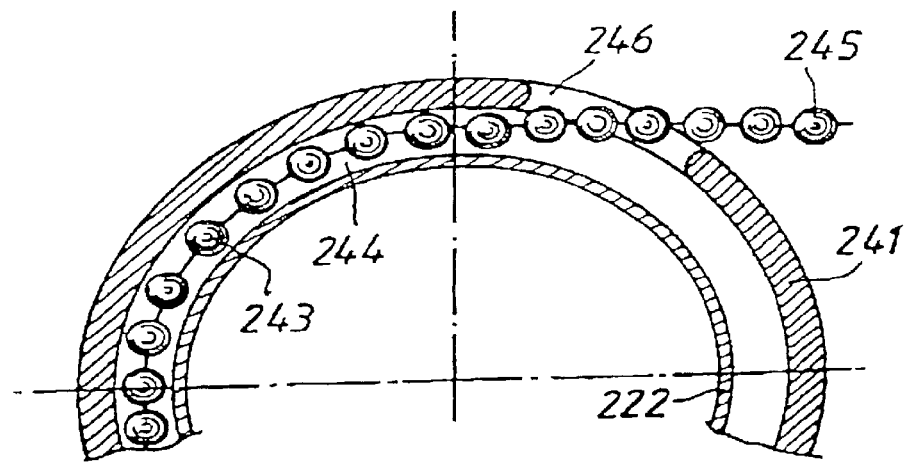
FIG. 9 is a partial section along the line IX—IX of FIG. 8.
Figure 10:
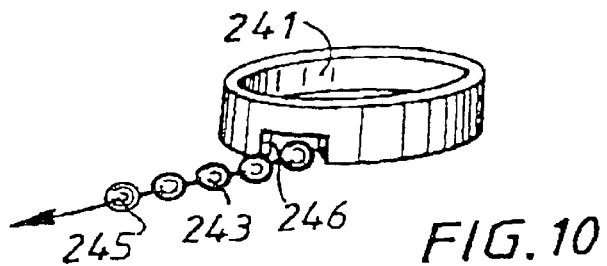
FIG. 10 is a view in perspective of elements of FIGS. 8 and 9.

In FIGS. 8 through 10, the cupel 224 comprises, in a cylindrical area, an external threading 240 onto which is screwed a stop ring 241 equipped with a cooperating internal threading. One end of the ring 241 faces a shoulder 242 of the cupel 225, in this case the edge of this cupel onto which one edge of the bellows 222 is welded.

Moreover, a beaded chain 243 is engaged in the annular space 244 delimited by the fold of the bellows 222, which includes the edge of the cupel 224, and the bottom of the ring 241. The beads of the chain in this case have a diameter substantially equal to the distance at equilibrium between the edges of the cupels 224 and 225 which face one another. One end 245 of this chain exits the annular space 244 through a slot 246 formed in the lateral wall of the stop ring 241, opposite the shoulder 242.

During the insertion of the implant, and in the subsequent consolidation phase, the chain 243 prevents the collapse of the bellows 222 in such a way that, under compression, the device behaves substantially like a traditional rigid implant. If the chain has a diameter smaller than the thickness of the space 244, the device has a partial shock-absorbing function in this phase.

After consolidation, the chain 243 is removed by pulling on its end 245, the device then functioning entirely according to the shock-absorbing principal of the invention. However, a compression limit is obtained by the abutment of the edge of the ring 241 against the shoulder 242 of the cupel 225. Thus, the device once again functions, under compression, like a rigid implant.

Figure 11A:
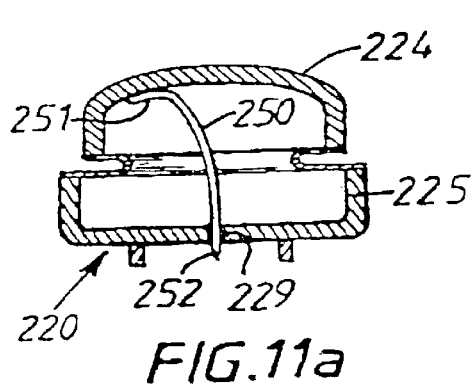
FIGS. 11a and 11b are also partial views of the device of FIG. 7 showing other improvements, in two successive phases of the utilization of the device.
Figure 11B:
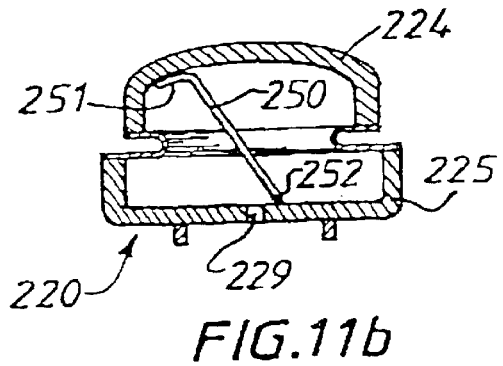

FIGS. 11a and 11b illustrate an alternate embodiment of the locking system of the chain 243 of FIGS. 8 through 10. In this case an elastic needle 250 has one of its ends 251 welded to the inside of the cupel 224 of the chamber 220. Initially, the other end 252 of the needle 250 is engaged in the calibrated opening 229, which it obstructs. Due to the incompressibility of the hydraulic fluid contained in the chambers of the device, the device is perfectly rigid.

When desiring to make the device function according to the invention, it suffices to distance the cupels 224 and 225 from one another enough to disengage the end 252 of the needle 250 from the opening 229. This opening is then free to allow the passage of the hydraulic fluid and cannot in any case be re-blocked by the needle 250.

Figure 12:
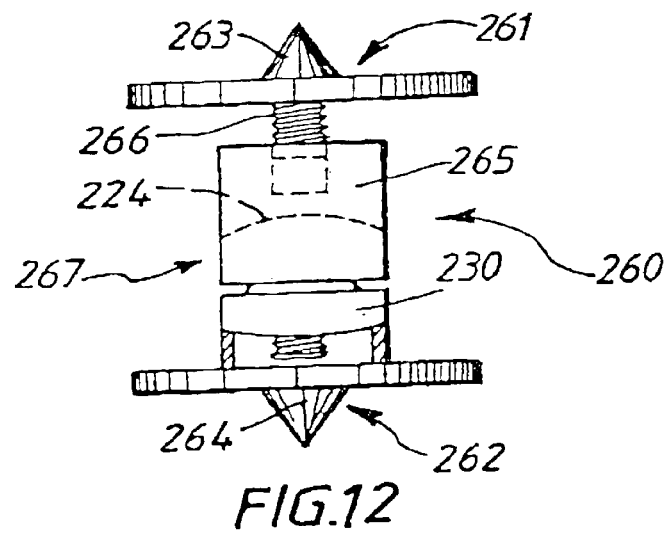
FIG. 12 is a front view in partial section of a rachidian implant embodied according to the invention.

The rachidian implant 260 of FIG. 12 comprises two end parts 261 and 262 equipped with anchoring cones 263 and 264, respectively. The part 261 also includes a sleeve 265 connected to the anchoring cone by a length adjusting screw 266.

A shock-absorbing device 267, in this case the same type as those described in reference to FIGS. 7 through 11, has a cupel 224 integral with the sleeve 265 and a skirt 230 integral with the end part 262.

An implant of this type can be used during operations for restoring the functioning or the integrity of the vertebral column. The vertebrae at least partially retain their structural functions in case of static stresses. On the other hand, the implant is more active when the dynamic stresses are substantial.

Figure 13:
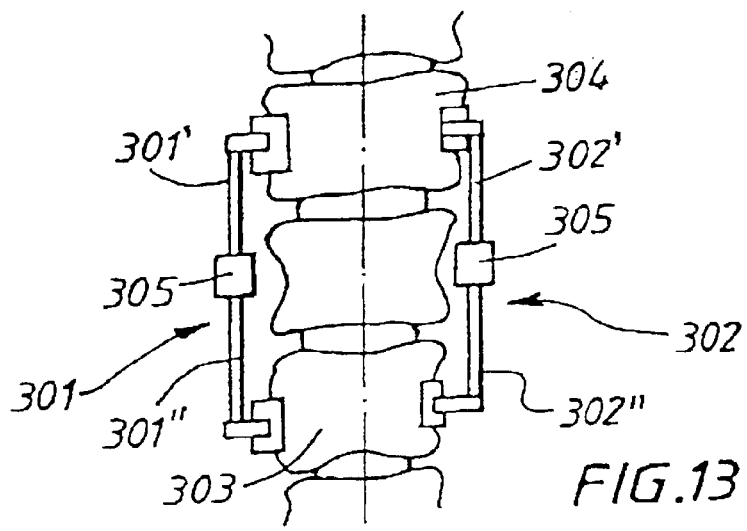
FIG. 13 shows the utilization of two implants according to the invention within the scope of a rachidian arthrodesis.

FIG. 13 shows an arthrodesis of the vertebral column in which two pins 301 and 302 are anchored in two vertebrae 303 and 304 so that, in a known way, they provide a connection between these two vertebrae. The pins 301 and 302 in this case are each embodied in two parts 301', 301" and 302', 302", respectively, each of these parts being connected at one of its ends to one of the vertebrae 303 and 304, and at its other end to the other part, by means of a device 305 according to the invention.

Figure 15:
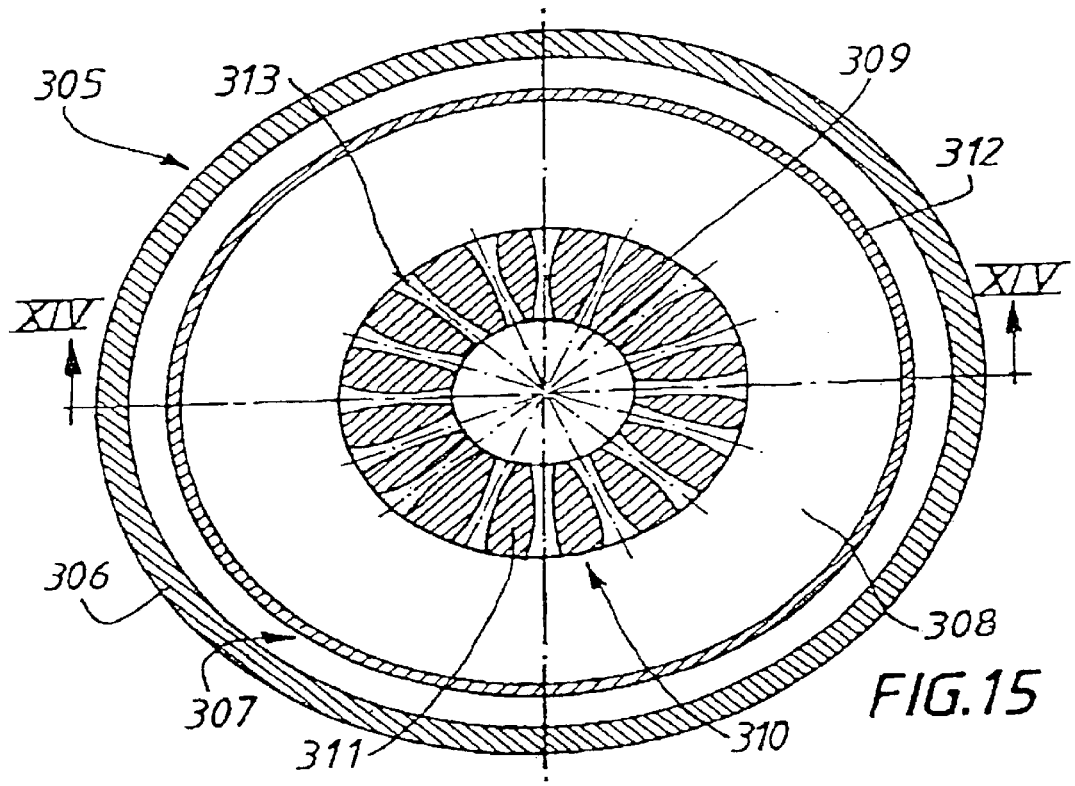
FIG. 15 is a cross-sectional view along the line XV—XV of FIG. 14.
Figure 14:
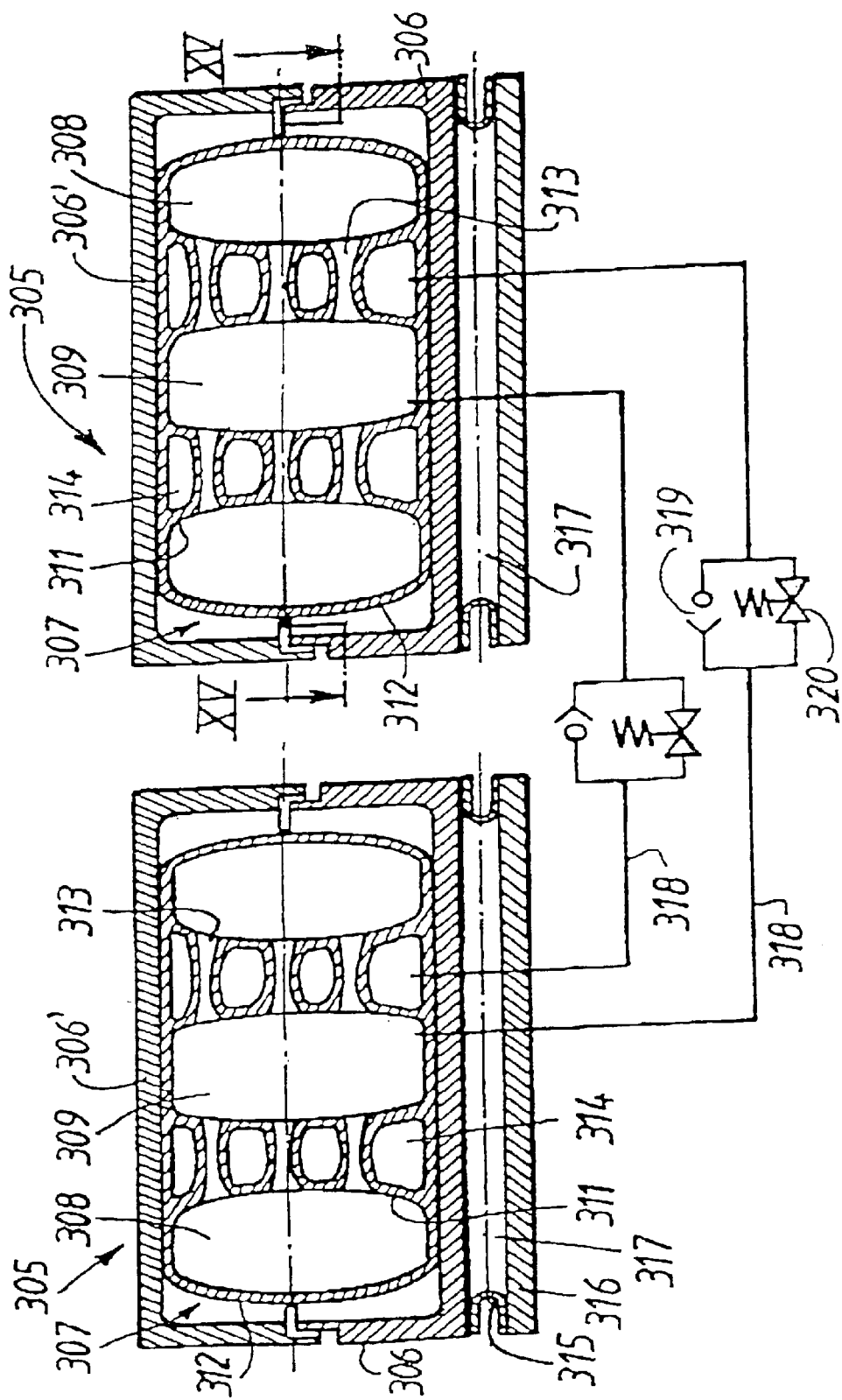
FIG. 14 shows in detail, in axial section, the implants of FIG. 13, in section along the line XIV—XIV of FIG. 15, and their interconnections.

An example of this type of device is described in reference to FIGS. 14 and 15, respectively in cross-section and in axial section.

The implant 305 comprises a shell constituted by two half-shells 306 and 306' which are upper and lower shells, respectively. Disposed inside this shell is an alveolar structure 307, particularly made of silicone, which ensures both the elastic and shock-absorbing functions between the two half-shells 306 and 306'.

The structure 307 comprises an outer toric chamber 308 and a substantially cylindrical central chamber 309, these two chambers being separated by a partition 310. The partition 310 is constituted in the following way.

It forms a thick wall 311 of low elasticity (of high elastic rigidity) relative to the external wall 312 of the outer chamber 308. Radial conduits 313 disposed inside this wall 311 connect the chambers 308 and 309. Annular chambers 314 which communicate freely with one another are formed between the conduits 313, which conduits 313 and chambers 314 are distributed in layers perpendicular to the axis of the prosthesis.

The lower half-shell 306 in this case is connected by a bellows 315 to base 316. Means, not represented, make it possible to inject hydraulic fluid under pressure into the chamber 317 delimited by the bottom of the half-shell 306, the bellows 315 and the base 316. It is thus possible to adjust the axial thickness of the implant 305.

Obviously, a differential adjustment of the two bellows 315 makes it possible to realign the vertebrae of FIG. 13.

By providing a range of adjustment that is sufficient to allow a substantial variation of the length of the device, it is possible to produce and adjustable internal fixation, allowing the repair of the vertebrae without the need for osseous fusion of the joints of these vertebrae.

Other means which are not represented, but which are included for most fluid injection sites or adjusting buttons implanted under the skin of the patient, make it possible to adjust the pressure in the chambers 308 and 309 on the one hand, and 314 on the other hand, the pressure at equilibrium in effect being equal in the low-pressure chambers 308 and 309, and lower than the pressure in the high-pressure chamber 314.

FIG. 14 also shows that the central low-pressure chamber 309 of each prosthesis 305 is connected to the high-pressure chamber of the other prosthesis by conduits 318 equipped as described below.

Mounted in each conduit 318 is an anti-return valve 319 which can open from a low-pressure chamber 309 into the corresponding high-pressure chamber 314, when the pressure in the chamber 309 becomes higher than that in the chamber 314. Moreover, a pressure control valve 320 is mounted in parallel with the valve 319, which valve is calibrated in a known way to establish a predetermined differential pressure between the low-pressure chamber 309 and the high-pressure chamber 314.

It is noted that the conduits between the low-pressure chambers could, in a variant, be disposed outside the shell. One such embodiment would involve producing a conduit of this type at least partially in the form of a catheter made of elastic material surrounded by a substantially more rigid tube, the catheter and the tube being joined into rings at their ends, for example by means of adhesive bonding or welding. The high-pressure chamber in this case is constituted by the volume between the catheter and the tube.

Figure 16:
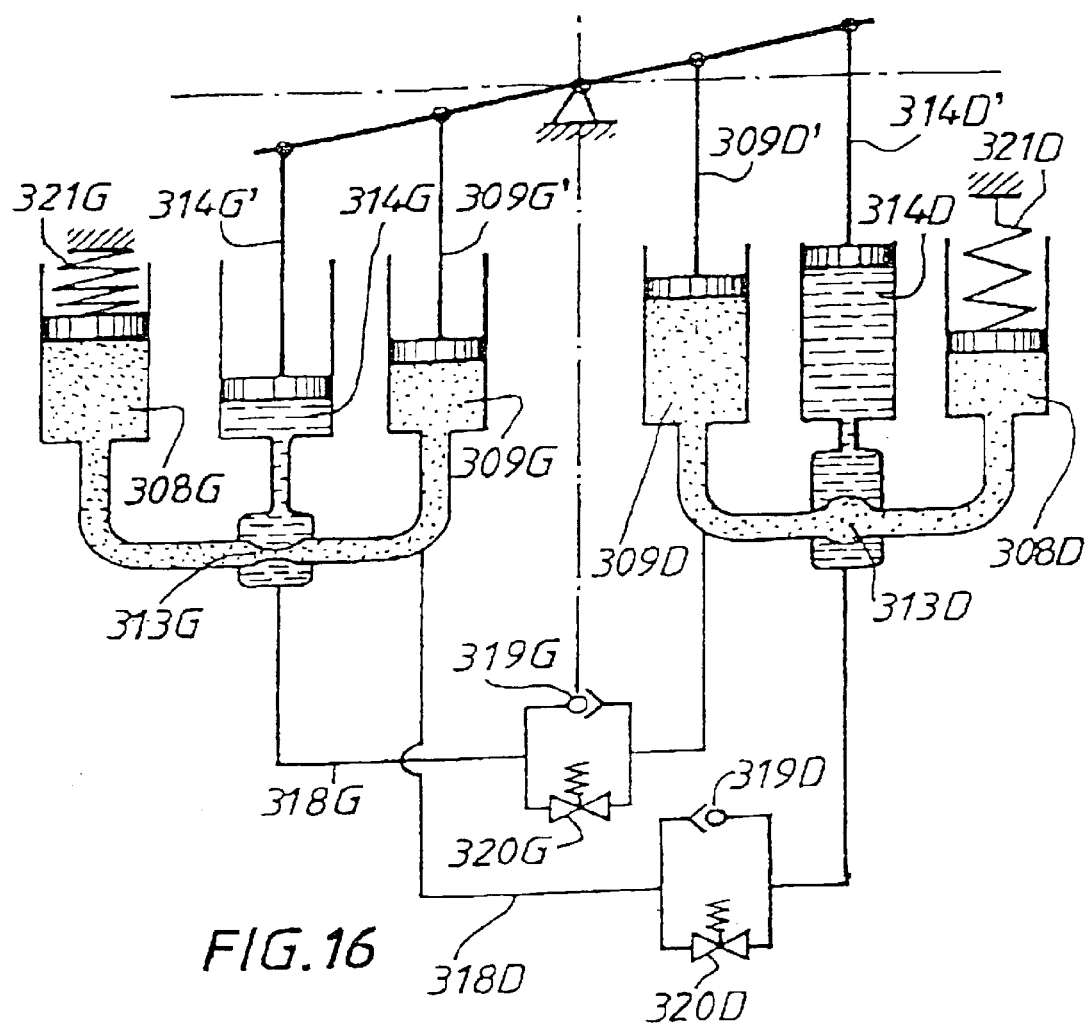
FIG. 16 is a diagram of the device of FIGS. 13 through 15.

Refer now to FIG. 16, in which the same reference numbers used in FIGS. 14 and 15 have been repeated, combined with the letters D and G for the right and left implants, respectively (seen from the rear of the patient wearing the prosthesis).

In FIG. 16, the various chambers are comparable to pressure cylinders wherein the body constitutes the chamber itself. These cylinder bodies are considered to be fixed, which means that the lower parts 301' and 302' of the pins 301 and 302, the bases 316, and the lower half-shells 306 are assumed to be fixed.

The pistons 309D' and 309G' and 314D' and 314G' illustrate the stresses exerted on the corresponding chambers by the upper half-shells 306' when the patient bends laterally, to the left in FIG. 16 as seen from behind. As for the pressure cylinders 308D and 308G, the elasticity of the walls is only symbolized, by the springs 321D and 321G, the pressure variations in the chambers 308 in practice resulting only in movements of fluid though the conduits 313 due to this elasticity.

Finally, these conduits 313 are symbolized by flexible restrictions compressed to a greater or lesser degree by the fluid contained in the high-pressure chambers 314.

The behavior of the left implant, which is compressed during the movement, will now be examined. Due to the thickness of the wall 311 and thus its low elasticity, the central low-pressure chamber 309 can increase in diameter only slightly to compensate for the decrease in its height. The fluid it contains will then be expelled through the conduits 313 to the peripheral low-pressure chamber 308. Thus, the desired shock-absorbing function is obtained.

Furthermore, the elasticity of the wall 312, symbolized by the spring 321 of FIG. 16, will simultaneously have the tendency to resist the expansion of the chamber 308, and therefore the entry of the fluid into this chamber. Thus, the function of elastic resistance is obtained.

It is noted that, as the left half-shells 306 and 306' move closer together, the left high-pressure chambers 314 also move closer to one another, which has the effect of increasing the coefficient of resistance by reducing the cross-sections of the conduits 313.

On the right side, where conversely, the half-shells 306 and 306' have a tendency to move apart, the fluid will move in the opposite direction Due to the rigidity of its walls, the cross-section of the chamber 309 will not vary much. But as its height, and therefore its volume, increases, fluid will enter it from the chamber 308 through the conduits 313. The cross-sections of the latter will increase, which will have the effect of reducing the coefficient of resistance on this side, thus compensating for its increase on the other side.

This elastic behavior will result from most of the stresses exerted on the lateral wall of the chamber 309.

Consequently, it is noted that during the patient's movement, the implant essentially sustains the high-amplitude or high-speed stresses. But it is the bone graft which will sustain the moderate static loads or loads resulting from relatively slow movements. The result is a reduction in the risk of osteoporosis.

It will now be seen, in reference to FIGS. 17a through 17d, how the differential pressure between the high-pressure and low-pressure chambers, which is essential for retaining the shock-absorbing characteristics of the implant, is regulated. These figures illustrate the pressure levels in the central low-pressure chamber and the high pressure chambers as a function of time.

Figure 17A:
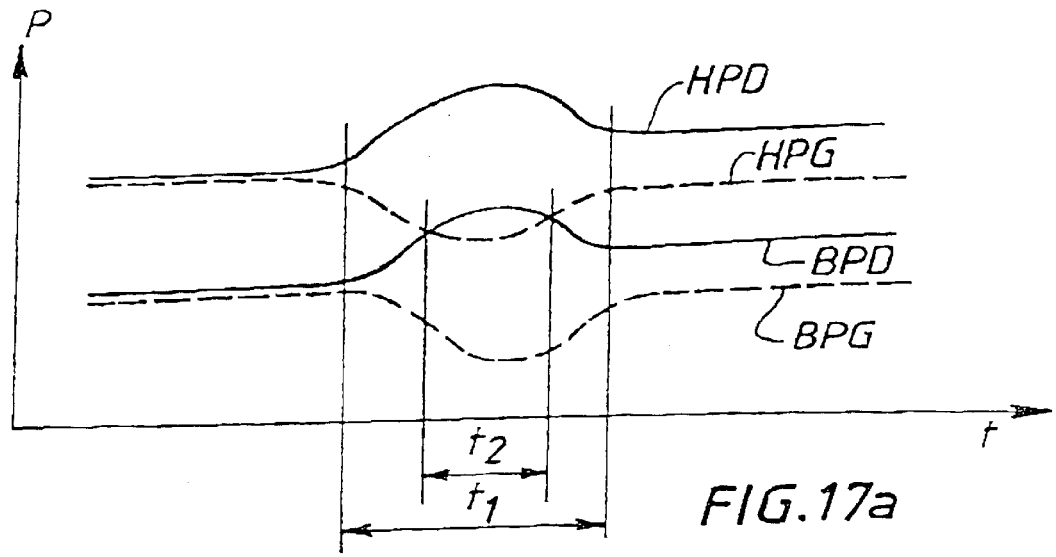
FIGS. 17a through 17d illustrate the functioning of the devices of FIGS. 13 through 16.
Figure 17B:
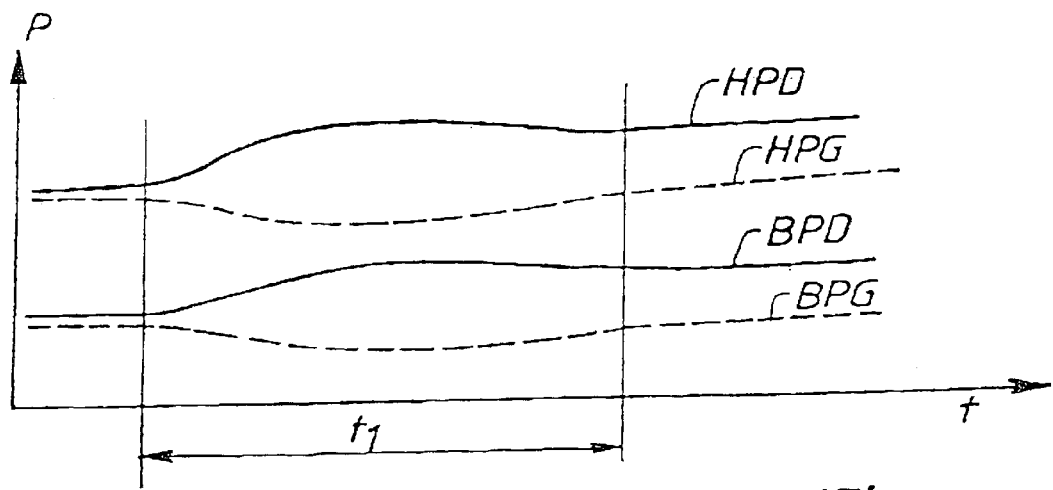
Figure 17C:
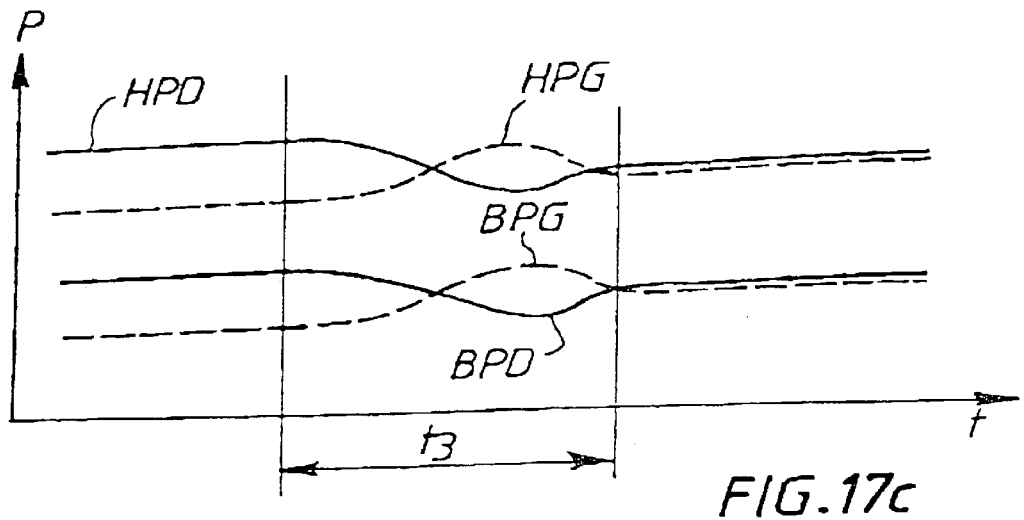
Figure 17D:
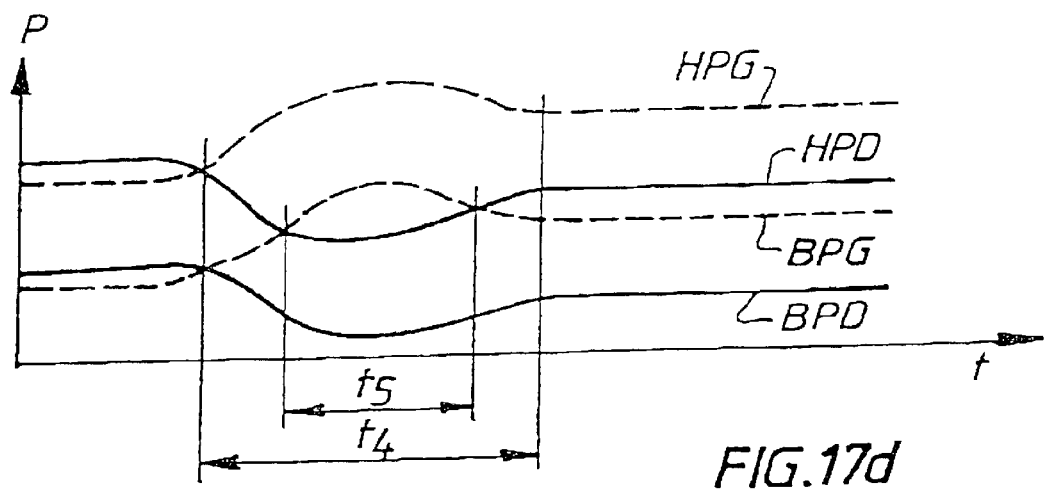
Figure 18:
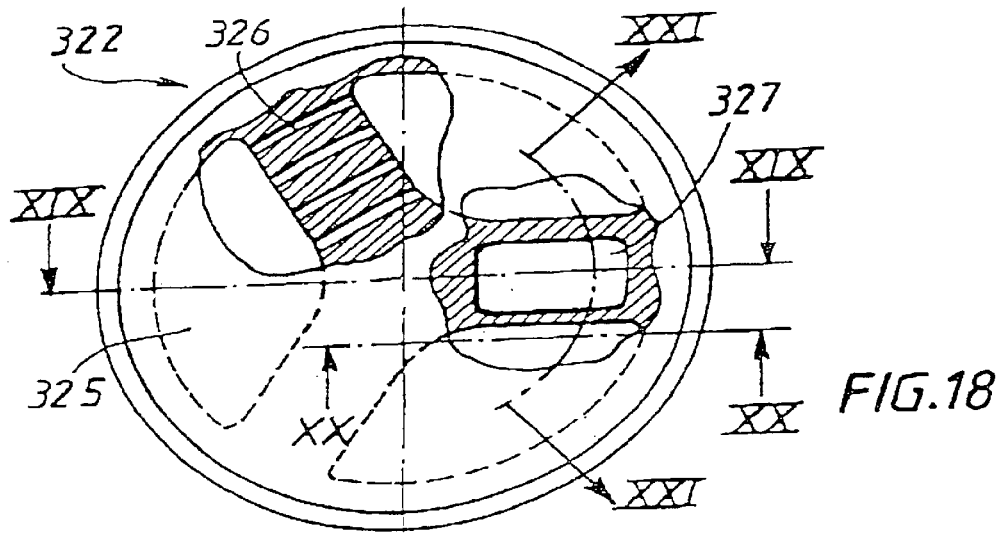
FIG. 18 shows a top view, in partial cross-section, of another embodiment of a rachidian prosthesis according to the invention.
Figure 19:
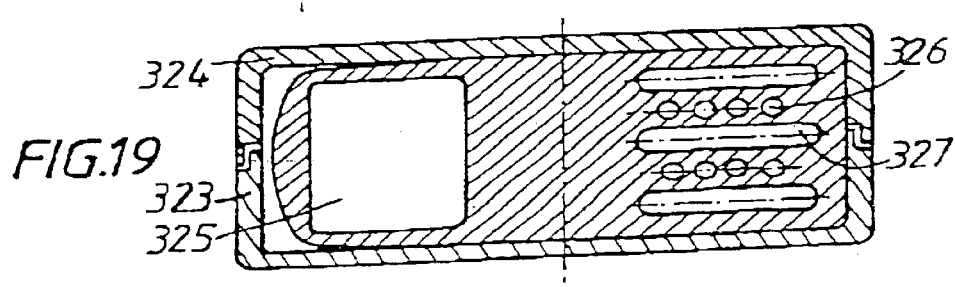
FIG. 19 is a sectional view along the line XIX—XIX of FIG. 18.
Figure 20:
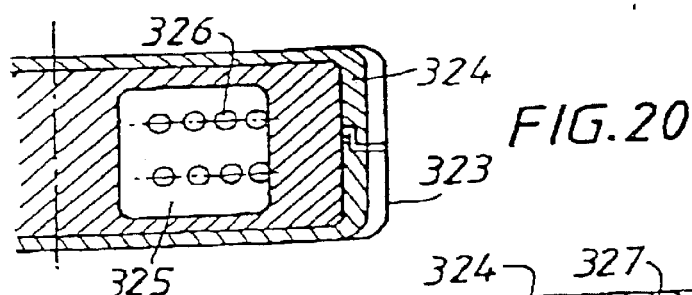
FIG. 20 is a sectional view along the line XX—XX of FIG. 18.
Figure 21:
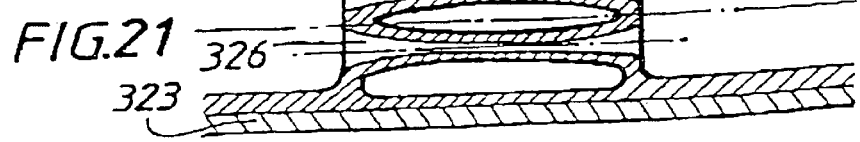
FIG. 21 is a sectional view along the line XXI—XXI of FIG. 18.

It is assumed, in reference to FIGS. 17a through 17d, that the patient successively bends to his right rapidly (FIG. 17a), or slowly (FIG. 17b), straightens himself (FIG. 17c), and bends again, but to his left (FIG. 17d). The solid lines (HPD and BPD) relate to the right implant, and the broken lines (HPG and BPG) relate to the left implant.

During a rapid movement, a substantial pressure peak is observed which is positive on the bent side, and negative on the other side, in both the high-pressure and low-pressure chambers. The reason why this occurs in the high-pressure chambers will be explained below. In the low-pressure chambers, it is due to the rigidity of the walls of the chambers 309 and the shock-absorbing effect of the conduits 313, which slow the flow of fluid from the chambers 309 to the chambers 308.

The time $t_1$ that it takes for the patient to bend to the right, during which the pressure levels vary, then stabilize, can be seen in FIGS. 17a and 17b. The respective pressure levels were substantially equal before the movement, by reason of symmetry, but after the movement the pressure levels are obviously higher on the right than on the left.

When the movement is rapid enough, there is a period $t_2$ included in $t_1$ during which the pressure in the right low-pressure chamber 309 becomes higher than the pressure in the left high-pressure chamber 314. The anti-return valve 319G then opens and allows the passage of fluid from the right low-pressure chambers to the left high-pressure chamber. Simultaneously, the pressure control valve 320G allows a flow in the opposite direction so as to prevent the differential pressure between the high and low pressure from exceeding the set-point value.

Thus, if need be for any reason, the differential pressure predetermined by the calibration value of the pressure control valve is re-established. This can occur continuously in the case of leaks from the high-pressure chambers to the low-pressure chambers, or when the low-pressure chambers are refilled by injection, or even when an adjustment is made to increase the differential pressure between the high and low pressure. The device then functions like a pump controlled by the movements of the patient.

If, on the other hand, the bending movement is slow, as shown in FIG. 17b, the fluid has the time to flow from the right low-pressure chambers 309 to 308 without causing excessively high pressure levels. The anti-return valve 319G does not open.

When the patient straightens, the pressure levels change as shown in FIG. 17c. Given that the pressure levels on the right side are initially higher than those on the left side, it is not very probable that during the period $t_3$ of the movement the. prevailing low pressure in the left chamber 309 will become greater than the prevailing high pressure in the right chamber 314.

It is only when the patient bends quickly enough to the left, as represented in FIG. 17d, which is symmetrical to the case in FIG. 17a, that the differential pressure between the right high-pressure chamber and the left low-pressure chamber re-establishes its set-point value. The period $t_4$ of the movement, and the period $t_5$ during which the left low pressure becomes greater than the right high pressure, as shown in this figure.

It is understood that what has just been described step-by-step in reference to FIGS. 17a through 17d actually occurs continuously when the patient is moving normally, successively adopting various natural postures. Consequently, it is noted that this results in a continual biochemical adaptation of the implants to the stresses imposed on it by the patient.

In light of the auto-refill principle explained in reference to FIGS. 17a through 17d, it may be seen that the pressure points that are too acute will flatten out due to the fact that the fluid is laminated as it flows into the anti-return valve. This produces an additional shock-absorbing effect when the cell is stressed suddenly enough that the low pressure surpasses the high pressure. Taking into account the variability of the coefficient of resistance as a function of the loads, as described above, this proves to be a device endowed with an advantageous capacity for self-adjustment.

Another advantage of this mode of functioning resides in the fact that a practically continuous circulation of fluid occurs in the hydraulic circuit of the implant of the invention. This circulation avoids the risk of collapse and thus limits the need for maintenance operations.

Another embodiment 322 of the implants 305 is seen in FIGS. 18 through 22.

The implant 322 is again embodied in the form of an alveolar structure made of elastomer contained in a shell composed of a lower half-shell 323 and an upper half shell 324.

The alveolar structure of this embodiment is in the shape of a disk and forms three low-pressure chambers 325 in the form of sectors, distributed substantially equally around the axis of the disk, at 120° from one another. The three chambers 325 connect through a network of calibrated conduits 326, here disposed in two transverse layers.

Three groups of high-pressure chambers 327, which communicate with one another by any appropriate means, are disposed between the low-pressure chambers 325. The chambers 327 are flat in shape, and each group has three of them, interposed between the layers of conduits 326. The pressure in the high-pressure chambers determines the cross-section of the conduits 326 and thus their characteristics of viscosity.

Figure 22:
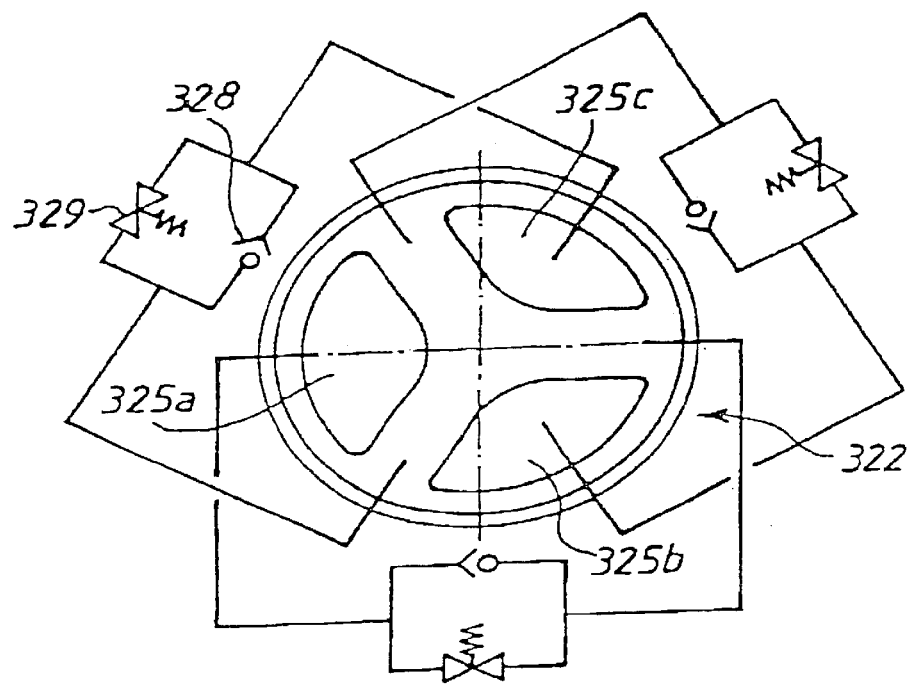
FIG. 22 illustrates the interconnection of the chambers of the prosthesis of FIG. 18.

FIG. 22 shows that the low-pressure chambers are connected to the high-pressure chambers by a set of anti-return valves and pressure control valves. Each low-pressure chamber 325 is connected to the high-pressure chamber 327 that is diametrically opposed to it by an anti-return valve 328 which opens in the direction from the chamber 325 to the chamber 327, in parallel with a pressure control valve 329.

In this case, there is no intersection, as in the embodiment of FIGS. 14 and 15, and as symbolized in FIG. 17, of the connections between the low-pressure and high-pressure chambers of two implants mounted in parallel. Moreover, there is only one type of low-pressure chamber.

During an axial compression, the fluid contained in the conduits 326 is, due to the thickness of the walls of the latter, expelled to the chambers 325 with a viscous fluid behavior. The walls of these chambers are then forced toward the outside, giving the implant its elastic behavior. In this respect, this implant behaves like the one in the preceding embodiment.

On the other hand, this implant has a particular behavior relative to non-axial loads. For example, in the case of a load exerted from the left side of FIG. 22, the low-pressure chamber 325a will be compressed, while the chambers 325b and 325c will be at low pressure. The wall of the chamber 325a will then expand, while part of the fluid contained in this chamber will flow into the chambers 325b and 325c through the conduits 326, further drawn by the prevailing low pressure in these chambers.

When the movement is large enough and rapid enough, the outer wall of the low-pressure chamber 325a comes into contact with the shell. The elastic behavior of the implant is then blocked, so that the pressure rises sharply in the low-pressure chamber 325a. This pressure can then become greater than the prevailing pressure in the high-pressure chamber 327a which faces it, engaging the process for regulating the differential pressure described above in reference to the preceding embodiment.

An implant according to this second embodiment could therefore be used alone, while retaining the differential pressure regulation function.

Various implantations other than that represented and described in reference to FIG. 13 can be envisaged for the implants just described.

Figure 23:
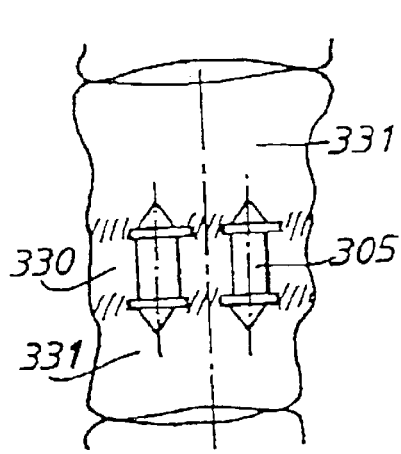
FIG. 23 shows another possible assembly of two implants like those shown in FIG. 14.

FIG. 23 shows a bone graft 330 disposed between two vertebrae 331. Two implants 305 such as those in FIGS. 14 and 15 have been placed in the graft, symmetrically relative to the median plane of the patient's body. The interconnections between the implants and the functional principles are the same as those described in reference to FIGS. 14 through 17.

Figure 24:
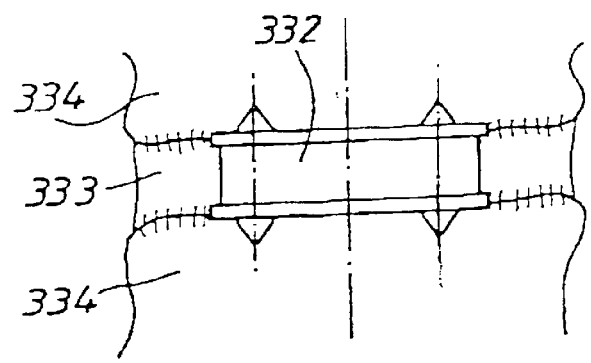
FIG. 24 illustrates a variant of FIG. 23.

FIG. 24 shows a single implant 332 as described in reference to FIGS. 18 through 22, implanted in a graft 333, which is itself disposed between two vertebrae 334. A solution of this type ensures good performance with regard to lateral as well as frontal flexions.

Articulated implants embodied according to the invention will now be described.

FIG. 25 shows an implant, or intervertebral prosthesis 400 intended to be disposed, as shown in FIG. 26, between two vertebrae 401, in place of an intervertebral disk. This implant must therefore allow certain movements between the vertebrae 401, contrary to what occurs in the case of an arthrodesis.

The implant 400 is generally formed by a shell comprising a bottom 402 and a cover 403. The cover 403 rests on the bottom 402 as a result of two spherical surfaces with the same radius, the surface 404 of the bottom which faces upward and the surface 405 of the cover which faces downward. Thus, the cover 403 can pivot relative to the bottom 402 around three axes.

The bottom 402 is hollow, so as to define a space 406 inside the implant. The cover 403 forms a projection 407 into this space, the end of which projection is connected to the bottom by three inner viscoelastic "ligaments" 408, which will now be described in reference to FIG. 27.

Each ligament 408 comprises a rigid hollow body 409 which is substantially cylindrical and has, at one of its ends, an opening to the ambient air 410. This opening is sealed by an ampulla, or elastic bellows 411. The bellows 411 is a cylinder closed at its end opposite the opening 410 by a bottom 412, and its lateral wall forms a helical fold 413 with a variable pitch which increases from the opening 410 to the bottom 412.

The body 409 and the bellows 411 delimit a chamber 414 containing a hydraulic fluid which is supplied from, and whose pressure can be regulated by, a conduit 415 and a valve 416.

At the other end of the body 409, the base 417 of this body supports an annular cylindrical chamber 418 whose inner wall 419 and outer wall 420 are also constituted by bellows. The chamber 418 contains a hydraulic fluid which is supplied from, and whose pressure is regulated by, a conduit 421 and a valve 422.

At the center of the annular chamber 418, the wall of another cylindrical chamber 423 is formed by a bellows 424. The chamber 423 connects to the chamber 414 through a calibrated opening 425 cut into the base 417 of the body 409. The chamber 423 is therefore supplied and pressurized from the chamber 414.

The end of the bellows 424 opposite the base 417 is sealed by a plate 426 which carries a support piece 427 passing through an opening 428 of an end plate 429 of the annular chamber 418. The end plates 426 and 429 are integral.

Formed inside the chamber 423 is a chamber 430 mounted on the base 417 of the body 409 by means of posts 431. One of these posts 431 is hollow and makes it possible to supply and to pressurize the chamber 430 with hydraulic fluid from a conduit 432 and a valve 433.

The wall of the chamber 430, between the junction points of the posts 431 and the base 417, forms a bellows 434. The bottom of the chamber 430, which faces the base 417 of the body 409, carries a needle 435 which penetrates into the calibrated opening 425.

The implant is anchored at the projection 407 and at the bottom 402 by its elements 409 and 427.

It is easily understood that the length of the ligament 408 is a function of the pressure in the annular chamber 418, which determines the elongation of the bellows 419 and 420. This length can be adjusted by means of the valve 422.

Moreover, the coefficient of resistance of the ligament 408 is a function of the free cross-section of the calibrated opening 425, and thus of the penetration depth of the needle 435. This coefficient can be adjusted by means of the valve 433.

Finally, with regard to its elasticity, the bellows is comparable to a helical spring with a variable pitch which becomes increasingly steep as it is compressed and its spires progressively come into contact. This bellows determines the elasticity of the ligament 408 since, when the latter is compressed, it elastically opposes the penetration of the hydraulic fluid into the chamber 414 through the opening 425. The coefficient of elasticity can therefore be adjusted by means of the valve 416 by pre-compressing the bellows 411 to a greater or lesser degree.

It is noted that a structure similar to that of the ligament just described could be used in place of the device of FIG. 7, in order to render its various functions adjustable.

An alveolar structure 500 made of elastomer which could replace the three ligaments 408 of FIG. 25 will now be described in reference to FIGS. 28 through 31.

This structure is practically identical to that of the implant 322 of FIGS. 18 through 21 (FIG. 28 has been schematized). It is noted, however, that in this case the structure 500 has an opening 501 of triangular section for receiving a projection of the cover, similar to the projection 407 and intended to form a pivot between the bottom and the cover of the prosthesis.

The interconnections between chambers are the same as in the case of the implant 322, and the functioning of the present prosthesis and the implant are the same from the hydraulic standpoint.

The differences reside in the way in which the stresses are applied. In this case, essentially transverse stresses are applied to the low-pressure chamber 502 by the projection of the cover.

Figure 32:
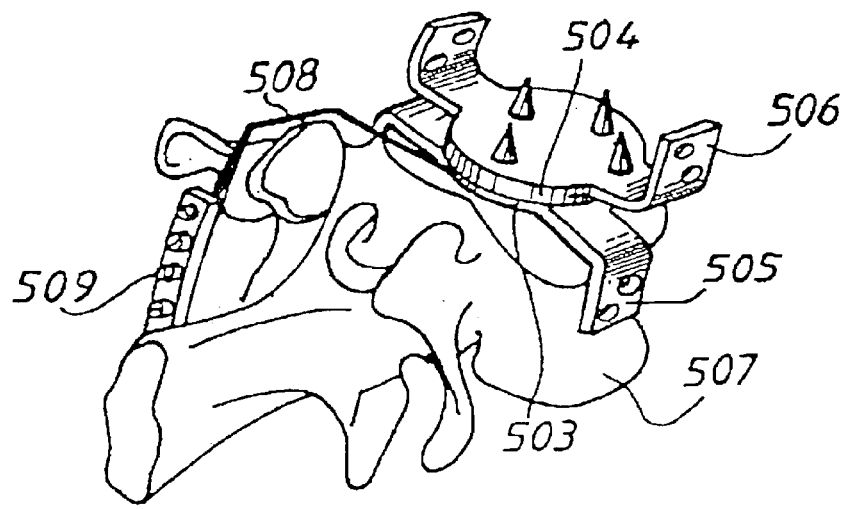
FIG. 32 is a view in perspective showing in greater detail the implantation of the intervertebral prosthesis of FIGS. 28 through 31.

FIG. 32 shows one possible implantation of the prostheses of FIGS. 25 through 31.

This figure shows the bottom 503 and the cover 504 of the prosthesis. The bottom 503 is equipped with fittings 505 and the cover 504 with fittings 506 for their respective attachment to a lower vertebra 507 and an upper vertebra not represented.

The various hydraulic chambers are connected by conduits 508 to a set of subcutaneous control buttons 509, particularly push-buttons, disposed behind the vertebrae. Safety devices are preferably provided in order to prevent ill-timed operation of the buttons. In a variant, fully hydraulic adjustment means could be provided, with a subcutaneous access site connected to the various chambers by a slide valve.

Figure 33:
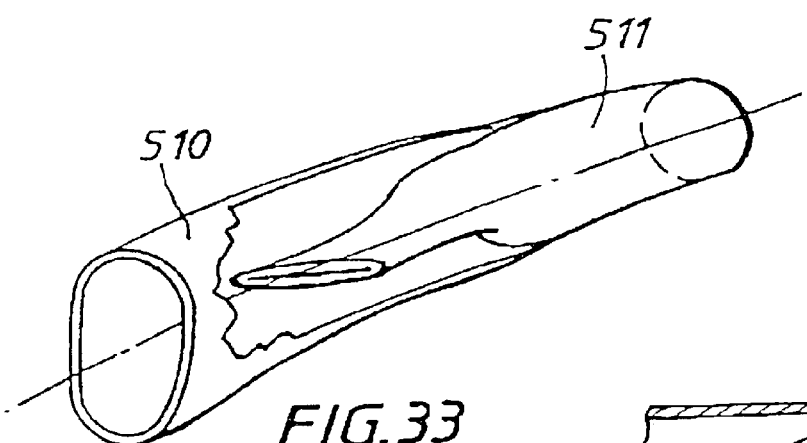
FIG. 33 is a view in perspective of an anti-return valve which can be used in an implant according to the invention.
Figure 34:
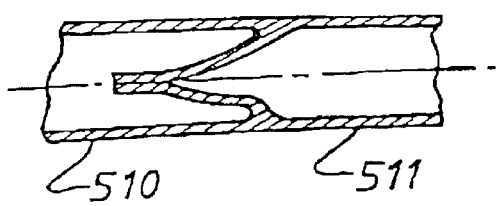
FIG. 34 is an axial sectional view.

FIGS. 33 and 34 show, in partial perspective and in cross-section, respectively, an anti-return valve which can be used in the invention.

This valve is composed of a conduit 510 connected to the high-pressure and a conduit 511 connected to the low pressure. These conduits are coaxial, and the end of the low-pressure conduit 511 is engaged inside the end of the high-pressure conduit 510. The end of the conduit 511 inside the conduit 510 is flat.

As long as the high pressure is greater than the low pressure, the end of the conduit 511 remains flat and the valve remains closed, thus preventing the possibility of a flow from the conduit 511 to the conduit 510. But when the low pressure becomes higher than the high pressure, the end of the conduit 511 opens and fluid flows from the conduit 511 to the conduit 510.

Finally, FIGS. 35 through 39 illustrate a coxofemoral prosthesis embodied according to the principles of the invention.

This prosthesis is intended to be used after a fracture of the neck of the femur and resection of its upper part. It comprises a pin 600, one end of which is intended to be attached to the remaining part of the femur, and a hollow sphere 601 whose wall includes an opening 602 to allow it to be penetrated by the other end of the pin 600.

The upper end of the pin 600, inside the sphere 601, is integral with a cylindrical head 603. The latter is capable of sliding and forming a piston in a circular opening 604 of an internal partition 605 of the sphere. The axis of the head 603 and of the opening 604 passes substantially through the other end of the femur, at the level of the knee joint.

The partition 605, along with tbs piston 603, delimits inside the sphere two chambers 606 and 607, which are respectively upper and lower chambers. The chambers 606 and 607 contain viscoelastic devices which determine the relative movement of the pin 600 and the sphere 601, as a function of the stresses applied.

In one particularly simple embodiment, these viscoelastic devices can be simply constituted by an elastic foam which fills the chambers 606 and 607, and a calibrated opening formed in the head 603. The foam contains a hydraulic fluid and an appropriate joint is disposed at the level of the opening 602.

Figure 38:
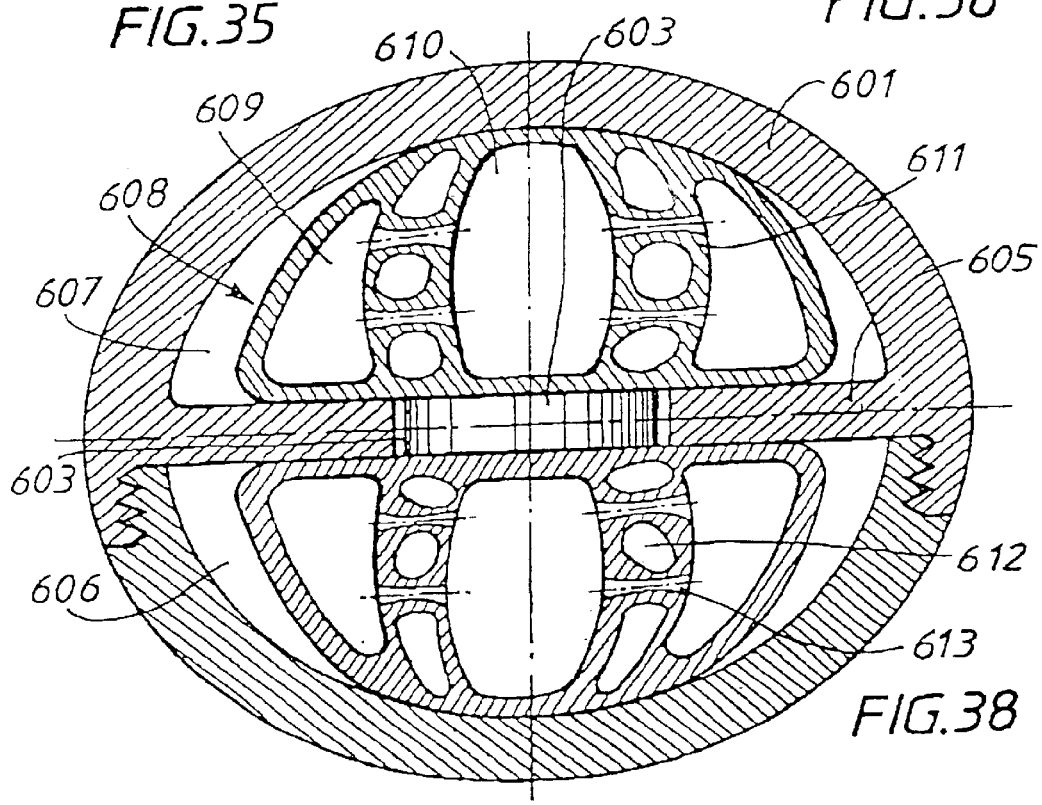
FIG. 38 is a sectional view of the head of the prosthesis of FIGS. 35 through 37.
Figure 37:
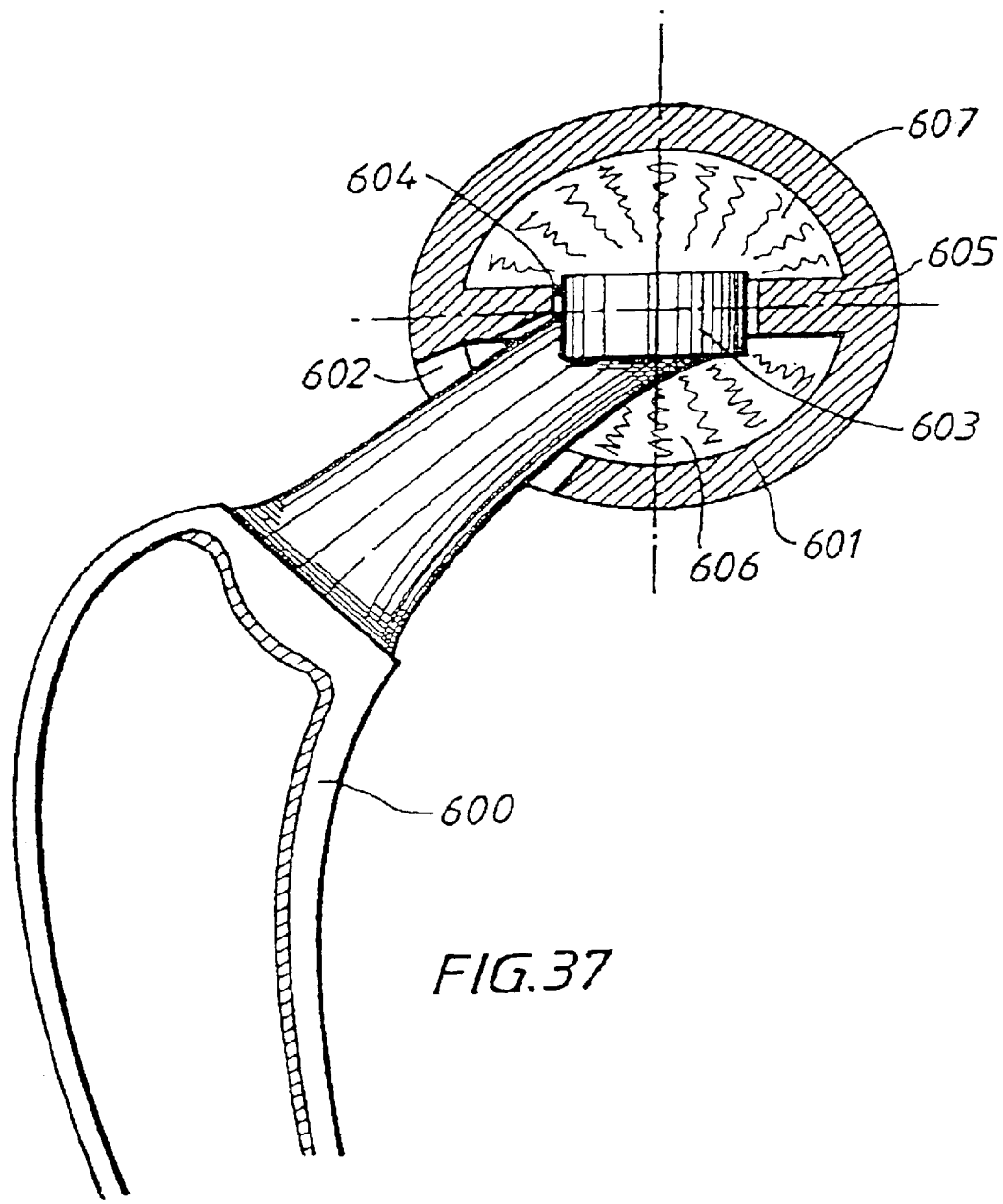
FIG. 37 is a schematic cross-sectional view.
Figure 39:
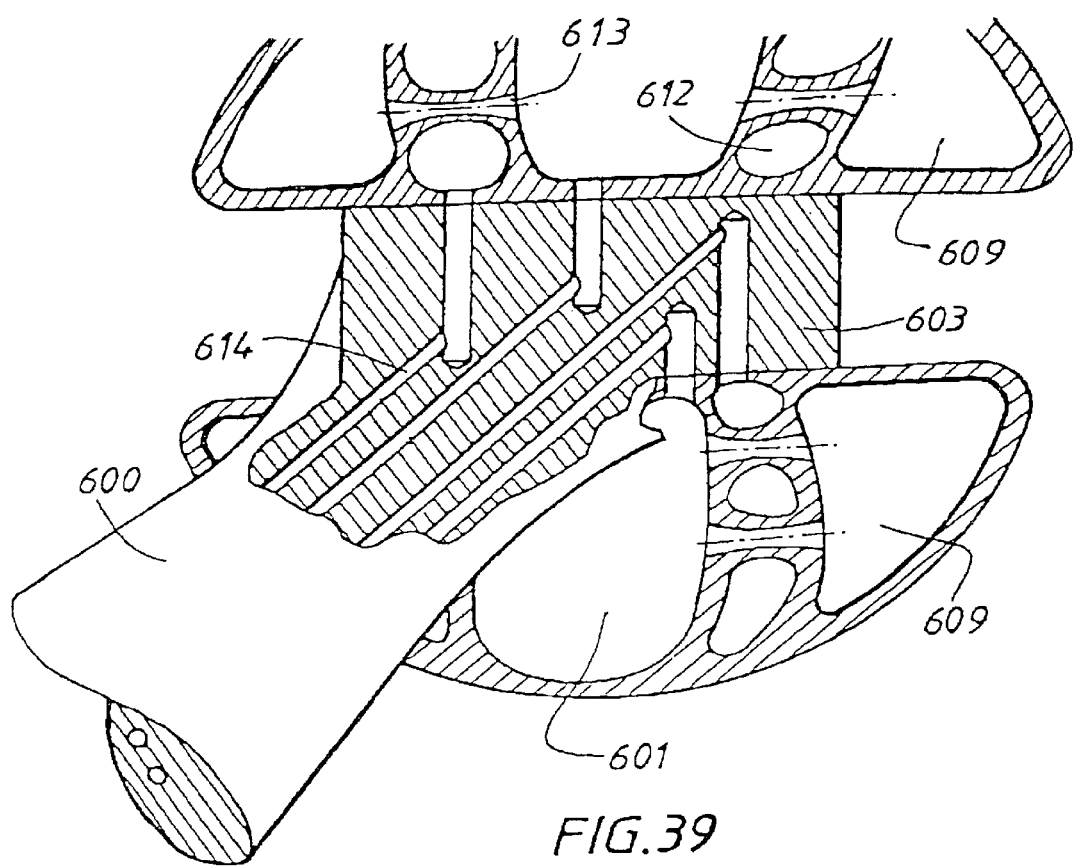
FIG. 39 is a partially exploded view of the prosthesis of FIGS. 35 through 38.

However, the embodiment in FIGS. 38 and 39 is preferred.

In this case, the viscoelastic devices 608 are embodied is a form practically identical to that of the structures 307 in the implants 305. The difference resides in the fact that the structures 307 are generally of cylindrical shape, while the devices 608 have a shape which is generally hemispherical. But in a similar way, they are chiefly composed of a peripheral low-pressure chamber 609 and a center low-pressure chamber 610, separated by a wall 611.

Annular high-pressure chambers 612 formed within the thickness of the wall 611, are interposed with calibrated conduits 613 which connect the low-pressure chambers 609 and 610. The intersecting interconnections between chambers are embodied as above.

When the prosthesis is stressed, the head 603 compresses one of the devices 608, while the other device is at low pressure. Everything indicated relative to the functioning of the twin implants 305 remains valid in the present case.

It is noted that in this case, when a device 608 is compressed, its line of tangency with the inner surface of the sphere moves closer to the partition 605. The elastic outer wall surface then decreases, which has the effect of increasing the elastic rigidity of the device.

Figure 35:
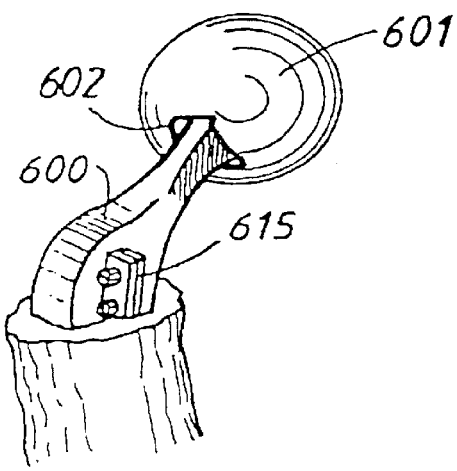
FIGS. 35 and 36 are views in perspective of a coxofemoral prosthesis embodied according to the invention.
Figure 36:
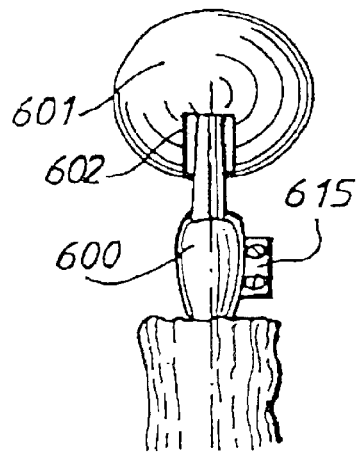

The interconnections between chambers are embodied as shown in FIG. 39, by borings 614 formed in the head 603 and in the pin 600. These borings emerge at the level of a control button box 615 (FIGS. 35 and 36). This box is disposed subcutaneously so as to be easily accessible, in order to allow the necessary adjustments.

The implant 700 of FIG. 40 generally comprises a viscoelastic cell 701, for example like that is the implant 305 of FIG. 13 and the subsequent figures, or like the ligament 408 of FIG. 27, as well as a distance adjusting element 702, in this case for adjusting the height, and a refill cell 703. These elements are mechanically disposed in series, in support, with the half-pins 704, 704' of the arthrodesis, which can belong to the two vertical members of a frame. The half-pins 704, 704' consequently support the pressure of the patient's body, which is variable as a function of his posture.

The adjusting element 702 can be embodied as shown in FIGS. 41 and 42, in the form of an expandable toric bellows, which can expand axially. Its central free space allows it to house a protuberance of the viscoelastic cell.

In a variant, the adjusting element can be is the form of the disk-shaped bellows 702' of FIGS. 43 and 44.

The adjusting element 702 (or 702') can be connected by a conduit 705 to a tube valve 706 which can itself be connected to a pump 707. Thus, it is possible to adjust the thickness of the element 702. It is therefore possible to adjust not only the total length of the prosthesis, but also the angle formed between its upper part (the half-pins 704) and its lower part (the half-pins 704') by means of a differential filling of two elements 702 of the prosthesis.

It is noted that the valve 706 itself can be implanted, in which case it is accessed either by cutaneous incision or by means of an access site, or external, the conduit 705 being transcutaneous.

In another embodiment, represented in FIG. 46, the filling of the adjusting elements is carried out with the aid of a high pressure reservoir 708, in this case dilatable, and a slide valve 709. In a similar way, the emptying of these elements occurs into a low-pressure drainage collector 710, also dilatable, through another slide valve 711 (or in the same way, through a three-way valve).

Moreover, a filling valve 712 makes it possible to fill the reservoir 708, and a drainage valve 713 makes it possible to empty the reservoir 710. The reservoirs 708 and 710 are implanted and the valves 712 and 713 can be external or implanted, as in the case of the valve 706. Generally, however, they will be implanted, since their access should be far less frequent than that of the valve 706.

The refill cells 703, whose function will be described below, are entirely similar to the adjusting elements 702. However, they are connected to the high-pressure and low-pressure reservoirs 708 and 710 not by slide valves, but by anti-return valves 714 and 715, respectively. The anti-return valves 714 are connected from the cells 703 to the high-pressure reservoir 708, and the anti-return valves 715 are connected from the low-pressure reservoir 710 to the cells 703.

The cells 703 serve as pumps for refilling the high pressure reservoir 708. In effect, when the patient bends, for example to the right, the cell 703D is compressed. When the pressure in this cell surpasses the pressure in the reservoir 708, the anti-return valve 714D opens and fluid passes from the cell 703 to the reservoir 708. Simultaneously, the left cell 703G draws in fluid from the low-pressure reservoir 710.

A pressure control valve 716 prevents the high-pressure from exceeding a predetermined value.

It is noted that if only angular corrections are desired, the refill device can be greatly simplified, and the refill cells in particular can be eliminated. In effect, in this case it suffices to connect the adjusting elements by means of a slide valve. When the patient bends, for example to the right, the valve is opened so that fluid passes from right to left, then is closed again. When the patient straightens, the height of the left side will be larger and that of the right side will be smaller.

The viscoelastic cells have not been described is this embodiment. It is simply noted that in the case where they comprise high-pressure chambers, like for example the implants 305 or the ligaments 408, those chambers can be connected to the high-pressure reservoir 708 by a valve, for example a slide valve. Thus it is possible to easily rigidify the viscous behavior of these cells. The low-pressure chambers of the viscoelastic cells, for their part, can also be connected to the low-pressure reservoir 710.

Figure 48:
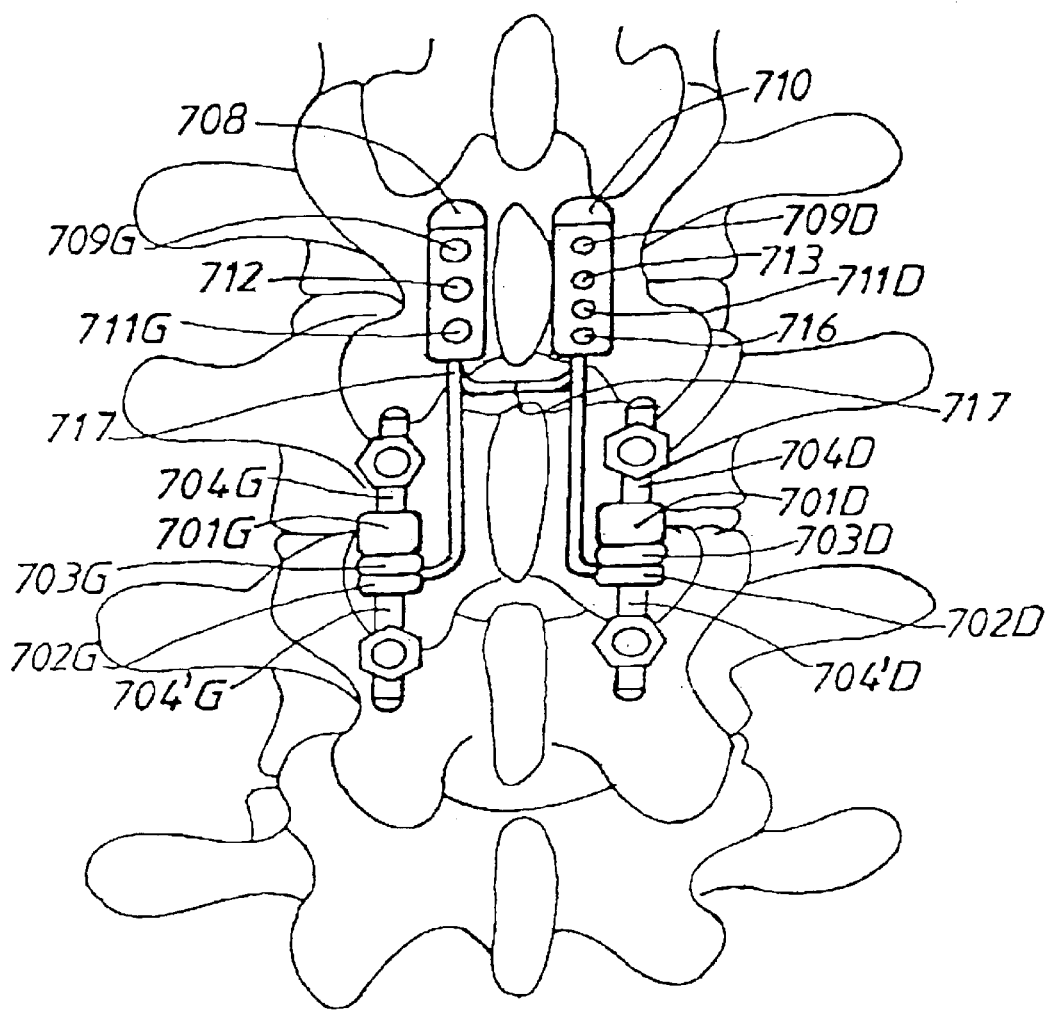
FIG. 48 shows a possible implantation of the invention on a spine.

FIG. 48 shows a possible implantation for the elements just described. The connecting conduits generally have the reference number 717. It is noted that all these elements can have very small dimensions, and the hydraulic volumes can be very low.

The physical characteristics of the implants just described can be modified postoperatively by any means, including entirely non-invasive means, whether in terms of their viscoelastic properties, their dimensions, their lateral or antero-posterior inclination, or their anti-rotational resistance.

Figure 47:
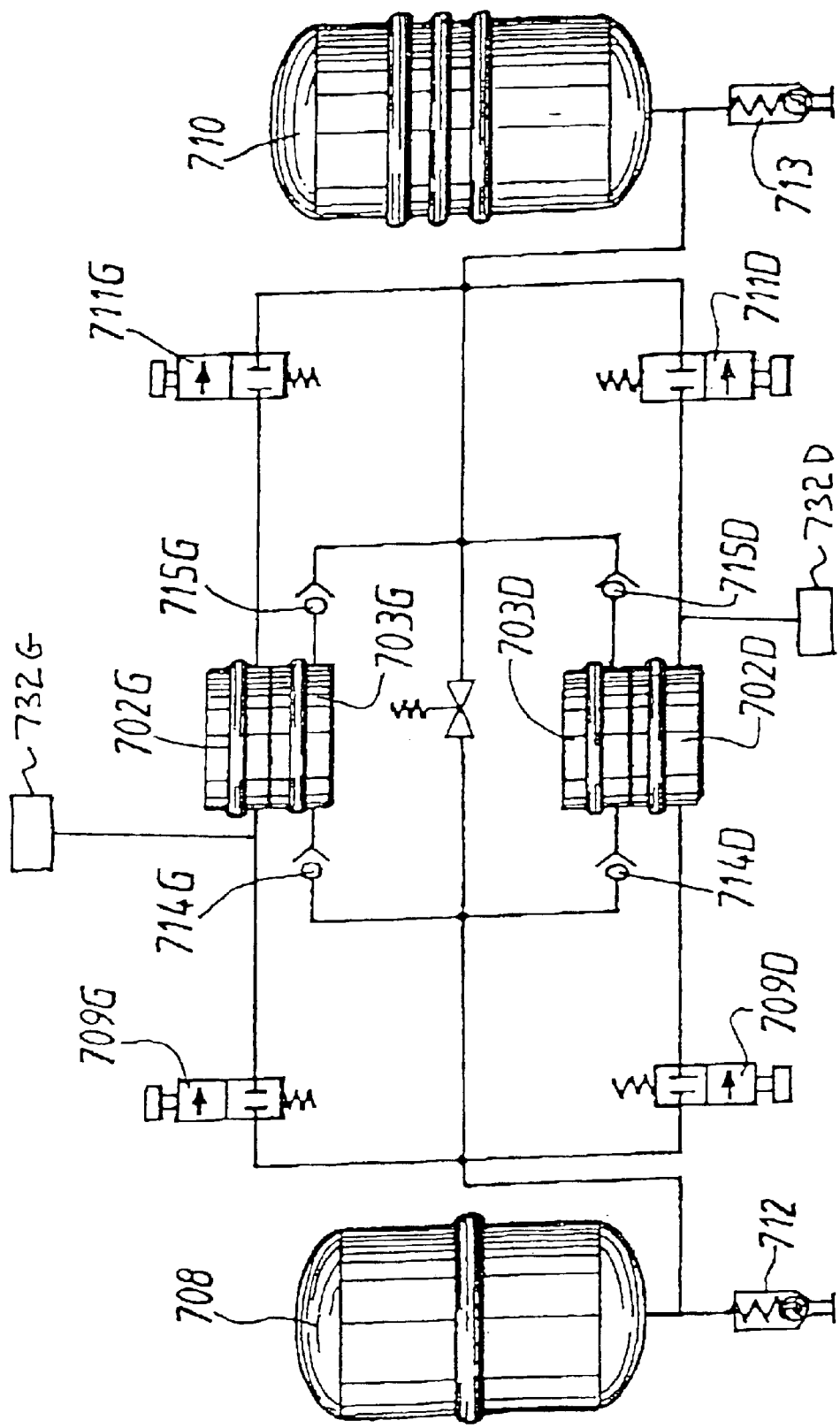
FIG. 47 is a schematic view of the entire hydraulic circuit of an arthrodesis of the vertebral column using implants of the same type as the one in FIG. 40.
Figure 49:
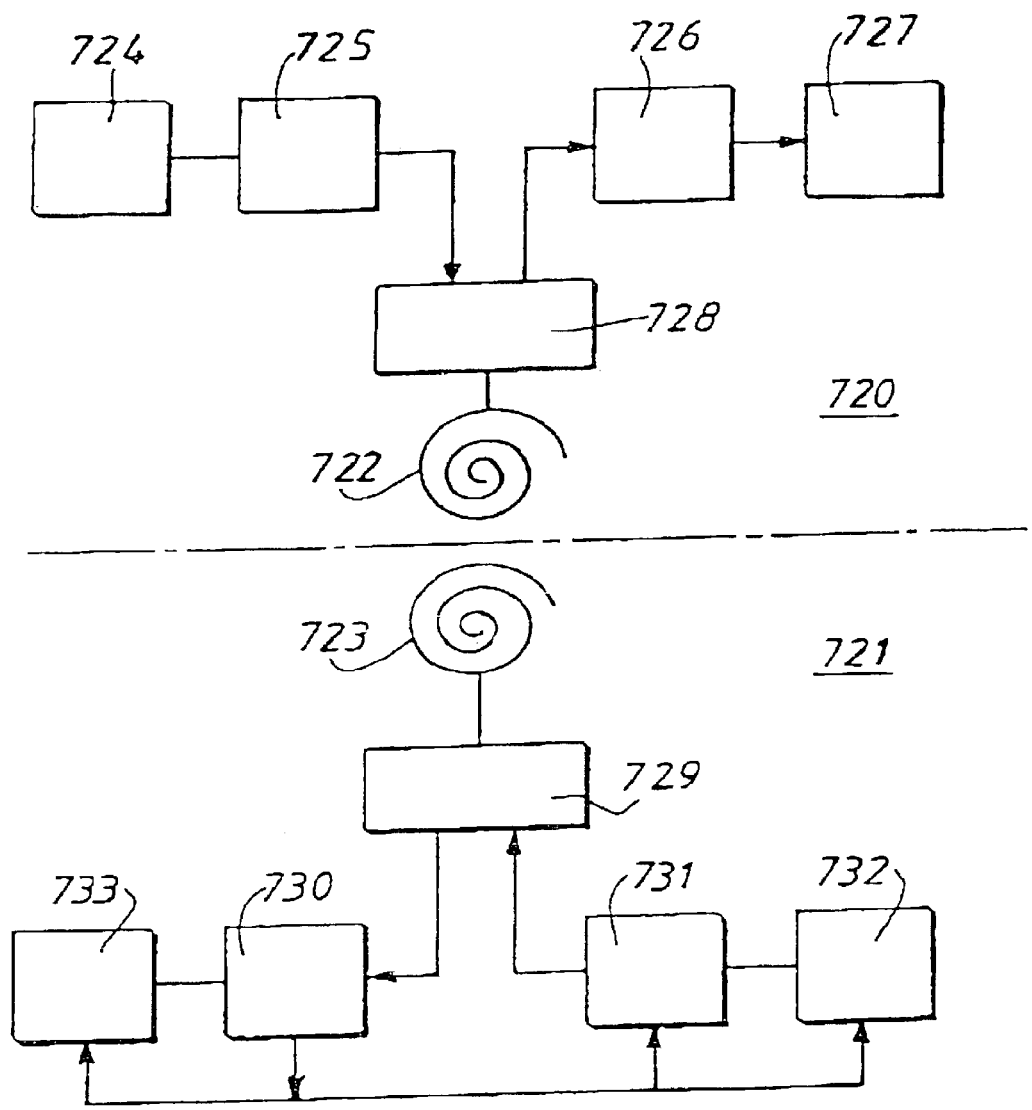
FIG. 49 shows an electrical wiring diagram of the control of an implant according to the invention.

By way of example, FIG. 49 illustrates an electronic control circuit for an implant of the type represented in FIG. 47.

This circuit is embodied in two parts, an extracorporeal part 720 and an implanted part 721. These two parts are in contact by means of two antennas 722 and 723, respectively.

The circuit part 720 comprises a power supply 724, a remote control device 725, a detection and amplification module 726, and a monitor 727. The remote control device 725 controls a radio frequency multiplexer 728 connected to the antenna 722.

The circuit part 721 also comprises a radio frequency multiplexer 729 connected to the antenna 723. The multiplexer 729 is connected to a radio frequency/D.C. voltage converter 730 which supplies electric power to the other modules of the circuit part 721, namely a radio frequency oscillator 731 and sensors 732, as well as actuators 733.

In the case of FIGS. 40 and 47, the sensors 732 can be, in particular, pressure sensors in the distance control elements 702, and possibly in the chambers of the viscoelastic cells 701. The actuators can comprise electrically operated valves such as the slide valves 709 and 711. More particularly, the pressure sensors can comprise, for each side of the patient, one sensor for each low-pressure chamber and one sensor for the high-pressure chamber. Pressure sensors can also be provided on the means for attaching the implants, such as screws or hooks, as well as on the bone, possibly bridged.

When the doctor wishes to know and possibly to adjust the pressure in the elements 702, for example, he operates the remote control device 725. The antenna 722, placed in proximity to the antenna 723, emits a code that is detected and used by the implanted part 721. Moreover, the radio frequency is transformed into a D.C. supply voltage for the sensors 732, the oscillator 731, and the multiplexer 729. The implanted part then in turn emits a code containing the pressure information, which is detected and displayed on the monitor 727. The adjustment of the elements 702 by means of the electrically-controlled valves 733 occurs in the same way.

It is noted that thanks to the invention, it is possible to perform a detailed examination of the behavior of the implants. For example, in the case of a vertebral implant, it is possible to measure its frequency response, or its impulse response, by having the patient sit on a seat equipped with means for moving in any direction desired, and by recording the response of the pressure sensors. The adjustment of the various stationary pressure levels can thus be determined with great precision.

It is noted that as implant according to the invention can include analgesic neurostimulating means of a known type, as well as a programmable medication delivery pump.

Generally, for all of the implants described above which do not have remote control by means of radio frequencies or the like, devices are provided which are accessible either directly, as in the case of subcutaneous buttons, or by means of a benign intervention. The means for adjusting by remote control without physical contact can be rotary valves of the "sluice" type which are multidirectional, whose rotation is induced by an external rotating magnetic field. A spiral spring re-establishes the equilibrium in the closed position. It is advantageous to be able to carry out the desired adjustments relatively often, either in a planned way, for example in order to progressively reduce the coefficient of resistance as a graft consolidates, or as necessary, for example in order to relieve pain.

Likewise, all of the above-mentioned implants can be provided with improvements which have only been described in reference to certain embodiments. This is the case, for example, with the dimensional adaptation provided in the implants of FIGS. 14 and 27. A disposition of this type is particularly useful in any implant intended for a child who is still growing, or an elderly person whose size is gradually decreasing.

In FIGS. 50 to 59 which follow, it is assumed that the spine extends in a vertical direction and that the two individual implants are arranged on either side of the succession of spinous processes, and that the lower pedicle screws are screwed into a first vertebra and the upper pedicle screws are screwed into another vertebra, which may or may not be adjacent and is arranged above the first one. The two individual elements are shown in a frontal plane which is the plane of the drawing. The result of this is that the pedicle screws should be oriented in a more or less sagittal plane, in other words more or less perpendicular to the plane of the drawing, or at any rate inclined, but for reasons of simplicity of representation they have been shown in the same frontal plane. Likewise, the joining elements have been shown in the same frontal plane, whereas they should be in the perpendicular or inclined plane which contains the pedicle screws.

Figure 50:
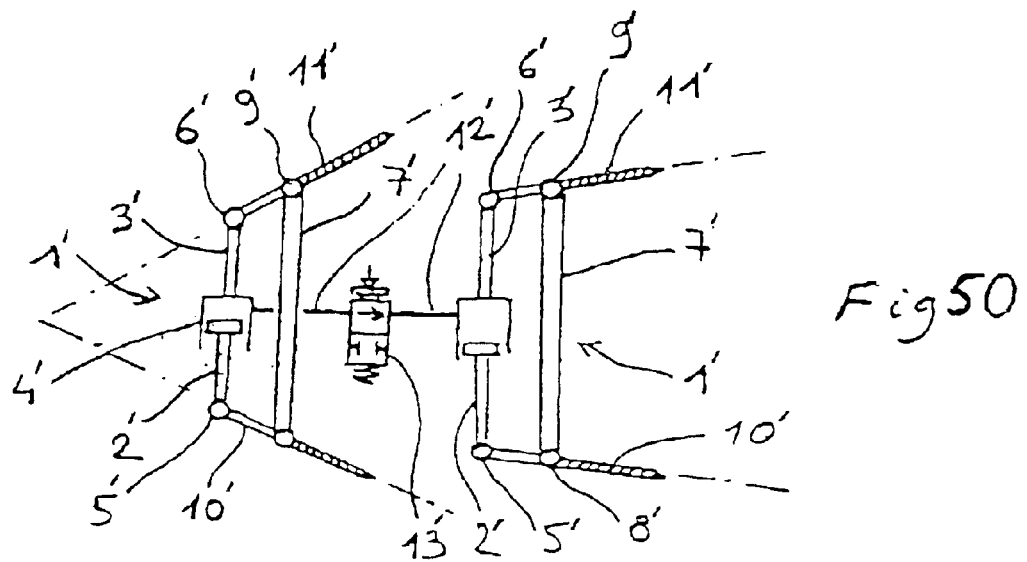
FIG. 50 shows a diagrammatic view of a pair of implants for antisymmetrical rotations according to a first embodiment of the invention.

FIG. 50 shows two individual implants, a right-hand one and a left-hand one, generally designated by 1' and comprising a lower end rod 2' and an upper end rod 3' between which there is interposed a deformable hydraulic element 4' which has been shown in the form of a cylinder/piston assembly, but which in reality would instead be in the form of a metal bellows so as to prevent the escape of hydraulic liquid. Alternatively, this deformable element can be of the telescopic type or of an otherwise deformable type, for example a cylindrical cell which is elastic longitudinally but not transversely. The rods 2' and 3' are guided in the continuation of one another so as to move along the same vertical axis and to take up distanced or close positions as a function of the extent of filling of the deformable element 4'. The lower and upper ends 2', 3' have attachment means 5', 6' in the form of articulations. Extending parallel to the element 1' there is a rigid joining rod 7' which terminates in lower 8' and upper 9' attachment means in the form of articulations. The rod 7' extends essentially parallel to the individual element 1', but it could be more inclined, and can be made integral with this element, although this is not a requirement. Connected to each element 1' there is a lower pedicle screw 10' and an upper pedicle screw 11' whose threaded parts are fixed in the corresponding vertebral pedicles. The posterior end of the pedicle screws 10', 11' is received in the ends 5' and 6' in the manner of an articulation permitting an angular clearance at least in the plane constituted by the element 1' and the joining element 7'. If appropriate, the articulation can have a supplementary degree of freedom or can be of spherical shape giving a degree of freedom in rotation in all directions.

In an intermediate position, the screws 10', 11' are fixed and articulated respectively on the ends 8' and 9' of the joining element 7' by articulations also permitting an angular clearance in the common plane, for example the sagittal plane, of the element 1' and of its joining element 7'.

The two deformable elements 4' of the pair of individual implants which form the complex implant shown in the drawing are connected via a line 12' on which there is arranged a hydraulic circuit element 13', shown in the example in the form of a slide valve.

The configuration shown in FIG. 50 permits antisymmetrical rotation movements of the pedicle screws.

It is assumed that the pedicle screws have been screwed in the angular positions shown on the drawing, that the hydraulic circuits and the elements 4' are entirely filled with hydraulic liquid and that the valve 13' is in the closed position. In such a situation, the pedicle screws are blocked in their angular position shown on the drawing. In this position, the internal volume of the left-hand element 4' is smaller than that of the right-hand element 4', which corresponds to a more closed angle. If the valve is now opened, it will be appreciated that the pedicle screws are going to be able to pivot about the center of articulation of the points 8' and 9' at the end of the joining rod, as a function of the increase or reduction in the length of the corresponding element 1', itself dictated by the volume of liquid present in the associated deformable element 4'. Given the communication 12' between the two deformable elements 4', it will also be appreciated that any variation in the volume of liquid of one of the elements is compensated by an inverse variation in the volume of the other in such a way that the rotation of the pedicle screws in one direction on one of the elements is translated into a rotation of the pedicle screws in the other direction and having essentially the same absolute angular value.

This property can be made use of in various applications described in the above-mentioned EP and US applications.

If the hydraulic circuit element 13' is a viscoelastic regulating element which considerably brakes the passage of liquid, or prohibits this in the event of an abrupt angular movement of the pedicle screws, the vertebrae can be left free to pivot relative to one another in the frontal plane of the spine when the movements are slow, and, by contrast, the screws can be immobilized or their rotation considerably braked when the movements have a tendency to be rapid. In this way it is possible to obtain a damping effect in rotation while at the same time permitting a freedom of rotation for slow movements.

If the element 13' is an element with which it is possible to impose the supply of the hydraulic liquid into one of the deformable elements 4' and the withdrawal of the same volume of liquid from the other element 4', this supply then being followed by a closure of the communication, it is possible, some time after having implanted the two individual implants with given angles of pedicle screws, to initiate an external command, for example a transcutaneous magnetic command, in order to modify the angle and thereby to effect in small stages a correction of a vertebral deformation.

Means can be provided for exerting a continuous or intermittent constant pressure in the bellows 4' in such a way as to permanently stress the skeletal parts whose position is to be corrected.

Of course, by using different hydraulic circuits, it is possible to achieve the two functions which have been described, as has been explained in the abovementioned applications.

Of course, according to the invention, it is also possible to use each individual implant with its joining rod as a totally independent element and to control each of the elements separately without any interconnection 12', in order to ensure some or all of the functions of modification of length and thus of angulation, as well as viscoelastic damping.

In a preferred manner, the implant element is also combined with a device with which it is possible to supply a deformable element 4' with high-pressure liquid, if this is necessary, from a deformable bellows functioning, for example, as a pump actuated by the body, as has been described by the abovementioned application. In the case of the use of two individual implants for forming a complex implant, as shown, this supply and discharge means can be common to both implants.

Figure 51:
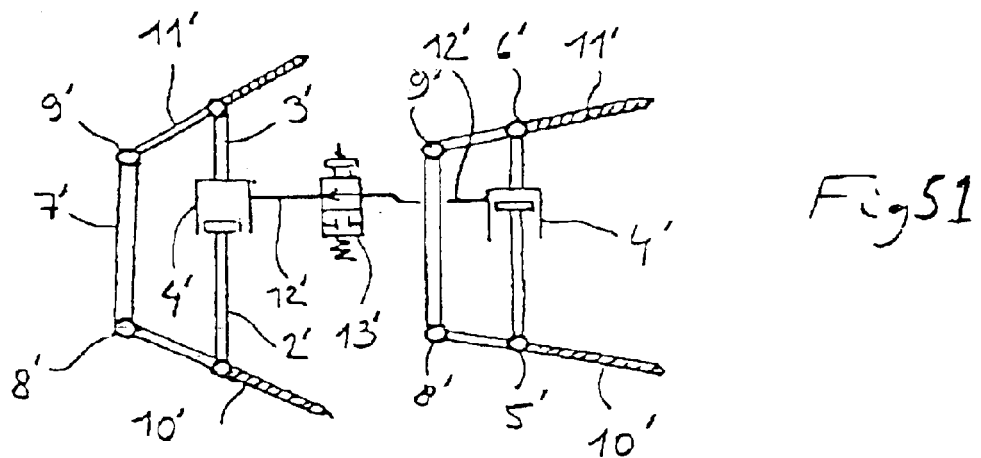
FIG. 51 shows another embodiment of such a pair of implants.

FIG. 51 shows a complex implant similar to that already described herein, but in which the joining rods 7' are articulated at the free ends or heads of the pedicle screws while the deformable individual element is articulated in the intermediate position, this giving an inversion of the movement of rotation relative to that shown in FIG. 50, and additionally moves the center of rotation of each pedicle screw rearwards.

Figure 52:
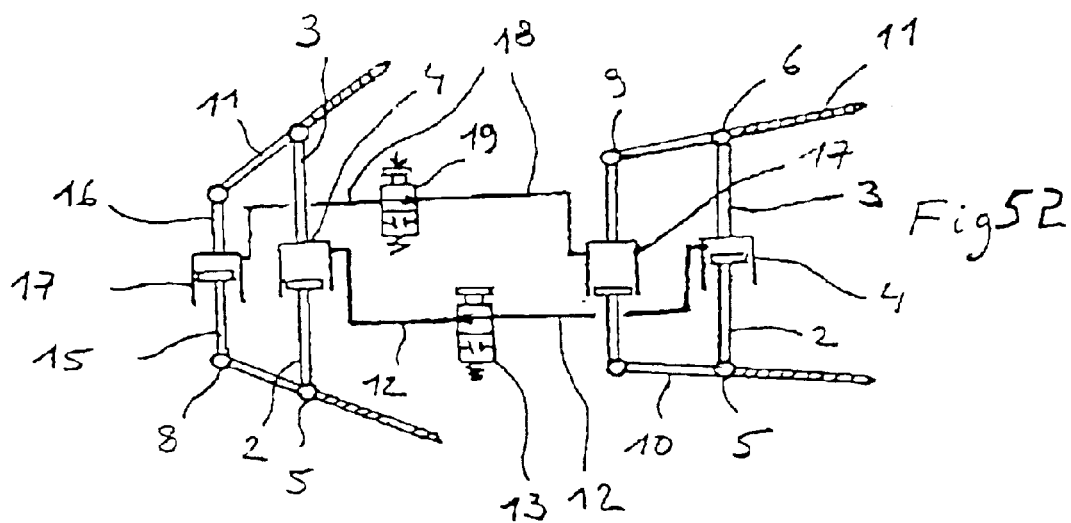
FIG. 52 shows another embodiment of such a pair of implants.

FIG. 52 shows a complex implant which is identical, for the individual implants 1', to that shown in FIG. 2. By contrast, the joining element 7', which was a single rigid rod, has been replaced by a joining element 14' formed in the manner of an individual implant and thus comprising two ends 15', 16' which are capable of moving longitudinally relative to one another with interposition of a deformable hydraulic element 17', by which means it is possible to have a joining element whose length can be modified if necessary or which can itself have a damping effect analogous to that of the actual implant 1 if this function is present.

Preferably, the two elements 17' of the two individual implants shown are connected via a channel 18' with interposition of a hydraulic circuit element 19'.

The desired functions will then be determined by the nature and control of the hydraulic regulating elements 13' and 19' and it will be appreciated that in such a design it is possible, if so desired, to make the implant element 1' and its joining element 14' interchangeable and thus to fix the center of rotation of the pedicle screw either at the end 5' (or 6') or at the end 8' (or 9') or even at another point between these articulations.

FIG. 53 is a diagrammatic representation of a practical embodiment of the device in FIG. 52 (on which the lines and the hydraulic circuit elements 13', 17' are not shown). The individual implant shown includes a hydraulic bellows 4' bearing on its upper face a component with an arm forming the rod 3', on its lower face a plate with an arm 2' forming the lower rod, the said rods having articulations 5' and 6' for the pedicle screws 10', 11'. The element 14' includes a hydraulic bellows 17' whose lower plate bears an arm 15' and the upper end an arm 16', the said arms bearing, at their free end, the articulations 8', 9' receiving the posterior ends of the screws 10', 11'. If appropriate, one arm of the element 1' and another arm of the element 14' can be mechanically secured or, by contrast, all these elements can be left independent, the link then being made only by the screws 10', 11'.

Thus, it is possible to arrange the bellows spatially one below the other and to form an implant according to the invention with a greatly reduced size.

In FIG. 54, now, a device has been shown which is analogous to that in FIG. 1, the only difference being that one of the deformable devices or bellows 4' has been replaced by a deformable device 20', which furthermore can also be made in the form of a bellows and in which the points of attachment of the lower 2' and upper 3' arms have been inverted, in such a way that an increase in the volume of the device 20' entails, in contrast to the increase in volume of the device 4', a shortening of the implant element instead of a lengthening.

It is thus possible, by virtue of the interconnection via the line 12' and the element 13', to obtain symmetrical rotation movements instead of antisymmetrical rotation movements. In other words, the rotations of the screws 10', 11' on the right-hand side of the spine are identical to the rotations of the screws of the left-hand element, and of the same direction.

It is thus possible to obtain movements of flexion or extension of the spine this time in the sagittal plane.

As in the other cases, this can be made use of either to provoke a lordosis effect or vice versa, depending on the desired aim, for example by acting in stages from an external command, or to achieve a perfectly symmetrical damping effect in the case of spontaneous movement of rotation between the vertebrae, or else to achieve the two functions simultaneously by virtue of more complex circuits.

FIG. 55 shows a configuration according to FIG. 54, but in which the joining elements 7' are arranged, as in FIG. 2, in such a way that the center of rotation of the pedicle screws is arranged at the ends of the screws.

Alternatively, it is also possible to combine the solution of FIG. 50 and of FIG. 51, placing the element according to FIG. 1 on the right of the spine, for example, and an individual element according to FIG. 2 on the left, it being understood that in this case the angular variations of the right-hand screws will at all times be the inverse of those of the left-hand screws, but of more different absolute value.

FIG. 56 shows a complex implant which also permits symmetrical relations in the sagittal plane, as indicated in FIG. 55, but in which the joining rod 7' of each of the individual implants has been replaced by joining elements which are themselves of variable length, the one on the left being a joining element 14' as shown in FIG. 52, while the joining element on the right also has an inversion of action in the area of the bellows. In other words, an arrangement is obtained in which the movements of rotation on left and right are symmetrical in the sagittal plane.

Figure 57:
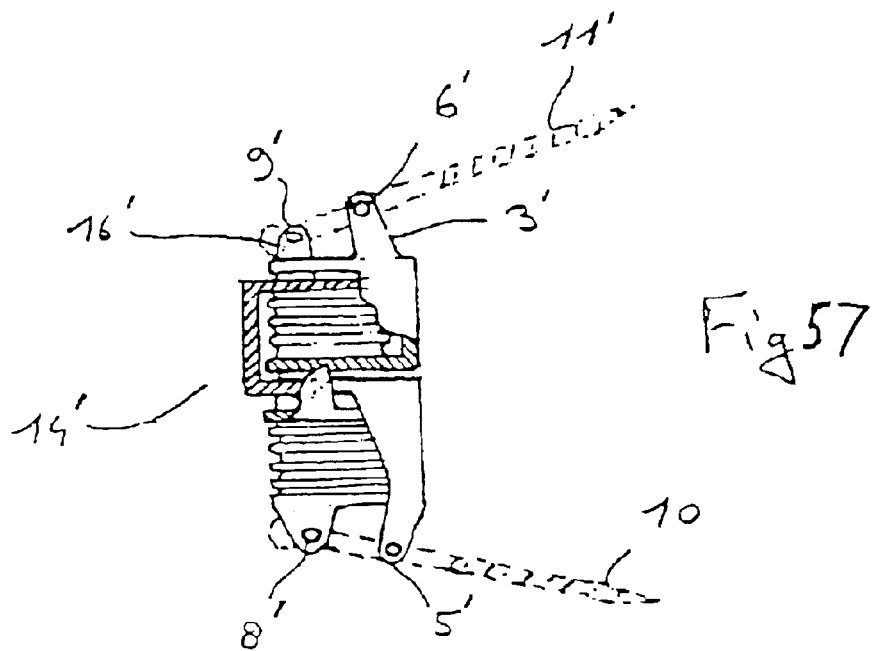
FIG. 57 shows a view of an embodiment of an implant from FIG. 56.

FIG. 57 is a diagrammatic representation of an embodiment analogous to FIG. 53, but in which it will be seen that, by inverting the bellow ends on which the arms are fixed, a movement is obtained in the opposite direction to that in FIG. 53.

Figure 58:
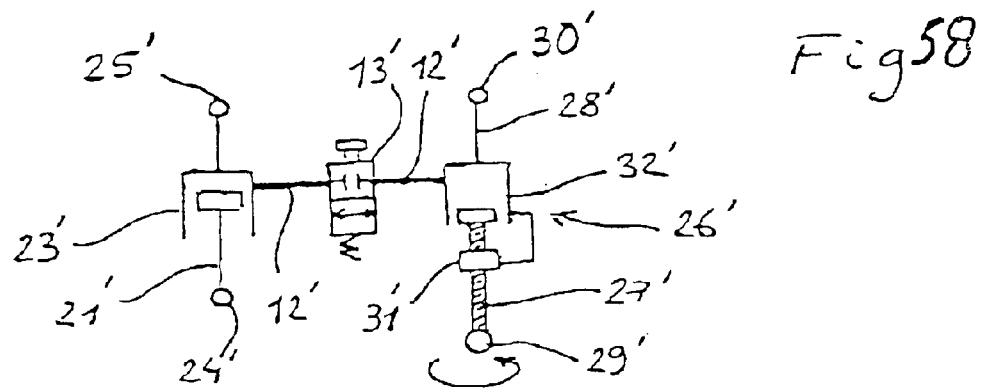
FIG. 58 shows a diagrammatic view of a pair of implants, one of which permits a simultaneous axial and rotational movement in a plane transverse to the general direction of the implant.

Referring to FIG. 58, this shows an assembly of two individual implants, of which the left-hand implant includes two end pieces 21', 22' which are able to move in the continuation of one another, with interposition of a deformable element 23' analogous to the deformable element 4'. The ends 24' and 25' of the pieces 21', 22' have fixation holes enabling anchoring means, for example pedicle screws to be secured. In contrast to the representations in the preceding figures, these fixation means at the ends 24', 25' do not necessarily permit a pivoting of the pedicle screws, such as the screws 10' and 11', and by contrast they can be formed by bores or eyelets which permit rigid connection without any possibility of pivoting of the screw relative to its corresponding end 24' or 25'.

The right-hand implant 26' also has two end pieces arranged in the continuation of one another, namely 27' and 28', of which the ends 29' and 30' are analogous to the ends 24' and 25' so as to receive the pedicle screws without any possibility of movement of the screw relative to the end which bears it. The end piece 27' has, starting from the end 29', a part in the form of an elongate threaded rod which terminates in the movable part of a deformable hydraulic element 32' analogous to the element 23' or to the element 4'. It will thus be appreciated that if the deformable element 32' deforms and provokes a relative movement, for example of spacing apart or distraction, between the pieces 27' and 28', the movement of the piece 27' relative to the piece 28' will provoke the rotation of the piece 27' on account of the fact that its threaded rod moves in the fixed nut 31'. The result of this is that the end 29' is driven relative to the end 30' in a displacement movement simultaneously of translation and rotation. Consequently, the end of the pedicle screw (not shown) borne by the piece 29' of the movable piece 27' will describe a helical movement whose axis is formed by the alignment of the pieces 27' and 28'.

If the two elements 20' and 26' are connected as is shown in the figure, by a valve 13' in a line 12', it will be appreciated that, as in FIG. 50, the reduction in the volume of the movable element 23' will translate into an increase in the volume of the movable element 32' and, thus, of the opposed axial displacements of the implants, with, in addition, the movement of rotation of the piece 27'.

Figure 59:
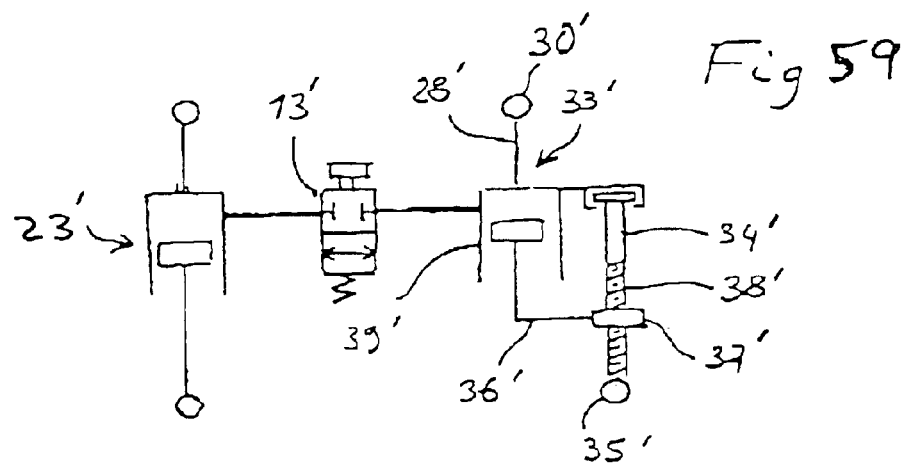
FIG. 59 shows a diagrammatic view of a pair of implants, one of which permits a rotation without translation movement, in a plane perpendicular to the general direction of the implant.

Reference is now made to FIG. 59. In this figure, the element 23' is identical to that in FIG. 58. Like the implant 26', the other implant 33' has an end piece 28' terminating in an end 30' which permits the fixation and blocking of an anchoring screw. By contrast, the element 33' includes a second end piece 34' with its end 35' for receiving and blocking the anchoring screws, this piece 34' being connected to the element 28' in such a way as to be immobilized in translation but free in rotation about the axis of the piece 34'. The movable part 36' of the deformable element 39' has a piece in the form of a tapped nut 37' through which a threaded part 38' of the piece 34' passes. It will thus be appreciated that when the deformable element 39' deforms, the movement of the movable piece 36' will provoke a rotation of the end piece 34' about its axis, but without translation relative to the end piece 28', in such a way that the end 35' turns without displacement in translation relative to the end 30'.

In the embodiment shown in FIG. 59, by virtue of the valve 13', a variation in the volume of the deformable element 20' will translate into an inverse variation in the volume of the deformable element 39', in such a way that the lengthening of the element 20' translates into a rotation of the end 35' in one direction, whilst the shortening of the element 20' produces a rotation of the end 35' in the opposite direction.

Of course, all the other control combinations can be realized, for example in the case of FIG. 58, in order to provoke identical lengthening of the elements 23' and 32' while ensuring the rotation of the piece 27'.

Referring to FIGS. 60 and 61, embodiments of the implant 26' in FIG. 58 are shown. It will be seen that the end pieces 27' and 28' have a streamlined shape in the form of a dolphin's snout and have transverse passages forming the ends 29' and 30' and permitting the fixation of a pedicle screw in an entirely traditional manner. In this figure, the portion forming the nut 31' is borne by the lower piece 27'. This nut 31' is traversed by a threaded rod 40' which is rigidly supported by the upper end piece 28' in such a way that the axial displacement of this rod provokes the rotation of the piece 28' relative to the piece 27'. The threaded rod 40', as will be seen in FIG. 61, passes into a pot 41' which is received in a leaktight manner inside the hydraulic bellows 32' acting as movable element, and the rod 40' can turn in this pot about its axis while being retained inside the pot by a securing ring 42'. It will be seen from this that it is also possible to give the overall implant an elongate streamlined shape particularly appropriate for good cohabitation with the surrounding tissue.

Referring to FIG. 62, this shows an embodiment of an implant 33' according to FIG. 59 with an upper end 28' and a lower end piece 34' which has arms 43' ending in a bearing 44' inside which there can freely turn, while being retained axially by a securing ring 45', a threaded rod 46' which is integral with the piece 28' and is capable of turning inside a nut 47' of a pot 48' fixed in a leaktight manner on the metal bellows 49' at the end integral with the end piece 34'. It will be appreciated that any movement of the bellows provokes an axial movement of the nut 47', which provokes a rotation without axial movement of the piece 28' relative to the piece 34'.

We now describe the use of a double implant for the correction of scoliosis in a patient having an angle of scoliosis a1 between the two scoliotic vertebral stages. During the operation, the surgeon employs traditional means to establish a preliminary correction bringing the angle of scoliosis to the value a2<a1. He then places the two individual implants on either side of the vertebral column between the two vertebral stages in question, with the valve 13' open, which permits the shortening of one of the individual implants and the compensating elongation of the other individual implant, and he fixes the two elements with the aid of their pedicle screws. It then suffices to re-close the valve 13' so that the two individual implants are blocked in their position without any possibility of movement and they maintain the scoliotic part of the vertebral column in the angle a2. From this moment onwards, all the loads are borne by the prosthesis constituted by the double implant.

After a reasonable postoperative period during which the stresses are supported essentially by the prosthesis, the neutral point of the vertebral column will adapt by virtue of the reorganization of the skeletal and paravertebral tissues, and this will reduce the load on the prosthesis in the standing position. It is possible either to estimate this reduction in load or to provide the prosthesis with pressure sensors which can be interrogated, preferably noninvasively, as is already well known, and which will indicate that the vertebral column has reached a state of equilibrium.

A new adjustment will then be made by asking the patient to bend sideways to reduce the value of the angle a of scoliosis to a value a2<a1 after opening the valve 13', which renders the two implants movable. Once this angle a2 has been obtained, the valve is closed again so that the two implants maintain this new position and prevent the return to a greater angle of scoliosis. This blocking of the prosthesis causes the patient the sensation of an obstacle which will gradually disappear until such time as a new equilibrium is found.

By means of a succession of these maneuvers, it is thus possible to reduce or even eliminate the angle of scoliosis and to remove the prosthesis.

It will be appreciated that the same principles can be used for gradually re-establishing kyphosis or lordosis by using pairs of implants which are arranged, for example, in accordance with the figures.

Likewise, by using a pair of prostheses as in FIG. 9, for example, it would be possible to gradually reduce kyphoscoliosis.

FIG. 63 shows a transverse cross section of an implant in a refined embodiment of the invention.

This implant 1' includes two parts in the form of end pieces 51' and 52' in the shape of a dolphin's head, having at their outermost parts holes or eyelets 53' and 54' through which it is possible to engage pedicle screws whose heads can be fixed rigidly in the area of the holes 53', 54'. Alternatively, these holes can be arranged in such a way as to permit an articulation of the head of the pedicle screw and thus an angular displacement between the end element and the screw which it bears.

Arranged between the two end pieces 51' and 52' there is a third piece 55' which is movable relative to the two ends. The piece 55' has a stirrup shape, of which one of the branches 56' supports a metal bellows 57' in a leaktight manner, the free end of which bellows is fixed in a leaktight manner against a piece 58' which is able to slide relative to the stirrup 55' and bears, in the manner of a journal, by virtue of a securing ring 45', but axially nonmovable relative to the piece 58', a threaded rod 59' which passes through a complementary tapped hole of the second branch 60' of the piece 55'. It will thus be appreciated that when the deformable element constituted by the bellows 57' deforms, the thus provoked axial displacement of the rod 59' integral with the upper end 52' entrains the rotation of this rod 59' in the fixed nut formed in the branch 60', and consequently a simultaneous movement of translation and rotation of the end piece 52' relative to the piece 60'.

Arranged inside the end piece 51' is a leaktight cavity 61' which serves as a high-pressure chamber and in which there is a bellows 62' which is hermetically sealed and in which a vacuum has been established. The stiffness of this bellows, however, is sufficient to ensure that it tends spontaneously to deploy and increase in volume even when it is surrounded by high pressure prevailing in the chamber 61'. The chamber 61' communicates via a nondeformable conduit 63' with the inside of the metal bellows 57' by way of a high-pressure valve 64' lodged in the branch 56'. This valve 64' has a tubular slide of soft iron 65' which is normally held back by a spring in the position closing off the passage towards the bellows 57'. It will be appreciated that when the plunger core 65' is brought into a position of opening counter to the valve spring, liquid at high pressure in the chamber 61' will run along the conduit 63' and enter the bellows 57'. The high pressure in the chamber 61' is maintained by the concomitant deformation of the sealed bellows 62'. This inflow of liquid provokes the displacement of the piece 58' towards the branch 60' and, consequently, the distraction and rotation of the end piece 52' relative to the central piece 55'.

The inside of the bellows 57' also communicates, by way of a low-pressure valve 66' equipped with a plunger core identical to the core 65' situated in the piece 58', with the volume 67' surrounding the various pieces contained inside the deformable impermeable sleeve 68', at the two ends of which the ends of the pieces 51' and 52' emerge, this volume 67' forming the low-pressure volume. It will be appreciated that when the valve 66' is opened, liquid contained in the bellows 57' will exit and spread through the low-pressure volume 67', thus permitting a retraction or compression of the bellows 57' and a simultaneous rotation of the piece 52' in the opposite direction.

The high-pressure reservoir 61' is recharged by way of a metal bellows 69' which is of a diameter substantially smaller than that of the bellows 57' and which is interposed between the pieces 51' and 55'. When the pieces 51' and 55' move away from each other, this bellows 69' expands and aspires liquid from the low-pressure chamber 67' by way of a nonreturn valve 70'. By contrast, when the pieces 51' and 56' close together, the high pressure generated in the bellows 69' causes liquid at very high pressure to enter the high-pressure chamber 61' by way of a nonreturn valve 71'.

It is not necessary for the deformation of the bellows 69' to be of a great amplitude; on the contrary, it is preferable for the gap between the piece 51' and the piece 56' to be small and for the course of oscillation between the pieces 51' and 55' to be limited, a multiplicity of oscillations, for example, as the subject walks or changes position of his/her body sufficing to generate the high pressure permitting supply to the chamber 61'.

In such an embodiment, as long as neither of the valves 64' and 66' is open, the two pieces 51' and 52' can move relative to one another only by a very short distance, and this thus ensures that the two skeletal elements to which they are anchored, for example two vertebrae, are maintained in the chosen position. The device for establishing high pressure can even be used to obtain a certain viscous damping of the small displacements permitted between the pieces 51' and 55'.

It will also be appreciated that having arranged the high-pressure and low-pressure valves 64', 66' on either side of the bellows 67', one or other of these valves can easily be actuated, according to choice, for example by a strong magnet placed on the skin in line with one of the valves in order to attract the ferromagnetic plunger such as 65' towards the left of the drawing and to open the valve.

It will of course be appreciated that it would be possible to form an implant analogous to that which has just been described, but arranged so as not to provoke rotation between the two end pieces, but simply a movement of distraction or compression. It would also be possible to form an implant such as that in FIG. 13 using most of the structural arrangements in FIG. 14 so as to form an implant uniquely with rotation.

By combining with an implant of this type a joining rod analogous to the rods 7', and by forming at the ends of the pieces 51' and 52' articulation bearings permitting a pivoting of the pedicle screws relative to the said ends, it is also possible to form implants according to FIGS. 50, 51, or 54, or 55.

In the case where use is made of a large number of implants according to the invention arranged along the vertebral column between different levels of the spine, it is also possible to provide a single high-pressure reservoir and a single low-pressure reservoir as well as a single deformable element for establishing high pressure, this reservoir assembly being arranged away from the various individual implants and being connected to each of these by a low-pressure conduit and a high-pressure conduit, the implants themselves in this case not having any hydraulic deformable element other than the motor bellows acting as bellows 57'.

Also, the controllable valves, such as the valves 13', 19' or 64' or 66', instead of being controlled directly by way of a ferromagnetic plunger capable of being attracted by a magnet placed on the surface of the skin near the valve, could be controlled, in a hydraulic manner known per se, by a small pilot valve which is easier to actuate because it has a plunger of lower inertia, the pilot valve addressing a control pressure to the actual switching valve in order to open the latter, and the closure of the pilot valve, by contrast, provoking the closure of the main valve.

It will also be appreciated that it is possible to limit the movement of one of the ends relative to the other by providing traditional abutment means between the two pieces, which come into force if the travel of the deformable member or of the motor bellows exceeds a desired amplitude. Thus, this provides an element of safety in the case of a fault in the functioning of the implant which prevents it from exactly maintaining the desired position, for example escape of liquid or conduit deformation or excessive deformation of a bellows.

The implants according to the invention are preferably delivered with a temporary removable element which holds them in a position of desired spacing between the two end elements and which the surgeon removes once he has fitted the implant and fixed the pedicle screws or other anchoring means at the ends of the implant.

The invention also relates to a therapeutic surgical procedure for modifying the position of two portions or elements of the skeleton, for example two vertebrae, in which procedure at least one implant element according to the invention is fitted, one of the ends is fixed by an anchoring means to one of the portions or elements of the skeleton, and the other end is fixed by an anchoring means to the other portion or element of the skeleton, if appropriate after having carried out a preliminary correction of the relative position of the two portions or elements, the approach route and the tissues operated on are left to heal, then, preferably by noninvasive control means, a corrective displacement or force is produced causing corresponding stressing of the two end pieces of the implant, or the anchoring means, relative to one another.

This displacement can be provoked directly by the patient's body and, in this case, the displacement is permitted by permitting deformation of the movable element, for example a hydraulic bellows, then, when the displacement has been completed, all subsequent displacements are prohibited by blocking the deformable element.

In another embodiment, in order to provoke the displacement, a deformation of the movable element is temporarily provoked by applying a force with which it is possible to obtain the desired displacement, after which the movement of the deformable element is once again blocked and prevented.

In a third embodiment, by contrast, the movable element is allowed to exert a permanent force, preferably constant or possibly progressively variable, between the two ends and thus the two portions or elements of the skeleton, with an intensity of force which is insufficient to provoke an abrupt modification of dimension and an attack on the tissue opposing this dimensional variation, but which is sufficient to provoke, as is known per se in the field of surgery, a slow deformation and an adaptation of the various tissues until the desired corrected position is reached.

Such a procedure is particularly suitable for correction of scoliosis or kyphoscoliosis.

When a force is exerted between two skeletal elements by means of an implant according to the invention, this force can advantageously be from a few daN to 25 or 30 daN.

The device can advantageously include force or pressure sensors for limiting or regulating the force to be exerted. Such miniaturized sensors are available on the market.

It has been seen that the noninvasive control means can be magnets which, from outside the body, can displace or attract a ferromagnetic mass, such as a valve slide, counter to a spring or an elastic return means which brings the mass back to its initial position once the magnet has been removed.

It is also possible to use an external device which creates a magnetic or electromagnetic rotary field which, inside the body, turns a rotary piece, for example a rotary slide of a valve.

What is claimed is:

1. A skeletal implant of the type to be used to connect at least two elements of a skeleton, the skeletal implant comprising:
    a first part adapted to be connected to at least one of the at least two elements of the skeleton;
    a second part adapted to be connected to another of the at least two elements of the skeleton;
    a variable volume element adapted to move the first and second parts with respect to each other;
    a high-pressure chamber supplying fluid to the variable volume element; and
    a low-pressure chamber receiving fluid from the variable volume element; and
    a recharging variable volume element adapted to communicate with the high-pressure chamber and the low-pressure chamber.

2. The implant of claim 1, further comprising another variable volume element disposed in the high-pressure chamber.

3. The implant of claim 2, further comprising a high-pressure valve allowing fluid to enter the variable volume element from the high-pressure chamber.

4. The implant of claim 1, wherein the low-pressure chamber comprises a deformable impermeable sleeve.

5. The implant of claim 4, further comprising a low-pressure valve allowing fluid to exit the variable volume element and enter the low-pressure chamber.

6. The implant of claim 1, further comprising a third part having one end coupled to the first part and another end disposed between the variable volume element and the second part.

7. The implant of claim 1, wherein the variable volume element comprises one end coupled to the first part and another end coupled to a third part.

8. The implant of claim 1, further comprising a third part having a threaded opening which engages a threaded portion of the second part.

9. The implant of claim 1, wherein the recharging variable volume element comprises one end that is coupled to a third part and another end that is coupled to the first part.

10. The implant of claim 9, wherein the second part is rotatably coupled to at least one of the variable volume element and the third part.

11. The implant of claim 1, further comprising a sealed bellows disposed in the high-pressure chamber.

12. The implant of claim 1, wherein the recharging variable volume element comprises a metal bellows having one end coupled to the first part and another end coupled to a third part.

13. The implant of claim 1, further comprising a sleeve defining a variable volume of the low-pressure chamber.

14. The implant of claim 1, further comprising a high-pressure conduit connecting the variable volume element to the high-pressure chamber.

15. The implant of claim 1, wherein the variable volume element comprises a metal bellows.

16. The implant of claim 1, wherein at least one of the first part and the second part comprises an opening which is adapted to receive a connecting member, whereby the connecting member connects the first or second part to one of the at least two elements of the skeleton.

17. A skeletal implant of the type to be used to connect at least two elements of a skeleton, the skeletal implant comprising:
    a first part adapted to be connected to at least one of the at least two elements of the skeleton;
    a second part adapted to be connected to another of the at least two elements of the skeleton;
    a variable volume element having a first end coupled to the first part and a second end, the variable volume element being adapted to move the first and second parts away from each other;
    a third part having a first end coupled to the first part and a second end coupled to the second end of the variable volume element;
    a high-pressure chamber supplying fluid to the variable volume element; and
    a low-pressure chamber receiving fluid from the variable volume element.

18. The implant of claim 17, further comprising a recharging variable volume element which includes a first end coupled to the first end of the third part and a second end coupled to the first part.

19. The implant of claim 18, wherein the recharging variable volume element is adapted to communicate with at least one of the high-pressure chamber and the low-pressure chamber.

20. The implant of claim 17, wherein the second part is rotatably coupled to at least one of the variable volume element and the third part.

21. The implant of claim 17, further comprising a high-pressure valve allowing fluid to enter the variable volume element from the high-pressure chamber.

22. The implant of claim 17, further comprising a low-pressure valve allowing fluid to exit the variable volume element and enter the low-pressure chamber.

23. The implant of claim 17, wherein at least one of the first part and the second part comprises an opening which is adapted to receive a connecting member, whereby the connecting member connects the first or second part to one of the at least two elements of the skeleton.

24. A skeletal implant of the type to be used to connect at least two elements of a skeleton, said implant comprising at least two parts, each of which is capable of being connected to one of said at least two elements, said at least two parts being movable with respect to each other, wherein there is provided, between said at least two parts:
    at least one of:
        a means authorizing a displacement between said at least to parts, from a starting position to a displaced position; and
        a means exerting a force between said at least two elements of the skeleton;
    said means being responsive to control means and comprising at least one variable volume element containing a fluid;
    said control means comprising a high-pressure reservoir and a very high-pressure differential variable volume recharging element for sending fluid at high-pressure into said high-pressure reservoir;
    said high-pressure reservoir being connected to said at least one variable volume element via a high-pressure valve;

said at least one variable volume element being connected to a low-pressure reservoir via a low-pressure valve;

said very high-pressure differential variable volume recharging element being connected to said low-pressure reservoir via another low-pressure valve; and said very high-pressure differential variable volume recharging element being responsive to displacements of corporal parts for recharging of said high-pressure reservoir with said fluid.

25. The implant of claim 24, wherein said high-pressure reservoir is designed to maintain said fluid contained therein at high pressure, even when significant quantities of said fluid are sent to said variable volume element, provoking a substantial reduction in a volume of said fluid, in order to maintain a high value of pressure in said high-pressure reservoir, and wherein said high-pressure reservoir contains an energy accumulator in the form of a cell having an elastically deformable wall, said energy accumulator being configured to assume a compressed and reduced volume state when fluid is introduced into said high-pressure reservoir, and being configured to assume an expanded state to maintain a high pressure when fluid is withdrawn from said high-pressure reservoir.

26. A skeletal implant of the type to be used to connect at least two elements of a skeleton, said implant comprising at least two parts, each of which is capable of being connected to one of said at least two elements, said at least two parts being movable with respect to each other, wherein there is provided, between said at least two parts:

at least one of:
- a means authorizing a displacement between said at least to parts from a starting position to a displaced position, the means comprising at least one variable volume element containing a fluid; and
- a means exerting a force between said at least two elements of the skeleton;

said means being responsive to control means;

said control means comprising a high-pressure reservoir and a very high-pressure differential variable volume recharging element for sending fluid into said high-pressure reservoir;

said high-pressure reservoir being connected to said variable volume element via a high-pressure valve;

said variable volume element being connected to a low-pressure reservoir via a low-pressure valve; and said high-pressure valve and said low-pressure valve being relatively spaced apart from one another.

* * * * *